United States Patent
Kuehnle et al.

(10) Patent No.: US 12,180,526 B2
(45) Date of Patent: *Dec. 31, 2024

(54) SUBTERRANEAN MICROALGAE FOR PRODUCTION OF MICROBIAL BIOMASS, SUBSTANCES, AND COMPOSITIONS

(71) Applicant: Kuehnle AgroSystems, Inc., Honolulu, HI (US)

(72) Inventors: Adelheid R. Kuehnle, Honolulu, HI (US); Robert J. Schurr, Honolulu, HI (US); Norie Anne B. Nolasco, Waipahu, HI (US); Jacob F. Wallace, Honolulu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,522

(22) Filed: Jul. 1, 2022

(65) Prior Publication Data
US 2023/0287469 A1   Sep. 14, 2023

Related U.S. Application Data

(62) Division of application No. 16/744,869, filed on Jan. 16, 2020, now Pat. No. 11,377,675.

(60) Provisional application No. 62/792,966, filed on Jan. 16, 2019.

(51) Int. Cl.
| | |
|---|---|
| *C12P 19/04* | (2006.01) |
| *A23K 10/12* | (2016.01) |
| *A23L 17/60* | (2016.01) |
| *A61K 8/31* | (2006.01) |
| *A61K 8/34* | (2006.01) |
| *A61K 8/49* | (2006.01) |
| *A61K 8/73* | (2006.01) |
| *A61K 9/00* | (2006.01) |
| *A61K 31/01* | (2006.01) |
| *A61K 31/045* | (2006.01) |
| *A61K 31/409* | (2006.01) |
| *A61K 47/26* | (2006.01) |
| *A61Q 19/00* | (2006.01) |
| *C12P 5/02* | (2006.01) |
| *C12P 7/02* | (2006.01) |
| *C12P 17/16* | (2006.01) |

(52) U.S. Cl.
CPC .............. *C12P 19/04* (2013.01); *A23K 10/12* (2016.05); *A23L 17/60* (2016.08); *A61K 8/31* (2013.01); *A61K 8/34* (2013.01); *A61K 8/345* (2013.01); *A61K 8/4913* (2013.01); *A61K 8/73* (2013.01); *A61K 9/0014* (2013.01); *A61K 31/01* (2013.01); *A61K 31/045* (2013.01); *A61K 31/409* (2013.01); *A61K 47/26* (2013.01); *A61Q 19/007* (2013.01); *C12P 5/026* (2013.01); *C12P 7/02* (2013.01); *C12P 17/165* (2013.01); *A23V 2002/00* (2013.01)

(58) Field of Classification Search
CPC .. C12P 19/04; C12P 5/026; C12P 7/02; C12P 17/165; A23K 10/12; A23L 17/60; A61K 8/31; A61K 8/34; A61K 8/345; A61K 8/4913; A61K 8/73; A61K 9/0014; A61K 31/01; A61K 31/045; A61K 31/409; A61K 47/26; A61Q 19/007; A23V 2002/00
USPC .......................................................... 514/54
See application file for complete search history.

(56) References Cited

U.S. PATENT DOCUMENTS

| | | | |
|---|---|---|---|
| 4,683,202 | A | 7/1987 | Mullis |
| 5,882,849 | A | 3/1999 | Leonard et al. |
| 6,022,701 | A | 2/2000 | Boussiba et al. |
| 7,129,392 | B2 | 10/2006 | Hahn et al. |
| 7,135,620 | B2 | 11/2006 | Daniell et al. |
| 7,329,789 | B1 | 2/2008 | Schonemann et al. |

(Continued)

FOREIGN PATENT DOCUMENTS

| | | |
|---|---|---|
| EP | 1 501 937 A2 | 2/2005 |
| EP | 1 724 357 A1 | 11/2006 |

(Continued)

OTHER PUBLICATIONS

Abe, K. et al., "Accumulation and antioxidant activity of secondary carotenoids in the aerial microalga *Coelastrella striolata* var. *multistriata*," Food Chemistry, 2007, 100:656-661, 2005 Elsevier Ltd.

(Continued)

*Primary Examiner* — Yih-Horng Shiao
(74) *Attorney, Agent, or Firm* — Saliwanchik, Lloyd & Eisenschenk

(57) ABSTRACT

The invention pertains to a method for synthesizing a product of interest by culturing a microalgal cell obtained from a subterranean habitat for producing the product of interest. The microalgal cell obtained from a subterranean habitat can be cultured in the dark, in light, in low nutrition, or nutrient rich conditions for at least a portion of production cycle. A combination of these conditions can be used to specifically manipulate a microalgal cell culture to produce a product of interest. The product of interest can be a water-soluble carotenoid, for example, a water-soluble carotenoid produced by culturing an algae belonging to the genus *Haematococcus* or a capsular exopolysaccharide produced by culturing an algae belonging to the genus *Parachlorella*. Compositions containing the water-soluble carotenoid, for example, as sunscreen and compositions containing the exopolysaccharide, for example, as moisturizing cream are also described.

18 Claims, 11 Drawing Sheets

Specification includes a Sequence Listing.

(56) References Cited

U.S. PATENT DOCUMENTS

| | | |
|---|---|---|
| 7,618,819 B2 | 11/2009 | Kuehnle |
| 8,206,721 B2 | 6/2012 | Stutz et al. |
| 8,277,849 B2 | 10/2012 | Dillon et al. |
| 8,278,090 B1 | 10/2012 | Im et al. |
| 8,404,468 B2 | 3/2013 | Lucia et al. |
| 8,911,966 B2 | 12/2014 | Martin et al. |
| 8,972,522 B2 | 1/2015 | Coragliotti et al. |
| 9,278,122 B2 | 3/2016 | Laurent-Applegate et al. |
| 9,428,779 B2 | 8/2016 | Yohn et al. |
| 9,487,790 B2 | 11/2016 | Champagne et al. |
| 11,304,968 B2 | 4/2022 | DiMauro et al. |
| 2008/0038774 A1 | 2/2008 | Higashiyama et al. |
| 2009/0214475 A1 | 8/2009 | Hu et al. |
| 2009/0317878 A1 | 12/2009 | Champagne et al. |
| 2010/0316720 A1 | 12/2010 | Stutz et al. |
| 2012/0171733 A1 | 7/2012 | Im et al. |
| 2012/0202768 A1* | 8/2012 | Coragliotti .............. C12P 19/04 536/123 |
| 2012/0264195 P1 | 10/2012 | Biel et al. |
| 2014/0242109 A1 | 8/2014 | Kizaki et al. |
| 2015/0232802 A1 | 8/2015 | Ganuza et al. |
| 2015/0252391 A1 | 9/2015 | Li et al. |
| 2018/0002711 A1* | 1/2018 | Schurr ...................... C12P 7/26 |

FOREIGN PATENT DOCUMENTS

| | | |
|---|---|---|
| EP | 1 995 325 A1 | 11/2008 |
| EP | 2 754 710 A1 | 7/2014 |
| EP | 2 878 676 A2 | 6/2015 |
| EP | 2 977 462 A1 | 1/2016 |
| JP | 6174219 B2 | 7/2017 |
| RU | 2 541 455 C1 | 2/2015 |
| TW | I491349 B | 7/2015 |
| WO | 2003/027267 A1 | 4/2003 |

OTHER PUBLICATIONS

Alam, N. et al., "Review on in vivo and in vitro methods evaluation of antioxidant activity," Saudi Pharmaceutical Journal, 2013, 21:143-152, 2012 King Saud University.

Bashan, Y. et al., "Primary colonization and breakdown of igneous rocks by endemic, succulent elephant trees (*Pachycormus discolor*) of the deserts in Baja California, Mexico," Naturwissenschaften, 2006, 93:344-347, Springer-Verlag.

Chaiklahan, R. et al., "Stability of phycocyanin extracted from *Spirulina* sp.: Influence of temperature, pH and preservatives," Process Biochemistry, 2012, 47:659-664, Elsevier Ltd.

Chauton, M. S. et al., "Titanium uptake and incorporation into silica nanostructures by the diatom *Pinnularia* sp. (Bacillariophyceae)," J Appl Phycol, 2015, 27:777-786.

Delattre, C. et al., "Production, extraction and characterization of microalgal and cyanobacterial exopolysaccharides," Biotechnology Advances, 2016, pp. 1-21, Elsevier Inc.

Du Plessis, J. et al., "International guidelines for the in vivo assessment of skin properties in non-clinical settings: Part 2. transepidermal water loss and skin hydration," Skin Res Technol., 2013, pp. 1-22.

Falasco, E. et al., "Diatom flora in subterranean ecosystems: a review," International Journal of Speleology, Sep. 2014, 43(3):231-251.

Gan, F. et al., "Occurrence of Far-Red Light Photoacclimation (FaRLiP) in Diverse Cyanobacteria," Life, 2015, 5(1):4-24.

Guillard, R. R. L. et al., "Studies of Marine Planktonic Diatoms I. Cyclotella Nana Hustedt, and Detonula Confervacea (Cleve) GRAN. 1," Canadian Journal of Microbiology, 1962, 8:229-239.

Guillard, R. R. L. et al., "Purification Methods for Microalgae," Algal Culturing Techniques, pp. 1-18, 2005 Elsevier Inc.

Guiry, M. D. et al., "Chlorella kessleri Fott & Nováková," AlgaeBase, 1996-2018, pp. 1-2, http://www.algaebase.org.

Hanagata, N. et al., "Secondary Carotenoid Accumulation in Scenedesmus Komarekii (Chlorophyceae, Chlorophyta)1," J. Phycol., 1999, 35:960-966.

Howarth, F. G. et al., "Identification of roots in lava tube caves using molecular techniques: implications for conservation of cave arthropod faunas," J Insect Conserv, 2007, 11:251-261, Springer Science+Business Media B.V.

Malavasi, V. et al., "DNA-Based Taxonomy in Ecologically Versatile Microalgae: A Re-Evaluation of the Species Concept within the Coccoid Green Algal Genus *Coccomyxa* (Trebouxiophyceae, Chlorophyta)," PLOS ONE, 11(3):1-25, (Mar. 30, 2016).

Minyuk, G. et al., "Stress-induced secondary carotenogenesis in Coelastrella rubscens (Scenedesmaceae, Chlorophyta), a producer of value-added keto-carotenoids," Algae, 2017, 32(3):245-259, The Korean Society of Phycology.

Moreno, M. et al., "Microbial Diversity in Ozark Region Caves.," Astrobiology Science Conference, 2010, pp. 1-2.

Nienow, J. A. et al., "Ecology of subaerial algae," Nova Medwigia, Beiheft, Jan. 1996, J. Cramer.

Osorio-Santos, K. et al., "Seven new species of *Oculatella* (Pseudanabaenales, Cyanobacteria): taxonomically recognizing cryptic diversification," European Journal of Phycology, 2014, 49(4):450-470, Taylor & Francis.

Prouty, N. G. et al., "Groundwater-derived nutrient and trace element transport to a nearshore Kona coral ecosystem: Experimental mixing model results," Journal of Hydrology: Regional Studies, Jun. 2017, 11:166-177, Elsevier B.V.

Rangkadilok, N. et al., "Evaluation of free radical scavenging and antityrosinase activities of standardized longan fruit extract," Food and Chemical Toxicology, Mar. 2007, pp. 1-10.

Schumacher, J. et al., "How light affects the life of Botrytis," Fungal Genetics and Biology, 2017, 106:26-41.

Shimura, H. et al., "Absorption of Radionuclides from the Fukushima Nuclear Accident by a Novel Algal Strain," PLOS ONE, 2012, 7(9):1-7.

Thoisen, C. et al., "A simple and fast method for extraction and quantification of cryptophyte phycoerythrin," MethodsX, 2017, 4:209-213, Elsevier B.V.

Vinogradova, O. N. et al., "Species Diversity Gradient to Darkness Stress in Blue-Green Algae/Cyanobacteria: a Microscale Test in a Prehistoric Cave, Mount Carmel, Israel," Israel Journal of Plant Sciences, 1998, 46:229-238, Laser Pages Publishing, Ltd.

Vinogradova, O. N. et al., "Algae of the Sefunim Cave (Israel): species diversity affected by light, humidity, and rock stresses*," International Journal on Algae, 2009, 11(2):99-116, Begell House, Inc.

Wu, H. et al., "Stability and Antioxidant Activity of Food-Grade Phycocyanin Isolated from Spirulina platensis," International Journal of Food Properties, 2016, 19:2349-2362, Taylor & Francis Group, LLC.

Zammit, G. et al., "The subaerophytic cyanobacterium *Oculatella subterranean* (Oscillatoriales, Cyanophyceae) gen. et sp. nov.: a cytomorphological and molecular description," Eur. J. Phycol., 2012, 47(4):341-354, British Phycological Society.

Jeffryes, C. et al., "Metabolic Insertion of Nanostructured TiO2 into the Patterned Biosilica of the Diatom *Pinnularia* sp. by a Two-Stage Bioreactor Cultivation Process," ACS Nano, 2008, 2(10):2103-2112, American Chemical Society.

Meléndez-Martínez, A. et al., "The colourless carotenoids phytoene and phytofluene: from dietary sources to their usefulness for the functional foods and nutricosmetics industries," Journal of Food Composition and Analysis, Jan. 2018, pp. 1-61.

Meléndez-Martínez, A. J. et al., "The colourless carotenoids phytoene and phytofluene: from dietary sources to their usefulness for the functional foods and nutricosmetics industries," Journal of Food Composition and Analysis, Jan. 2018, pp. 1-61.

Office Action dated Sep. 22, 2021 in U.S. Appl. No. 16/744,869.
Notice of Allowance dated Mar. 2, 2022 in U.S. Appl. No. 16/744,869.
NCBI Blast:gb|KT886086| vs FM205846.1, analyzed on Sep. 18, 2021 (Year:2021).

Kuehnle, A., et al., "Some Microalgae from the Hawaiian Islands with a Focus on Industrial Applications," Current Biotechnology, 2015, 4(4):499-513.

(56) References Cited

OTHER PUBLICATIONS

Yuan, Jian-Ping et al., Potential health-promoting effects of astaxanthin: A high-value carotenoid mostly from microalgae, Molecular Nutrition & Food Research, 2011, 55(1):150-165, Wiley-VCH Verlag Gmbh & Co. KGaA, Weinheim.

Yu, J. et al., Biophotolysis-based Hydrogen Production by Cyanobacteria and Green Microalgae, Communicating Current Research and Educational Topics and Trends in Applied Microbiology, 2007, pp. 79-89, Formatex.

Wrolstad, Ronald E. et al., Alternatives to Those Artificial FD&C Food Colorants, Annual Review of Food Science and Technology, 2012, 3:59-77, Annual Reviews.

Wang, Xin et al., Photosynthetic terpene hydrocarbon production for fuels and chemicals, Plant Biotechnology Journal, 2015, 13(2):137-146, Society for Experimental Biology, Association of Applied Biologists and John Wiley & Sons Ltd.

Wang, Y et al., Growth-associated biosynthesis of astaxanthin in heterotrophic Chlorella zofingiensis (Chlorophyta), World Journal of Microbial Biotechnology, 2008, 24(9):1915-1922, Springer Netherlands.

Ukibe, Ken et al., Efficient screening for astaxanthin-overproducing mutants of the yeast *Xanthophyllomyces dendrorhous* by flow cytometry, FEMS Microbiology Letters, 2008, 286(2):241-248, Blackwell Publishing Ltd.

Tran, Duc et al., Identification of Dunaliella Viridis Using its Markers, International Journal of Applied Science and Technology, Apr. 2013, 3(4):118-126, Center for Promoting Ideas, USA.

Tjahjono, Agus Eko et al., Hyper-accumulation of astaxanthin in a green alga *Haematococcus pluvialis* at elevated temperatures, Biotechnology Letters, Feb. 1994, 16(2):133-138, Kluwer Academic Publishers.

Syrenne, Ryan D. et al., Production of Limonene, a Volatile Monoterpene, in the Freshwater Algae *Chlamydomonas reinhardtii*, Algal Biology, 2014, pp. 27-28, National Alliance for Advanced Biofuels and Bioproducts Synopsis (NAABB).

Stemmer, Willem P.C. et al., Single-step assembly of a gene and entire plasmid from large numbers of oligodeoxyribonucleotides, Gene, 1995, 164(1):49-53, Elsevier Science B.V.

Spijkerman, Elly et al., Elemental and fatty acid composition of snow algae in Arctic habitats, Frontiers in Microbiology, Oct. 29, 2012, 3(380):1-15.

Somchai, Parinyachat et al., Use of microalgae *Chlamydomonas reinhardtii* for production of double-stranded RNA against shrimp virus, Aquaculture Reports, May 2016, 3:178-183, Elsevier B.V.

Solymosi, K. et al., Food colour additives of natural origin, Colour Additives for Foods and Beverages, Mar. 2015, p. 3-34, Woodhead Publishing.

Sharon-Gojman, Revital et al., Advanced methods for genetic engineering of Haematococcus pluvialis (Chlorophyceae, Volvocales), Algal Research, 2015, 10:8-15, Elsevier B.V.

Scranton, Melissa A. et al., Chlamydomonas as a model for biofuels and bio-products production, The Plant Journal, 2015, 82(3):523-531.

Schmidt, Isabell et al., Biotechnological production of astaxanthin with Phaffia rhodozyma/Xanthophyllomyces dendrorhous, Applied Microbiology and Biotechnology, 2011, 89(3):555-571, Springer-Verlag.

Scaife, Mark A et al., Establishing Chlamydomonas reinhardtii as an industrial biotechnology host, The Plant Journal, 2015, 82(3):532-546.

Sambrook, Joseph et al., Protocol 6: Cloning PCR Products by Addition of Restriction Sites to the Termini of Amplified DNA, Molecular Cloning: A Laboratory Manual, Third Edition, Jan. 15, 2001, 2(8):37-41, Cold Spring Harbor Laboratory Press, New York.

Office Action dated Mar. 16, 2021 in European Application No. 17 740 210.4.

Chen, F., et al., "High Cell Density Culture of Chlamydomonas Reinhardtii on Acetate Using Fed-Batch and Hollow-Fibre Cell-Recycle Systems," Bioresource Technology, 1996, 55:103-110.

Wan, M., et al., "Sequential Heterotrophy-Dilution-Photoinduction Cultivation of Haematococcus pulvailis for efficient production of astaxanthin," Bioresource Technology, 2015, 198:557-563.

Shi, X.-M., et al., "High-Yield Production of lutein by the Green Microalga *Chlorella protothecoides* in Heterotrophic Fed-Batch Culture," Biotechnol. Prog. 2002, 18:723-727.

Chen, F., et al., "Heterotrophic Growth of Chlamydomonas reinhardtii on Acetate in Chemostat Culture," Process Biochemistry, 1996, 31(6):601-604.

Office Action dated May 14, 2019 in U.S. Appl. No. 15/640,246.
Office Action dated Dec. 4, 2019 in U.S. Appl. No. 15/640,246.
Office Action dated Jul. 8, 2020 in U.S. Appl. No. 15/640,246.
Office Action dated Jan. 25, 2021 in U.S. Appl. No. 15/640,246.
Notice of Allowance dated Feb. 25, 2021 in U.S. Appl. No. 15/640,246.
Office Action dated Jul. 6, 2023 in Canadian Application No. 3,028,227.
European Office Action dated Nov. 18, 2022 in European Application No. 17 740 210.4.
European Office Action dated Apr. 25, 2024 in European Application No. 17 740 210.4.
Office Action dated Dec. 12, 2023 in U.S. Appl. No. 17/197,484.
Office Action dated Jun. 6, 2023 in U.S. Appl. No. 17/197,484.
International Search Report and Written Opinion dated Oct. 20, 2017 issued in International Application No. PCT/US2017/040486, filed Jun. 30, 2017.

Shah, Md. Mahfuzur R et al., Astaxanthin-Producing Green Microalga Haematococcus pluvialis: From Single Cell to High Value Commercial Products, Frontiers in Plant Science, Apr. 28, 2016, 7(531):1-28.

Zhang, Zhen et al., A New Paradigm for Producing Astaxanthin From the Unicellular Green Alga Haematococcus pluvialis, Biotechnology and Bioengineering, Oct. 2016, 113(10):2088-2099, Wiley Periodicals, Inc.

Minhas, Amritpreet K. et al., A Review on the Assessment of Stress Conditions for Simultaneous Production of Microalgal Lipids and Carotenoids, Frontiers in Microbiology, May 3, 2016, 7(546):1-19.

Figueroa-Martinez, Francisco et al., When the lights go out: the evolutionary fate of free-living colorless green algae, New Phytologist, 2015, 206(3):972-982.

Terashima, Mia et al., A fluorescence-activated cell sorting-based strategy for rapid isolation of high-lipid Chlamydomonas mutants, The Plant Journal, 2015, 81(1):147-159, Society for Experimental Biology and John Wiley & Sons Ltd.

Schurr, Robert et al., Microalgae Crop Improvement: Tools for Quality Control and Molecular Breeding, Industrial Biotechnology, Jun. 2014, 10(3):237-243, Mary Ann Liebert, Inc.

Zhou, Y. et al., Characterization of a Chlamydomonas reinhardtii mutant strain with improved biomass production under low light and mixotrophic conditions, Algal Research, 2015, 11:134-147, Elsevier B.V.

Kumar, Anil et al., Development of an RNAi based microalgal larvicide to control mosquitoes, Malaria World Journal, Mar. 2013, 4(6):1-7.

Kobayashi, Makio et al., Light-independent, astaxanthin production by the green microalga *Haematococcus pluvialis* under salt stress, Biotechnology Letters, Jun. 1997, 19(6):507-509, Kluwer Academic Publishers.

Kobayashi, Makio et al., "Growth and Astaxanthin Formation of Haematococcus pluvialis in Heterotrophic and Mixotrophic Conditions," Journal of Fermentation and Bioengineering, 1992, 74(1):17-20, Elsevier B.V.

Kim, Eunseong et al., A Transformed Bacterium Expressing Double-Stranded RNA Specific to Integrin β1 Enhances Bt Toxin Efficacy against a Polyphagous Insect Pest, Spodoptera exigua, PLoS ONE, Jul. 14, 2015, 10(7):1-15.

Kazamia, Elena et al., An Engineered Community Approach for Industrial Cultivation of Microalgae, Industrial Biotechnology, Jun. 2014, 10(3):184-190, Mary Ann Liebert, Inc.

Hatlen, B. et al., Growth performance, feed utilization and product quality in slaughter size Atlantic salmon (*Salmo salar* L.) fed a diet with porcine blood meal, poultry oil and salmon oil, Aquaculture Nutrition, 2013, 19(4):573-584, John Wiley & Sons Ltd.

(56) References Cited

OTHER PUBLICATIONS

Hata, Norihiko et al., Production of astaxanthin by Haematococcus pluvialis in a sequential heterotrophic-photoautotrophic culture, Journal of Applied Phycology, 2001, 13(5):395-402, Kluwer Academic Publishers.
Göksan, Tolga et al., Growth Characteristics of the Alga *Haematococcus pluvialis* Flotow as Affected by Nitrogen Source, Vitamin, Light and Aeration, Turkish Journal of Fisheries and Aquatic Sciences, 2011, 11:377-383, Central Fisheries Research Institute (CFRI), Trabzon, Turkey.
Gimpel, Javier A. et al., In Metabolic Engineering of Eukaryotic Microalgae: Potential and Challenges Come with Great Diversity, Frontiers in Microbiology, Dec. 15, 2015, 6:1376, doi: 10.3389/fmicb.2015.01376.
Feng, Shuying et al., Dunaliella salina as a novel host for the production of recombinant proteins, Applied Microbiology Biotechnology, 2014, 98(10):4293-4300, Springer-Verlag Berlin Heidelberg.
Fábregas, Jaime et al., Two-stage cultures for the production of Astaxanthin from Haematococcus pluvialis, Journal of Biotechnology, 2011, 89(1):65-71, Elsevier Science B.V.
Doebbe, Anja et al., Functional integration of the HUP1 hexose symporter gene into the genome of C. reinhardtii: Impacts on biological H2 production, 2007, 131(1):27-33, Elsevier Science B.V.
Chua, Penelope R et al., Production of Soladiesel from Cellulose Feedstocks, Energy Research and Development Division Final Project Report, 2011, pp. 1-36, California Energy Commision.
Chisti, Y. et al., Fermentation (Industrial): Basic Considerations, Encyclopedia of Food Microbiology, 1999, pp. 663-674, Academic Press, London.
Chen, T. et al., Construction of Dunaliella salina heterotrophic expression vectors and identification of heterotrophically transformed algal strains, Sheng Wu Gong Cheng Xue Bao (Chinese Journal of Biotechnology), Mar. 2009, 25(3):392-398, English abstract only.
Chen, Tao et al., Employment of Organic Acids to Enhance Astaxanthin Formation in Heterotrophic Chlorella Zofingiensis, Journal of Food Processing and Preservation, Apr. 2009, 33(2):271-284, Wiley Periodicals, Inc.
Chekanov, Konstantin et al., Accumulation of Astaxanthin by a New Haematococcus pluvialis Strain BM1 from the White Sea Coastal Rocks (Russia), Marine Drugs, Aug. 15, 2014, 12(8):4504-4520.
Cerutti, Heriberto et al., RNA-Mediated Silencing in Algae: Biological Roles and Tools for Analysis of Gene Function, Eukaryotic Cell, Sep. 2011, 10(9):1164-1172, American Society for Microbiology.
Bumbak, Fabian et al., Best practices in heterotrophic high-cell-density microalgal processes: achievements, potential and possible limitations, Applied Microbiology and Biotechnology, 2011, 91(1):31-46, Springer Science & Business Media B.V.
Boyle, Nanette R. et al., Flux balance analysis of primary metabolism in Chlamydomonas reinhardtii, BMC Systems Biology, Jan. 7, 2009, 3:4, doi: 10.1186/1752-0509-3-4.
Ben-Amotz, Ami et al., Massive Accumulation of Phytoene Induced By Norflurazon in Dunaliella Bardawil (Chlorophyceae) Prevents Recovery From Photoinhibition, Journal of Phycology, 1987, 23(1):176-181.
Barbosa, M.J. et al., Effect of carotenoid source and dietary lipid content on blood astaxanthin concentration in rainbow trout (*Oncorhynchus mykiss*), Aquaculture, 1999, 176(3-4):331-341, Elsevier Science B.V.
Bar, Etan et al., Pigment and Structural Changes in Chlorella zofingiensis upon Light and Nitrogen Stress, Journal of Plant Physiology, 1995, 146(4):527-534, Elsevier GmbH.
Ambati, Ranga Rao et al., Astaxanthin: Sources, Extraction, Stability, Biological Activities and Its Commercial Application—A Review, Marine Drugs, Jan. 2014, 12(1):128-152, Multidisciplinary Digital Publishing Institute (MDPI), Basel, Switzerland.
Alonso-Gutierrez, Jorge et al., Metabolic engineering of *Escherichia coli* for limonene and perillyl alcohol production, Metabolic Engineering, 2013, 19:33-41, Elsevier Inc.
Alabi, Abayomi O. et al., Microalgae technologies & processes for biofuels/bioenergy production in British Columbia: Current Technology, Suitability, & Barriers to Implementation: Final Report, Jan. 14, 2009, pp. 1-88, The British Columbia Innovation Council.
Aflalo, Claude et al., On the Relative Efficiency of Two- vs. One-stage Production of Astaxanthin by the Green Alga *Haematococcus pluvialis*, Biotechnology and Bioengineering, Sep. 1, 2007, 98(1):300-305, Wiley Periodicals, Inc.
Rise, Moshe et al., Accumulation of Secondary Carotenoids in Chlorella zofingiensis, Journal of Plant Physiology, 1994, 144(3):287-292, Elsevier GmbH.
Orosa, M. et al., Production and analysis of secondary carotenoids in green algae, Journal of Applied Phycology, Oct. 2000, 12(3):553-556, Kluwer Academic Publishers.
Muhaemin, Moh. et al., Biomass Nutrient Profiles of Marine Microalgae *Dunaliella salina*, Jurnal Penelitian Sains, Sep. 2010, 13(3(D)):13313-64-13313-67, FMIPA Universitas Sriwijaya.
Morales-Sánchez, Daniela et al., Heterotrophic growth of microalgae: metabolic aspects, World Journal of Microbiology and Biotechnology, 2015, 31(1):1-9, Springer Netherlands.
McVittie, Anne, Flagellum Mutants of Chlamydomonas reinhardii, Journal of General Microbiology, Mar. 1, 1972, 71(3):525-540, Great Britain.
McCarthy, Sarah S. et al., White Mutants of Chlamydomonas reinhardtii Are Defective in Phytoene Synthase, Genetics, Nov. 2004, 168(3):1249-1257, Genetics Society of America.
Machado, Vilmar et al., RNA Interference: A new Strategy in the Evolutionary Arms Race Between Human Control Strategies and Insect Pests, Folia Biologica (Kraków), 2014, 62(4):335-343, Institute of Systematics and Evolution of Animal, PAS.
Lorenz, R. Todd et al., Commercial potential for Haematococcus microalgae as a natural source of astaxanthin, Trends in Biotechnology, Apr. 2000, 18:160-167, Elsevier Science Ltd.
Lorenz, R.Todd, A Technical Review of Haematococcus Algae, Cyanotech Corporation: Technical Bulletin #060, 1999.
Liu, Xuebo et al., Cis astaxanthin and especially 9-cis astaxanthin exhibits a higher antioxidant activity in vitro compared to the all-trans isomer, Biochemical and Biophysical Research Communications, 2007, 357(1):187-193, Elsevier Inc.
Lewis, Louise A. et al., Green algae and the origin of land plants, American Journal of Botany, 2004, 91(10):1535-1556.
Lee, Yuan-Kun et al., Production of astaxanthin by Haematococcus, Chemicals from Microalgae, 1999, pp. 173-195.
Lauersen, Kyle J. et al., Efficient recombinant protein production and secretion from nuclear transgenes in Chlamydomonas reinhardtii, Journal of Biotechnology, 2013, 167(2):101-110, Elsevier B.V.
Zhang, Jiang et al., Full crop protection from an insect pest by expression of long double-stranded RNAs in plastids, Science, Feb. 27, 2015, 347(6225):991-994, American Association for the Advancement of Science, Washington, D.C., United States of America.
Zhang, Xue-Wu et al., Kinetic models for heterotrophic growth of Chlamydomonas reinhardtii in batch and fed-batch cultures, Process Biochemistry, 1999, 35(3-4):385-389, Elsevier Science Ltd.
Office Action dated Oct. 7, 2024 in U.S. Appl. No. 17/197,484.
Viso, A.-C., et al., "Fatty Acids From 28 Marine Microalgae," Phytochemistry, 1993, 34(6):1521-1533.

\* cited by examiner

```
                         SEQUENCE LISTING

Sequence total quantity: 8
SEQ ID NO: 1            moltype = DNA   length = 21
FEATURE                 Location/Qualifiers
source                  1..21
                        mol_type = other DNA
                        organism = synthetic construct
SEQUENCE: 1
aacctcgttg atcctgccag t                                              21

SEQ ID NO: 2            moltype = DNA   length = 23
FEATURE                 Location/Qualifiers
source                  1..23
                        mol_type = other DNA
                        organism = synthetic construct
SEQUENCE: 2
gatccttctg caggttcacc tac                                            23

SEQ ID NO: 3            moltype = DNA   length = 20
FEATURE                 Location/Qualifiers
source                  1..20
                        mol_type = other DNA
                        organism = synthetic construct
SEQUENCE: 3
aagattaagc catgcatgtc                                                20

SEQ ID NO: 4            moltype = DNA   length = 20
FEATURE                 Location/Qualifiers
source                  1..20
                        mol_type = other DNA
                        organism = synthetic construct
SEQUENCE: 4
gcggtgtgta caaagggcag                                                20

SEQ ID NO: 5            moltype = DNA   length = 20
FEATURE                 Location/Qualifiers
source                  1..20
                        mol_type = other DNA
                        organism = synthetic construct
SEQUENCE: 5
tagctggtct gagaggatga                                                20

SEQ ID NO: 6            moltype = DNA   length = 20
FEATURE                 Location/Qualifiers
source                  1..20
                        mol_type = other DNA
                        organism = synthetic construct
SEQUENCE: 6
taccttgtta cgacttcacc                                                20

SEQ ID NO: 7            moltype = DNA   length = 20
FEATURE                 Location/Qualifiers
source                  1..20
                        mol_type = other DNA
                        organism = synthetic construct
SEQUENCE: 7
caagtcatca gcttgcgttg                                                20

SEQ ID NO: 8            moltype = DNA   length = 20
FEATURE                 Location/Qualifiers
source                  1..20
                        mol_type = other DNA
                        organism = synthetic construct
SEQUENCE: 8
gttcgctatc ggtctcccgt                                                20
```

SUBTERRANEAN MICROALGAE FOR PRODUCTION OF MICROBIAL BIOMASS, SUBSTANCES, AND COMPOSITIONS

CROSS-REFERENCE TO RELATED APPLICATIONS

This application is a divisional of U.S. application Ser. No. 16/744,869, filed Jan. 16, 2020; which claims the benefit of U.S. Provisional Application Ser. No. 62/792,966, filed Jan. 16, 2019, which is hereby incorporated by reference in its entirety including any tables, figures, or drawings.

REFERENCE TO SEQUENCE LISTING

The Sequence Listing for this application is labeled "SequenceListing.xml" which was created on Jul. 1, 2022 and is 7,985 bytes. The entire content of the sequence listing is incorporated herein by reference in its entirety.

FIELD OF THE INVENTION

The present invention pertains to fermentation methods for producing biomass and bioproducts from microalgae obtained from subterranean habitats. In one embodiment, the present invention provides culturing microalgae obtained from subterranean systems in low or no light conditions for at least a portion of the production cycle.

BACKGROUND OF THE INVENTION

Subterranean microalgae are unexplored as a source of industrially manufactured useful substances. Subterranean habitats harboring microalgal as well as bacterial microflora can be found in a cave, tunnel, lava tube, fissure, crevasse, chasm, grotto, cavern, mesocavern, microcavern, or fumarole. These can be karst or pseudokarst (volcanic) formed of igneous, sedimentary, or metamorphic rock. Such subterranean habitats are biologically challenging environments, with microflora diminishing as the habitats go from the low light entry to the twilight zone and into the dark zone. Each zone presents differing physicochemical, geochemical, and nutrient states that influence microbial diversity and potential for colonization.

Microflora diversity is influenced by the age of a subterranean feature, its geometry (distance from, or spatial orientation relative to, an entrance or opening), and its geographic location (desert, ice, arctic, oceanic island, inland, tropical, temperate, humidity, rainfall, etc.). Age and geography also determine factors above the ground that, in turn, can impact the composition of any leachate entering into the subterranean feature. Biogenic substances can originate from bacterial microflora in the cave and also from subsurface leachate to provide organic acids, sugars, humic substances, decayed matter, minerals, metabolites, vitamins, and energy compounds to sustain microflora.

Subterranean microflora includes bacterial and microalgal organisms. An example of well-known subterranean bacterial microflora is Actinomycetes. These are filamentous bacteria seen as a slime of yellow, tan, white, copper, or reddish hues on cave walls and represent a source of nutrients and energy. Members of the Actinomycetes can fix atmospheric nitrogen for bioavailability, including as energy for nitrifying bacteria that oxidize ammonia into nitrites and nitrates. Actinomycetes also produce lytic enzymes that saccharify complex carbohydrates into fermentable or metabolizable monomeric sugars, such as for use by microalgae; and antibiotics, which in the subterranean habitat may enable slower growing eukaryotes to survive in the ecosystem.

Subterranean microalgal organisms refer to both the eukaryotic microalgae and the chlorophototrophic bacteria including cyanobacteria. As prokaryotes, some cyanobacteria also contribute nitrogen to ecosystems through nitrogen fixation and secretion of vitamins such as from the B-complex including thiamine (vitamin B1) and cyanocobalamin (vitamin B12).

To date subterranean microalgae are almost exclusively uncultured specimens collected to determine which microflora is present in a given habitat. This determination renders the specimens nonviable as they are cleaned by disinfectant, acid or heat prior to light or electron microscopy observation for morphological identification. They are also rendered nonviable when prepared for DNA extraction and molecular (nucleic acid sequence) identification. Uncommonly they may be placed in mineral solution under illumination to allow colonization sufficient to produce a sample on a microscope slide for light microscopy or to separate minute coccoid Chlorophytes into monoalgal cultures, generally in volumes at the scale of a petri dish, for easier identification.

As a result, methods of producing biomass and biological products from the substances produced by subterranean microalgae are not known. Such methods are needed to develop and produce compounds that can meet the increasing demand for innovative, functional ingredients used in health and personal care, especially in skin, lip, and hair care.

BRIEF SUMMARY OF THE INVENTION

In certain embodiments, the invention provides methods for synthesizing a product of interest by culturing a microalgal cell obtained from a subterranean habitat for producing the product of interest. The microalgal cell obtained from a subterranean habitat can be cultured in the dark, in light, in low nutrition, or nutrient rich conditions for at least a portion of production cycle. A combination of these conditions can be used to specifically manipulate a microalgal cell culture to produce a product of interest. The product of interest can be a microalgal biomass, exudate, pigment, or pigment precursor, lipid, protein, amino acid, carbohydrate, extracellular polysaccharide, or a complex thereof. Compositions using the microalgal substances are provided.

BRIEF DESCRIPTION OF SEQUENCES

Figure 1:
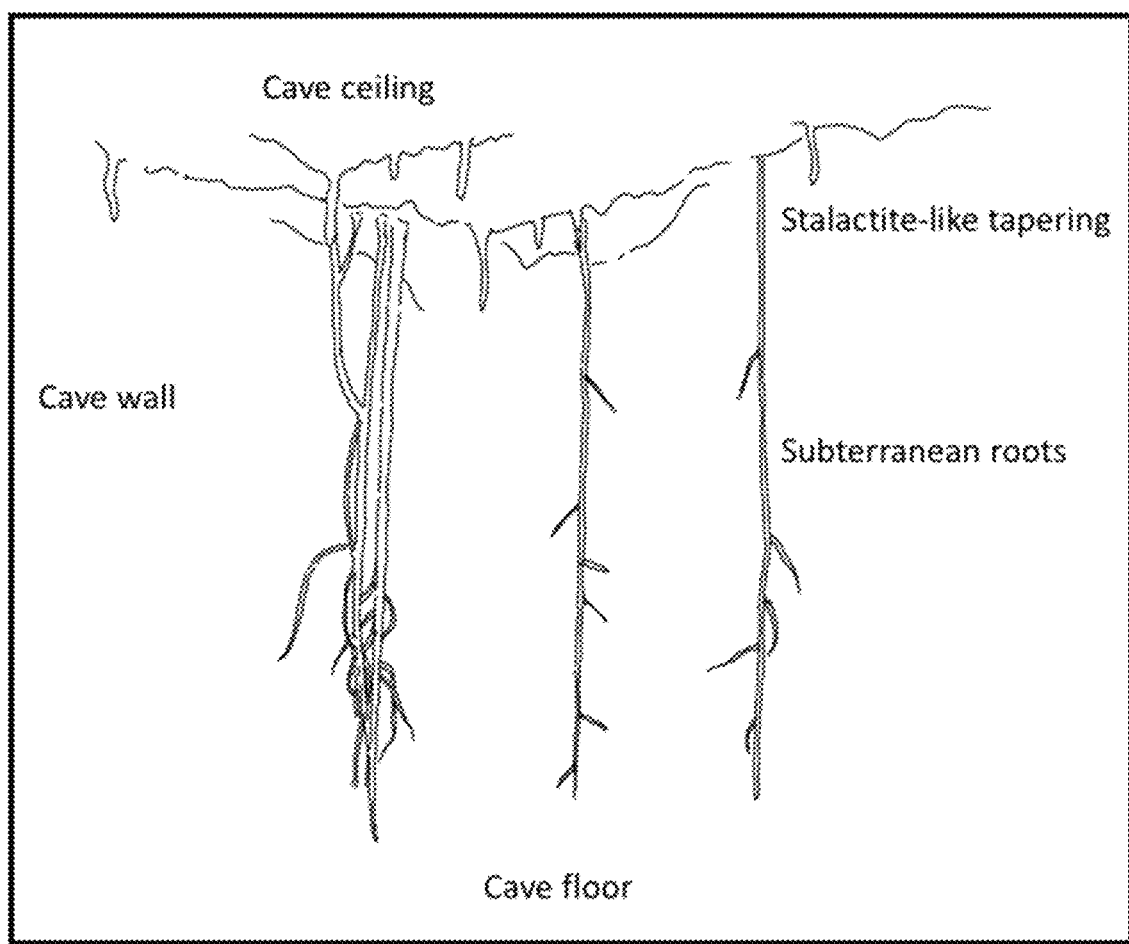
FIG. 1. Typical collection site in a lava tube or cave. Diagram of tree roots that have penetrated a cave. Also diagrammed are stalactite or other taperings that protrude from the ceiling; in limestone caves these can be calcareous deposits and with some potential biogenic formation, whereas in lava tubes they are structures patterned during the cooling of the lava. Percolating water containing nutrients can coalesce to flow down the protrusions as occasional drips or as more steady drip lines. Water can also be a constant seep on other surfaces. Subterranean algae can colonize these protrusions and surfaces including the walls, ceiling, loose rocks and in pools and may differ among specific substrata.

SEQ ID NOs: 1-4 are nucleotide sequences that are eukaryotic algae-specific primers that can be used to amplify 18s rRNA gene sequences.

SEQ ID NOs: 5-6 are nucleotide sequences that are cyanobacteria-specific that can be used to amplify a 16s rRNA gene sequence.

SEQ ID NOs: 7-8 are nucleotide sequences that can be used to amplify a DNA sequence of the ITS1 region of *Parachlorella* spp.

DETAILED DESCRIPTION OF THE INVENTION

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," "comprise," "consisting essentially of," "consists essentially of," "consisting," and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. When ranges are used herein, combinations and subcombinations of ranges (e.g., subranges within the disclosed range), specific embodiments therein are intended to be explicitly included.

The term "photoautotrophs" refers to an organism capable of synthesizing its own food from inorganic substances using light as an energy source. Examples of photoautotrophs include green plants and photosynthetic bacteria.

The term "replete nutrient condition" refers to a culture condition where all of the necessary nutrients are available in sufficient quantities to allow maximum growth of an organism.

The term "deplete nutrient" condition" refers to a culture condition where at least one of the necessary nutrients is not available in sufficient quantity to allow maximum growth of an organism. Such nutrient can be present in sub-optimal concentration, low concentration or can even be absent.

The term "facultative" refers to an organism that is capable of but not restricted to a particular mode of life. For example, a facultative anaerobe can synthesize ATP by aerobic respiration if oxygen is present but is capable of fermentation or anaerobic respiration if oxygen is absent.

The term "facultative heterotroph" refers to a photoautotrophic organism that is also capable of utilizing organic compounds for growth and/or maintenance and/or survival when light energy is not sufficient or is absent. The term also encompasses facultative heterotrophs and descendants thereof that lose their capability to perform photosynthesis, or acquire defects that result in their inability to grow as phototrophs, or are enabled to grow in the dark through genetically engineering, including for trophic conversion or for utilization of the preferred carbon feedstock.

The term "obligate heterotroph" refers to a cell that is unable to perform photosynthesis and requires an exogenous feedstock for survival. Some representative facultative heterotrophs and obligate heterotrophs that can grow in the dark in the presence of a carbon source are used in the method of the invention in a non-limiting manner.

The term "associates with" means, within the context molecular interactions, one molecule binding to another molecule. In reference to an exopolysaccharide substance in a complex with added protein or peptides, the affinity and selectivity of binding can vary when a polysaccharide and a polysaccharide binding protein or peptide are in association with each other. A formulated complex may sometimes be considered as "techno-functional," meaning the association adds a function to a substance.

The term "biogenic" refers to a substance produced by living organisms or biological processes. They may be either constituents or secretions and additionally may undergo changes over time. This may be as a result of biogeochemical processes. Sugars, sugar alcohols, and organic acids used in fermentation are biogenic. Enzymatic hydrolysis and fermentation are biogenic processes. Exopolysaccharides are biogenic secretions of contemporary origin. Diatomaceous earth is an example of biogenic secretions (marine animal shells or exoskeletons) of geologic age. A biogenic substance can also include volatile metabolites such as volatile fatty acids (VFAs) and volatile organic compounds. Forms of carbon and nitrogen are biogenic. Petroleum and natural gas are biogenic in origin, as are the products derived or synthesized from petroleum or natural gas.

The term "biomass" as used herein refers to a mass of living or non-living biological material and its derivatives and includes both natural and processed, as well as natural organic materials more broadly. Thus, "microalgal biomass," and "algal biomass" refers to material produced by growth and/or propagation of microalgal cells.

The term "biomass production" or "biomass accumulation" means an increase in the total number or weight of the cells of the organisms that are present in a culture over time. Biomass is typically comprised of cells; intracellular contents as well as extracellular material such as may be secreted or evolved by a cell; and can also be processed such that a fraction of the biomass is removed leaving residual biomass.

The term "biomimicry" or "biomimetic" means the design and production of materials, structures, and systems that are modeled on biological entities and processes. For instance, the supply of nutrients or illumination to a microbe being cultivated in an artificial environment (lab or production facility) can imitate a process that occurs naturally in its native habitat and is thus biomimetic.

The term "biomineralization" refers to the formation of complexes containing inorganic materials by living organisms. This includes biosilification and coccolithogenesis.

The term "biotic" means relating to or resulting from living organisms. The term "abiotic" means physical rather than biological, i.e., not derived from living organisms. A composition comprised of biogenic substances can be called a "biotic complex." A biogenic substance combined with an abiotic material can be called an "abiotic complex."

"Fed-batch fermentation" refers to a fermentation where one or more nutrients are supplied to a bioreactor during cultivation and in which the product remains in the bioreactor until the end of the fermentation run.

A "product of interest" is a substance synthesized by a cell. Examples of a product of interest include but are not limited to, proteins, lipids, carbohydrates, biogases, volatile materials, sugars, amino acids, isoprenoids, terpenes, or precursor thereof. Such substances may be synthesized constitutively by the organisms throughout growth and the amount of the substance in the culture may increase simply due to an increase in the number of organisms. Alternatively, the synthesis of such substances may be induced or altered in response to culture conditions or other environmental factors, for example, nitrogen starvation or elevated ammonium levels, or components from cellulosic hydrolysates.

The term "cosmetically effective amount" of a substance is understood to be non-toxic but sufficient amount to provide the desired effect. Such substance is produced by the methods of the invention.

The term "dermatological condition" refers to a cosmetic problem or disease of the skin, scalp, hair, and nails.

The term "fetal skin cell proteins" refers to a large number of proteins and peptides. This can include cytokines; enzymes; and structural proteins of the extra cellular matrix. Structural proteins can be present in the form of proteoglycans; where the protein is attached to chains of repeating disaccharide units termed glycosaminoglycans (GAGs).

The amount of a substance (or product) of interest accumulated over time relative to the culture volume and relative to their original amount is considered as "substance (or product) accumulation" or "substance (or product) production" that can be measured or quantified such as by % composition or specific productivity, or on a relative basis compared to a control culture.

The term "conditions favorable to cell division", in a general industrial context, means conditions in which cells divide at a rate such that an industrial production run is completed in about 24 to 60 to 168 to 240 hours, preferentially in less than 240, 144, 120, 96, or 72 hours, including a minimal lag time.

The term "cultivated" or "cultivation" or "culturing" refers to the purposeful fostering of growth (increases in cell size, cellular contents, and/or cellular activity) and/or propagation (increases in cell numbers via mitosis) of one or more microbial or microalgal cells by use of intended culture conditions. The combination of both growth and propagation may be termed proliferation. Examples of intended conditions include the use of a defined medium (with known characteristics such as pH, ionic strength, and carbon source), specified temperature, oxygen tension, and growth in a fermentor or bioreactor. The term does not refer to the growth of microorganisms in nature or otherwise without intentional introduction or human intervention, such as natural growth of an organism.

The term "fermentor," "bioreactor," "fermentation vessel," or "fermentation tank" means an enclosed vessel or partially enclosed vessel in which cells are cultivated or cultured, optionally in liquid suspension. A fermentor or bioreactor of the disclosure includes non-limiting embodiments such as an enclosure or partial enclosure that permits cultured cells to be exposed to light or which allows the cells to be cultured without exposure to light. The term "port," in the context of a vessel that is a fermentor or bioreactor, refers to an opening in the vessel that allows influx or efflux of materials such as gases, liquids, and cells. Ports are usually connected to tubing leading from the fermentor or bioreactor.

The term "fermenter" refers to an organism that causes fermentation.

The term "fixed carbon source" means a compound containing carbon that can be used as a source of carbon and/or energy by an organism.

The term "saccharide isomerate" refers to oligomeric and polymeric saccharides of defined structure and of natural or microbiological origin, generally used in industry as water-binding and water-retaining agents.

The term "exopolysaccharide or exopolymeric substances (EPS)" refers to polysaccharides secreted outside the cells. There are two broad types of EPS, those totally released into the surrounding environment (RPS) and those associated with the cell surface, which are themselves classified in 3 sub-groups: sheaths, capsule and slime (the latter is for cyanobacteria). RPS is physically released from the cell to become soluble in the culture media and is also referred to as "soluble exopolysaccharide." In contrast, capsular EPS remains attached to the cell, sometimes called "bound" EPS. It is distinct from carbohydrates that remain within the cell wall matrix such as cellulose, referred to as "cell wall polysaccharides." Exopolysaccharides are usually a polymer of monosaccharide units and have high molecular weights, although fragments can be smaller. EPSs are classified as homopolysaccharides and heteropolysaccharides. The former consists of only one type of monosaccharides, mostly glucose or fructose while the latter consist of two or more than two types of monosaccharides mostly glucose, galactose, rhamnose, and mannose. Some microalgal groups known to produce EPS include Cyanophytes, Chlorophytes, Rhodophytes, Bacillariophytes and others (Delattre et al. 2016).

The term "oligosaccharide" means a carbohydrate whose molecules are composed of a relatively small number of monosaccharide units.

The term "intrinsically disordered protein" (IDP), also known as a natively unstructured protein, refers to a protein that lacks a fixed or ordered three-dimensional structure. In some cases, IDPs adopt a fixed three-dimensional structure after binding to other macromolecules. IDPs are generally characterized by a low portion of bulky hydrophobic amino acids and a high proportion of polar and charged amino acids, usually referred to as low hydrophobicity. This property leads to interactions with water molecules.

The term "oligotrophic" refers to nutrient-limited environment or an environment relatively low in nutrients. An oligotroph is an organism that can grow in nutrient poor conditions.

The term "organic acid" refers to one or more molecules that are organic compounds with acidic properties. The most common organic acids are the carboxylic acids, which are pervasive in nature. A "carboxylic acid" contains a carboxyl group distinct from sugar carbohydrates such as glucose commonly used in algal fermentation. Included in this group are fatty acids and amino acids, considered building blocks of life. Citric, lactic, pyruvic, oxaloacetic and other acids are continuously recycled in energy producing systems. Acetic acid is a two-carbon carboxylic acid, $CH_3COOH$, resulting biologically as fermentation and metabolic byproducts or chemically through synthesis. Propionic acid (propanoic acid) is a carboxylic acid with the chemical formula $CH_3CH_2COOH$. The anion $CH_3CH_2COO^-$ as well as the salts and esters of propionic acid are known as propionates (or propanoates). Other such acids can include but are not limited to cinnamic, fumaric, uric, glycolic, butyric, valeric, oxalic, benzoic, nicotinic, malic, and succinic acids. "Sugar acids" and "chlorogenic acids" are also organic acids and can include but are not limited to glucuronic, galacturonic and other uronic acids, and ferulic, with a carboxylic acid functional group such as obtained or produced from abiotic, biotic, or biogenic processes. Epimers (carbohydrate stereoisomers) of glucuronic acid include D-mannuronic, D-alluronic, D-galacturonic and L-iduronic acid. Organic acids can occur alone or in combination, as may occur naturally, for example in cellulosic derivatives.

The terms "heterotrophic conditions" and "heterotrophic fermentation" and "dark heterotrophic cultivation" or "dark heterotrophic culture" refer to the presence of at least one fixed carbon source and the absence of light during fermentation. "Mixotrophic fermentation" refers to cultivation in the presence of at least one fixed carbon source and the presence of light during fermentation.

The term "low light" refers to low photon flux densities as in the entry zone (generally around 2 to 20 µmol photon/$m^2$/s), and the twilight zone (generally around 0.1 to 5 µmol photon/$m^2$/s) of a cave or other subterranean feature. It can include red and far-red light that occurs in heavily shaded environments. In some cases low light may also be considered up to 30 µmol photon/$m^2$/s.

The term "lumen" refers to the unit of luminous flux (lm).

The term "photoactivation" means the process of activating a substance by means of radiant energy and especially light. It refers to the activation or control of a chemical, chemical reaction, or organism by light; or the process of activating a substance by means of radiant energy and especially light such as by photocatalysis.

"Saccharification" refers to a process of converting complex carbohydrates into monomeric sugars, such as hexose and pentose. Saccharification enabled by lytic enzymes produced by microbes in subterranean habitats can yield glucose and xylose as metabolizable carbon to sustain microalgae under dark subterranean conditions.

"Monomeric sugars" are monosaccharides that can include glucose, mannose, galactose, xylose, and arabinose.

The term "feedstock" refers to nutritional material assimilated or metabolized by a cell.

The term "isoprenoid" or "terpenoid" or "terpene" or "derivatives of isoprenoids" refers to any molecule derived from the isoprenoid pathway with any number of 5-carbon isoprene units, including compounds that are monoterpenoids and their derivatives, such as carotenoids and xanthophylls. The isoprenoid pathway generates numerous commercially useful target compounds, with non-limiting examples such as pigments, terpenes, vitamins, fragrances, flavorings, solvents, steroids and hormones, lubricant additives, and insecticides. These in turn are used in products for food and beverages, perfumes, feed, cosmetics, and raw materials for chemicals, nutraceuticals, and pharmaceuticals.

The term "carotenoid" refers to a compound composed of a polyene backbone which condensed from five-carbon isoprene unit, "carotenoid" can be an acyclic, or one (monocyclic) or two and it can be terminated by cyclic end-groups of the number (bicyclic). The term "carotenoid" may include both carotenes and xanthophylls.

A "carotene" refers to a hydrocarbon carotenoid. "Xanthophylls" are oxygenated carotenoids. Modification of pyrophosphate and phosphate groups of isoprene derivatives include oxidations or cyclizations to yield acyclic, monocyclic and bicyclic terpenes including monoterpenes, diterpenes, tripterpenes, or sequiterpenes, etc.

The term "carotenoprotein" or "water-soluble carotenoids" refers to hydrophilic carotenoid substances that are complexes or to water-soluble carotenoid-protein complexes. The term "Orange carotenoid protein" or "OCP" refers to a water-soluble protein which plays a role in photoprotection in diverse cyanobacteria.

The term "emollient" refers to a preparation that softens the skin.

The term "phycobiliproteins" refers to microalgal pigments that appear red and blue and absorb in the visible light region of 450 to 650 nm. Phycoerythrin, a characteristic pigment in certain red algae, is located at the periphery of the phycobilisomes. Phycocyanin is located in the phycobilisomes between phycoerythrin and allophycocyanin (or at the periphery if phycoerythrin is absent). They are relatively unstable proteins and relatively expensive to produce.

The term "lipids" refers to any of a large group of organic compounds that are oily to the touch and insoluble in water. Lipids include fatty acids, oils, waxes, sterols, polar lipids, neutral lipids, phospholipids, and triglycerides. They are a source of stored energy and are a component of cell membranes. Phospholipids are a lipid containing a phosphate group in its molecule. They include diacylglyceride structures, e.g., phosphatidic acid (phosphatidate; PA), phosphatidylethanolamine (cephalin; PE), phosphatidylcholine (lecithin; PC), phosphatidylserine (PS), phosphosphingolipids, and glycerophospholipids. "PUFA" or "PUFAs" refers to lipids that are polyunsaturated fatty acids. Examples of PUFAs are docosahexaenoic acid (DHA, represented as 22:6 n-3); eicosapentaenoic acid (EPA, represented as 20:5 n-3); omega-3 docosapentaenoic acid (DPA n-3, represented as 22:5 n-3); omega-6 arachidonic acid (ARA, represented as 20:4 n-6); and omega-6 docosapentaenoic acid (DPA n-6, represented as 22:5 n-6).

The term "microorganism" or "microbe" refers to microscopic unicellular organisms, including microalgae, which can also be filamentous or colonial. The microorganisms usable in the fermentation according to the present invention can include mutants, naturally occurring strains selected for a specific characteristic, or genetically engineered variants of a naturally occurring strain.

The term "microalgae" refers to a eukaryotic microorganism that contains a chloroplast, and optionally is photosynthetic, or a prokaryotic microorganism capable of being photosynthetic. Microalgae include obligate photoautotrophs, which are incapable of metabolizing a fixed carbon source as energy, as well as obligate or facultative heterotrophs, which are capable of metabolizing a fixed carbon source. Microalgae as obligate heterotrophic microorganisms include those that have lost the ability of being photosynthetic and may or may not possess a chloroplast or chloroplast remnant. Microalgae can divide to produce populations of cells and can be scaled-up or enter a production phase to produce biomass, and this process can be continued indefinitely until a maximum productivity is achieved.

The term "prokaryote" or "prokaryotic" refers to cells lacking a membrane bound nucleus, mitochondria, or any other membrane-bound organelles.

The term "subaerial" means "existing, occurring, or formed in the open air or on the earth's surface, not underwater or underground." Subaerial algae are terrestrial algae that live on stable exposed surfaces above the soil (Nienow 1996).

The term "subterranean" means subsurface; existing, situated, or operating below the surface of the ground; underground; pertaining to underground environments; subterraneous. Subterranean sites, regions, features, or systems may include one or more of lava tube, cave, tunnel, fissure, crevasse, chasm, grotto, cavern, mesocavern, or fumarole; this includes in karst and pseudokarst. A "subterranean microalga" includes a microalga present at the interface between the surface and subterranean environments under low light, such as the entry zone of a cave. A subterranean microalga can be present in such subsurface sites, regions, features, or systems in micro or macro scale; this includes in subterranean karst and volcanic habitats. It is understood that a subsurface microbiome, biosphere or habitat with a microalga can be formed from igneous, sedimentary, metamorphic, and other rock types.

The term "karst" refers to a geology formed from rocks such as limestone, dolomite, gypsum, and quartzite from the processes of dissolution of soluble rocks or by erosion.

The term "volcanic" means relating to or produced by a volcano or volcanoes.

The term "cave" means a natural cavity in rock, generally large enough to be entered by people. "Cave" can also refer to a much smaller opening such as sea cave, rock shelter and grotto. The term "cavern" means a large chamber within a cave. The term "cavernicolous" refers to living in caverns or caves.

The term "entrance zone" refers to the interface between surface and subterranean environments, usually of a cave. An entrance zone leads into the twilight zone.

The term "twilight zone" refers to the part of a cave in which some daylight penetrates (but not direct sun light) and gradually diminishes to no measurable photosynthetically active radiation of the dark zone.

The term "transition zone" refers to an initial region of the dark zone beyond the twilight zone where there is no visible light. But some external factors from the entrance environment may still be apparent, e.g., seasonally fluctuating air temperatures.

The term "dark zone" refers to the part of a cave in perpetual darkness, which lies beyond the twilight zone. The dark zone generally begins at the point at which there was no measurable photosynthetically active radiation (<0.1 µmol photon/m$^2$/s).

The term "pseudokarst" refers to a geology similar to karst with caves and dolines but formed in non-soluble rocks, from the processes of melting of permafrost or ground ice, collapse after mining, and by outflow of volcanic lava to form cryokarst, thermokarst, and volcanic features of lava tubes (tunnels), lava caves and associated fissures, crevices etc.

The term "mesocavern" is defined as all cavities in rock smaller than 20 cm in diameter and larger than 0.1 cm in diameter.

The term "microcavern" is defined as all cavities in rock that are smaller than 0.1 cm in diameter down to and including microscopic size. Though not considered a cave, such cavities may serve as valuable biological niche sites.

The term "macrocavern" includes all cavities in rocks greater than 20 cm in diameter. This includes all the cave passages that are accessible to people.

The term "fissure" means an open crack in rock or soil. A "crevasse" or "chasm" is a deep open crack. Tectonics can cause fissures, as well as cavities, crevices as such.

The term "fumarole" means an opening in the ground, often in areas surrounding volcanoes, which emits steam and gases. Fumaroles may occur along tiny cracks or long fissures and on the surfaces of lava flows and of deposits of rock from volcanic activity. A fumarole field is a region of gas vents or thermal springs where magma or hot igneous rocks at shallow depth release gases or interact with groundwater.

The term "microclimate" refers to the climate (temperature, humidity, air movement etc.) of a restricted space, such as of a cave, or of a portion of a cave.

The term "microhabitat" refers to habitat or the microenvironment in which an organism lives that is of small or limited extent and which differs in character from some surrounding more extensive habitat.

The term "microbiome" means the microorganisms in a particular environment.

The term "endolithic" and "endolith" in the context of the invention refers to a microorganism (archaeon, bacterium, fungus, lichen, algae or amoeba) that lives inside subterranean rock or in the pores between mineral grains of a subterranean rock.

The term "siliceous" refers to rocks that are sedimentary rocks with forms of silica ($SiO_2$) as the principal constituent. The most common siliceous rock is fine-grained chert; other types include diatomite, which can itself include diatomaceous chert.

The term "diatomaceous earth" or "diatomite" refers to a collection of diatom shells or exoskeletons found in the earth's crust. They are soft, silica-containing sedimentary rocks which are easily crumbled into a fine powder, and typically have a particle size of 10 to 200 µm. Those used in skin care products typically are 10 µm or less.

The term "ecotope" refers to the ecological habitat on the scale of individual organisms sharing space.

The term "cenomanian rock" refers to a hard, crystalline dolomite or hard dolomitic limestone of red, dark gray or yellow color.

The term "doline" refers to a closed depression draining underground in karst, formed by solution and or collapse of underlying rock strata. Its form is variable, but often conical or bowl shaped.

The term "exudate" refers to a substance secreted from microalgae.

The term "mucilage" means a viscous or gelatinous substance. This can include mucopolysaccharides.

The term "capsule" refers to a polysaccharide layer that lies outside the cell envelope (of a bacterium, part of the outer envelope) or cell wall (of a eukaryote) and is thus deemed part of the cell. The capsule is a gelatinous polymer made up of either polysaccharide or polypeptide or both.

The term "sheath" refers to a secreted, tubular structure formed around a chain of cells or around a bundle of filaments. Cells within a sheath may or may not subsequently separate from the sheath.

The term "chemolithoautotrophic" refers to organisms that obtain the necessary carbon for metabolic processes from carbon dioxide in their environment. They also use inorganic compounds such as nitrogen, iron, or sulfur for the energy to power these processes.

The term "chasmoendolithophyte" refers to organisms that inhabit rock crevices (crevasses) or are found in volcanic fumarolic soils. A subterranean alga or cyanobacterium can be chasmoendolithophytic, meaning having a habitat in rock crevices. It can be an oligotroph organism that can live in an environment that offers very low levels of nutrients. *Pseudococcomyxa* is an example of a chasmoendolithophyte.

The term "humic substances (humic)" refers to biogenic substances produced from biodegradation of tissues. Humic is a form of organic matter of complex composition including many different acids possessing carboxyl and phenolate groups as well as complexed minerals, vitamins and micronutrients.

The term "chlorophototrophic bacteria" or "chlorophototroph" refers to bacteria that use bacteriochlorophylls and/or chlorophylls to produce energy for growth. Chlorophototrophs are grouped in seven phyla: Cyanobacteria, Acidobacteria, Proteobacteria, Chlorobi, Chloroflexi, Firmicutes, and Gemmatimonadetes.

The term "chlorophyte" refers to any of the green alga that makes up the division *Chlorophyta*. They can be associated with both karst and pseudokarst features. Non-limiting examples include members of the *Chlorellales, Chlorophyceae, Chlamydomonadales, Chlorococcales, Sphaeropleales, Trebouxiaphyceae,* and *Trebouxiales*.

The term "cyanobacteria" refers to a group of photosynthetic bacteria, some of which fix nitrogen. Some live in a wide variety of moist soils and water either freely or in a symbiotic relationship with plants or lichen-forming fungi. Cyanobacteria also can be associated with both karst and pseudokarst features. They range from unicellular to filamentous and include colonial species. Belonging to the *Cyanoprokaryota*, non-limiting examples include members of the *Cyanophyceae, Chroococcales, Oscillatoriales,* and *Nostocales*.

The term "coccolithophore" refers to a microbe that produces an exoskeleton shell containing plates called coccoliths, commonly calcareous plates with crystals of calcium carbonate that can scatter light.

The term Xanthophyta (synonym Ochrophyta) refers to a taxonomic division that includes members of the Xanthophyceae and Michococcales.

The term "diatom" refers to microbes that produce an exoskeleton shell that contains forms of silica. They are members of the *Bacillariophyta*. They can be associated with both karst and pseudokarst features. Non-limiting examples include *Achnanthes, Achnanthidium, Anomoeoneis, Aulacoseira, Brachysira, Cyclotella, Cymbella, Diadesmis, Eolimna, Encyonema, Epithemia, Fragilaria, Gomphonema, Halamphora, Hantzschia, Humidophila, Luticola, Melosira, Navicula, Nitzschia, Orthoseira, Pinnularia, Planothidium, Sellaphora, Stauroneis, Staurosira,* and *Ulnaria*.

The term "exoskeleton," in the context of a microalgal cell, refers accumulated minerals and metals that produce an external shell outside the microalgal cell.

The term "sunscreen composition" refers to a cream, lotion, spray, gel, lipstick or other topical composition, comprising at least one sunscreen active ingredient typically used for UV protection of the skin. The term "sunscreen active" or "sunscreen active ingredient" or simply "sunscreen" is a molecule added to a sunscreen composition to screen UV light and protect the skin. As sunscreens are intended for the absorption of UV light, they are also called "UV actives" or "UV-filters". For sunscreen labeling purposes, "UV protection" is a definition for protection capability against the full UV spectra including UVA, UVB and UVC. A sunscreen active ingredient may protect against one or more types of UV radiation. This may occur by several types of mechanisms, including by blocking or absorbing the radiation, any resulting excess energy, or quenching free radical molecules that form.

The term "nitrogen fixation" or "to fix atmospheric nitrogen" means to convert inorganic $N_2$ to organic nitrogen.

The term "purifying a cell" or "purifying a cell away from" refers to removal of all or a substantial portion of the culture medium used to cultivate the cell. In a multicellular culture this process leaves a concentrated cellular biomass.

The term "glycopolymer" means a biologically produced molecule comprising at least two monosaccharides. Examples of glycopolymers include glycosylated proteins, polysaccharides, oligosaccharides, and disaccharides.

The term "extracellular matrix" or "ECM" of normal skin refers to a gel-like matrix comprised of a variety of polysaccharides, water and collagen proteins which give the skin elasticity and compressibility. These properties are due to the combined presence of fibrous structural proteins (including collagens, elastin and laminin) that provide ECM resilience; and proteoglycans (including dermatan sulfate and hyaluronan) that are large, hydrated molecules that help plump and cushion cells in the skin.

The term "vehicle" or "delivery system," in the context of topical products or drugs related to dermatology (cosmetic or dermopharmaceutical), refers to the carrier, delivery system, or means by which an active substance is formulated. The vehicle can help with spreadability or penetration (absorption) into the skin. In some cases, the vehicle occurs naturally in skin, such as glycerin. In some cases, the vehicle is a liposome or nanoemulsion. Other examples of delivery systems include, without limitation, liposomes, mixed liposomes, oleosomes, niosomes, ethosomes, milliparticles, microparticles, nanoparticles and solid lipid nanoparticles, nanostructured lipid supports, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as microemulsions and nanoemulsions, which can be added to achieve a greater penetration of substance and/or to improve the pharmacokinetic and pharmacodynamic properties of it. A vehicle can be a moisture-retentive topical dressing.

The term "vehicle or "delivery system" further relates to an additive, diluent, adjuvant, or excipient with which the substance produced according to the methods of the invention can be administered. Depending on the hydrophilic or hydrophobic nature of the substance and its intended application and administration, and the preferred form of the delivery system for the substance of the invention, a person skilled in the art understands that these carriers can be liquids, such as water, oils or surfactants, including those of petroleum, animal, plant or synthetic origin, such as and not restricted to botanical oils (from nuts, seeds), mineral oil, polysorbates, sorbitan esters, ether sulfates, sulfates, betaines, glycosides, maltosides, fatty alcohols, nonoxynols, poloxamers, polyoxyethylenes, polyethylene glycols, dextrose, and digitonin.

The present invention relates to methods of producing substances by culturing under low to no light conditions microalgae obtained from a subterranean habitat for at least a portion of their production cycle and optionally, under conditions of low nutrients or presence of light for at least a portion of their production cycle. The invention provides that subterranean microalgae harbor unique compounds and compositions of industrial value; that the microalgae products can be produced at industrial scale and reasonable cost; and that they can comprise compositions for personal health and care.

Representative products produced according to the instant methods include cellular exudates (secretion), constituents of the microalgal cell, and whole cells. One type of product can be biogenic substances, for example, from a cell secretion. Additionally, microalgal products produced according to the methods of the instant invention can be a part of a biotic or abiotic complex. A biotic complex can be association with a biological substance, such as a protein. An abiotic complex can be associated with a non-biological material.

The invention also provides that the species found in subterranean habitats, when produced as biomass can be used in health and personal care. Certain non-limiting examples of such products include micro-abrasive powder, non-extracted colorant, exoskeleton of the microalgae, or a reflective mineral powder comprising exoskeleton of the microalgae as shells emptied of their cellular contents.

Further examples of products produced according to the instant methods include sugar polymers in the form of capsular exopolysaccharide, extracted or non-extracted pigment, colorless isoprenoids, or extracted colorant.

Additional products produced according to the instant methods include carotenes, carotenoids (including xanthophylls), fatty acids (lipids), polysaccharides, and whole cell powders.

This invention specifically concerns high volume accumulation of subterranean microalgal capsular exopolysaccharides with distinct and useful physiochemical properties suited for use in industry. These can be produced at industrial scale by the methods of the invention.

The invention provides that the capsular exopolysaccharides from subterranean microalgae and associated methods of production are suited for use in multiple (topical and ingestible) formulations and applications. For use as an ingredient in cosmetics, a saccharide isomerate can be produced by the methods of the invention. Certain embodiments of the invention use the saccharide isomerate from *Parachlorella* capsular exopolysaccharide to produce compositions for face cream, face serum, and for lip care.

The invention further provides that the yield of capsular exopolysaccharides ranging from 50% to 70% of the dried cell weight and unique to the species can be produced according to the methods of the invention.

In a specific embodiment, a purified exopolysaccharide is provided obtained from the capsule of an alga belonging to the genus *Parachlorella*. Preferably, an algae belonging to the genus *Parachlorella* is *Parachlorella kessleri* var. *volcanica* ATCC Patent Deposit #PTA-125105 (also identified herein as KAS1543).

Using the methods of the present invention it was discovered that a composition comprising exopolysaccharides and at least one protein imparts desirable advantage to the composition. A new proteoglycan thus created endows the complex with functionality beyond its individual properties. One functionality is hydration with elevated antioxidant property. Another is as a stabilized protein with skin moisturizing property, such as for wound healing.

Also disclosed herein are methods of producing the first known instance of color-stable water-soluble carotenoids by culturing algae belonging to the genus *Haematococcus* under specific changes in culture conditions and in complete darkness.

Certain embodiments of the invention also produce a composition comprising a cosmetically acceptable vehicle and a water-soluble carotenoid extracted from a *Haematococcus* spp., for example, *Haematococcus pluvialis*. Such compositions can be administered to a subject's skin in methods of protecting the subject's skin from UV and blue light, oxidative stress, and free radicals, and can be associated with anti-aging, rejuvenating, or other benefits.

The disclosure provides that the organisms obtained from subterranean habitats when cultivated under initial darkness in the presence of a mixture of biogenic substances and minerals supplied in certain amounts are surprisingly induced to produce unique compounds and chemistries, substantially increased yield, altered exoskeleton yield and composition, and pigment accumulation in dark fermentation; notably under changes in culture conditions of low or high nutrition, or low or high light conditions, including under monochromatic light.

Microalgal habitability of subterranean habitats, especially under low to no light conditions, is heavily influenced by metabolites and byproducts of other colonizing microbes, geochemical gradients such as metal, carbonate, or dissolved oxygen concentrations, water availability, and by the development of rock permeability over time. Permeation enables introduction into the subsurface system of nutritive or otherwise stimulating organic compounds and minerals from the surface.

An embodiment of the invention provides for producing microalgal substances from microalgae obtained from volcanic subterranean habitats. These habitats commonly feature basaltic lava, with varying amounts of silicon dioxide ($SiO_2$), aluminum ($Al_2O_3$), iron (FeO), calcium (CaO), magnesium (MgO), sodium (NazO), titanium ($TiO_2$), potassium ($K_2O$), and phosphorus ($P_2O_5$). Mineral deposits also include manganese, sulfur, nickel, calcium carbonate, amorphous silica, and trace elements such as molybdenum, zinc, copper, and cobalt. Through metamorphism, weathering and the like these elements can be present in various forms and associations. Together these can nutrify microflora and influence their phenotypes. The latter can include distinctive morphologies and compositions such as frustules of diatoms via biomineralization.

Another embodiment of the invention provides for producing substances from microalgae present in karst subterranean habitats. Most karst caves and other subterranean features form through limestone bedrock. Limestone is a sedimentary rock with grainy materials of the minerals calcite and aragonite (different from crystalline forms of calcium carbonate, $CaCO_3$). The solubility of limestone in water and solutions of weak acids leads to karst landscapes. Limestone often contains variable amounts of silica (as chert) or siliceous skeletal fragments, and varying amounts of silt, sand, and clay. Travertine is a form of limestone that does not consist of grains but is formed by chemical precipitation. Secondary calcite may be deposited by saturated (supersaturated) surface water that precipitates the material in caves to form stalagmites and stalactites. Another form of calcite is oolitic limestone, which appears granular.

A further embodiment of the invention provides for producing substances from subterranean microalgae present on moist surfaces and in pooled standing water on the cave floor, in rock crevices or divots. Surface water infiltrating the caves or other subterranean feature is the prime source of hydration, minerals, and organic nutrients. The water can be in the form of a drip line from the cave ceiling or seepage and rivulets along walls. Water can also enter along roots that have penetrated the subsurface. FIG. 1 illustrates non-limiting sites where microalgae are present for practicing the method of the invention to produce microalgal substances.

Algal assemblages also occur in a dry habitat, with little to no water infiltration, including under seasonal wet or dry conditions, such that the sites in FIG. 1 apply to both wet and dry habitats. In addition, transition dark zones in caves and lava tubes can have moving air that aids in desiccation of regions of the cave environment. An embodiment of the invention provides for a mucilaginous microalgal species that resists desiccation.

In some embodiments, the culture medium contains one or more compounds that are industrially equivalent to those found in biogenic substances such as generated by microflora or those delivered to subterranean ecologies by penetrating roots or other infiltrating water. Plant roots of several different species can penetrate through igneous, sedimentary and metamorphic rock (Bashan et al. 2006; Howarth et al. 2007). In Hawaii, among the first plants to colonize lava flows are the *palapalai fern* (*Microlepia strigosa*) that have mycorrhizal fungi. These create mycelium to aid establishment of the 'ohia lehua tree (*Metrosideros polymorpha*) whose roots penetrate through lava. Mycorrhizal fungi arrive soon after the volcanic substrates cool. The 'ohia lehua roots in turn help colonization of subterranean microbes.

In some embodiments, the culture medium contains minerals such as those delivered to subterranean ecologies by penetrating roots or other infiltrating or percolating water. Natural biogeochemical cycles and processes can dictate the specific composition of available minerals in a specific locale of volcanic or karst geology and influence the subterranean flora. Weathering of rocks including by microorganisms can play an essential role in maintaining a continuous supply of inorganic nutrients.

In some embodiments applying the biomimetic principal of drip-fed nutrients and supplemented as necessary (such as adding alkalinity) yields conditions favorable to cell division. In some embodiments applying the biomimetic principal of drip-fed nutrients and supplemented as necessary yields desired algal substances.

Roots act as conduits, whereby minerals (biogenic or inorganic), cations, organic acids and such are transferred from terrestrial to subterranean ecosystems. Plants, associated or incidental microflora and animal urine/guano contribute the organic matter and minerals present and bioavailable in the water chemistry. This includes, but is not limited to, $Ca^{2+}$, $K^+$, $Mg^{2+}$, $PO4^3$, $SO4^{2-}$, $NO_3^-$, $NH_4^+$, $HCO_3^-$, $Cl^-$, $Fe_2^+$, $Fe_3^+$, Fe-oxides, Si-oxides (including amorphous silica), and organic and inorganic carbon and nitrogen. In some embodiments the organic carbon is organic acid with carboxylic substituents. In certain embodiments the organic acid is acetic acid. In certain embodiments, the organic acid is propionic acid, citric acid, fumaric acid, glycolic acid, lactic acid, malic acid, pyruvic acid, succinic acid, glucuronic acid, galacturonic acid, humic, or ferulic acid. In certain embodiments the nitrogen is in the form of urea.

In some embodiments the organic carbon is a hexose sugar such as glucose, representative of monomeric sugars produced by the action of microflora including actinomycetes present in subterranean ecosystems.

Accordingly, the method of the present invention provides nutrition for a microalgal cell with components that mimic—as identical or functionally equivalent to—what is present in subterranean habitats. In some embodiments, a biomimetic culture medium contains one or more components of nitrogen (ammonia, nitrites and nitrates, and/or urea); phosphorus; sulfur; carbon (carbonate, monomeric sugars, and/or organic acids as referenced above and elsewhere in this disclosure); minerals (as referenced above); and water. It is understood that commercial sources of the equivalent compounds may be used for industrial scale production.

In some embodiments the nitrogen is in the form of $NaNO_3$; $NH_4Cl$; or $CO(NH_2)_2$ (urea). In some cases, yeast extract is one convenient commercial nitrogen source. In some embodiments the phosphate is in the form of $KH_2PO_4$ or $NaH_2PO_4·H_2O$. In some embodiments the elements are in the forms of $KH_2PO_4$; $MgCl_2$; $FeCl_3$; $ZnCl_2$ or $ZnSO_4·7H_2O$; $H_3BO_3$; $CoCl_2·6H_2O$; $CuC_2·2H_2O$ or $CuSO_4 \cdot 5H_2O$; $MnCl_2 \cdot 4H_2O$; and $Na_2MoO_4 \cdot 2H_2O$ or $(NH_4)_6 Mo_7O_{24} \cdot 4H_2O$. Tap water can naturally contain $H_4SiO_4$. In one embodiment titanium and silicon are additionally supplied. In some embodiments the carbon for industrial scale production is in the form of acetic acid or glucose.

The method of the invention provides that useful substances are produced by microalgae nourished by mimicking the delivery of phosphates, sulfates, metal oxides, carbonates, organic acids, ammoniacal or nitrate nitrogen through driplines in complete darkness and constant temperatures. By mimicking subterranean driplines, one or more of the nutrients is supplied in increments over time. Further, the supply is discontinuous, but the effect providing continuous or sustainable nourishment over time.

In some embodiments, exposure to agitation results in a planktonic suspension rather than a mat. A mat is the normal mode of growth for mucilaginous microbes such as diatoms.

In several embodiments, the cultivation conditions mimic aerobic conditions through aeration using agitation and a supply of air to keep dissolved oxygen above levels for conditions favorable to cell division.

The present invention describes subterranean microalgae species that under conditions of low nutrition display phenotypes of interest that can be useful as products. Conversely, the present invention describes that subterranean algae exposed to rich nutrition conditions manifest unexpected phenotypes for products of interest. An embodiment of the invention provides for nutrition to be delivered using a simulation of the cave nutrient delivery system. One embodiment mimics a drip line. One embodiment of enriched nutrition results from cultivation using compounds naturally present in the subterranean ecology delivered in a biomimetic manner in volumes sufficient to produce a desired algal substance.

Different regions or zones of a subterranean feature can have different physical and physicochemical conditions and ecologies. A given region of a cave, lava tube and the like can be characterized by constant or consistent ecological conditions. An embodiment of the invention provides for conditions that mimic a constant or consistent ecology. One embodiment provides for cultivation that mimics one or more conditions of no light or low light; air flow and circulation and composition; and temperature. Conditions can include absence of seasonality or occurrence of flowing water. In one embodiment a cultivation condition is under no light or low light at, or less than, about 30 μmol photons/$m^2$/s. In one embodiment a cultivation condition is between 5-55° C.

A consistent subterranean ecology can be one in which growth occurs in conditions with consistent fluctuations in one or more parameters. For example, conditions may fluctuate between 5-95% relative humidity (RH); between 0.0001-0.64 μmol photons/$m^2$/s. Other conditions may fluctuate between 0.0008-0.06 μmol photons/$m^2$/s, between 0.06-1 μmol photons/$m^2$/s, and between 1-30 μmol photons/$m^2$/s. Consistent temperature fluctuations may be between 5 and 18° C., between 18 and 24° C., between 24 and 35° C., between 35 and 55° C. It is recognized that subterranean species can be present in other dissimilar subterranean conditions of RH and temperature such as found at arctic or polar regions, deserts, and volcanically active regions.

In one embodiment a cultivation condition is under red light. These light conditions mimic those in a cave, crevasse, chasm or other subterranean features depending on its depth or distance from the surface or cave mouth. In one embodiment a cultivation condition is under green light. The cultivation condition is sustained over time, indicating suitability for industrial scale up.

In some embodiments, a microalga is able to form pigment substances, both photosynthetic and accessory despite originating as a subterranean heterotroph and restricted to dark cultivation mimicking the cave environment. These pigments are considered vital antioxidants and free radical scavengers to provide protection against effects of harmful UV and other wavelength irradiation, and thus are prized for topical application to skin, lip, and hair.

In some embodiments, subterranean species receiving subsequent exposure to a terrestrial environment (such as higher light) unexpectedly produce additional or modified algal bioproducts of value. Notably, when low density cultures-typical of subterranean population with nominal nutrition—are exposed to a relatively high differential in light in the transition from total darkness into daylight, the effects are even more pronounced.

In one embodiment the subterranean alga produces UV radiation protective substances. In another embodiment an alga produces substances that counteract the damage possible from compounds that form after exposure to UV radiation. UV light (100-315 nm) damages DNA and proteins. Exposure to broad spectrum UV light can cause skin erythema (sunburn) and reactive oxygen species (ROS) are produced that can lead to inflammation, skin aging and health issues. Protection against these harmful stresses in microbes is induced and achieved in a light-dependent manner (Schumacher 2017). A mechanism to protect against damage is the production of metabolites, frequently secondary metabolites, that absorb UV light and convert it into heat (sunscreens) and/or that exhibit antioxidant activities. Well-known biogenic sunscreen compounds include carotenoids, xanthophylls, carotenoid-precursor isoprenoids, melanins, and mycosporines, and UV-absorbing mycosporine-like amino acids.

Cyanobacteria have also developed mechanisms to optimize light harvesting when diffuse, low-light conditions limit growth, and to provide photoprotection with protection from excess excitation energy and singlet oxygen free radicals. One mechanism is the production of Orange Carotenoid Protein (OCP), a type of carotenoprotein. Cyanobacterial OCP requires photoactivation by strong blue-green light for its photoprotective quenching function. This is difficult as an industrial process, including the requirement of sufficient high light exposure for very high cell density cultures.

One exemplification of this invention describes for the first time how a eukaryotic microalga unexpectedly produces a natural hydrophilic carotenoid substance when cultivated in complete darkness. In one embodiment its production is industrially scalable.

In one embodiment the hydrophilic carotenoid substance is carotenoprotein that can comprise one or more astaxanthin, lutein, zeaxanthin, doradexanthin, and canthaxanthin moieties.

In another embodiment the carotenoprotein is produced under complete darkness and low levels of nutrients. In one embodiment the source organism is *Haematococcus*.

In one embodiment the carotenoprotein is highly water soluble. This feature expands the range of product compatibility for the antioxidant carotenoids compared to traditional carotenoids that are oil soluble.

In one embodiment a composition with the carotenoid substance solubilized in water includes 1% phenoxyethanol as preservative. In one embodiment, a composition provides for a facial spray-mist. In one embodiment a composition with the carotenoid substance solubilized in water is adjusted to pH 7 with boric acid and preserved with an ophthalmic preservative. In one embodiment a composition with the carotenoid substance solubilized in water provides reduction in UV irradiation.

In one embodiment a water-soluble carotenoid product is obtained at 2.9 g product per liter per hour over 6 days for a culture with a final density of 17.4 g/L algae.

In some embodiments, natural (non-recombinant) water-soluble carotenoprotein is produced at large scale by Chlorophytes in complete darkness.

In one embodiment, subterranean microalgae cultivation proceeds under no light followed by photoactivation or "light stress." Remarkably, there is an acceleration of features for a subterranean alga compared to a similar species from a terrestrial (photosynthetic, autotrophic) ecosystem. Light-associated activation can arise from the change from darkness to exposure to photosynthetically active radiation or to UV light, blue light, red light or green light, including under just low photon flux. In some embodiments, a substance is produced under low photon flux.

In one embodiment, subterranean species grown by the methods of this invention and receiving subsequent exposure to a terrestrial environmental condition unexpectedly produce additional or modified algal substances of value. This can be manifested when relatively low-density cultures (through low nutrient delivery or by dilution) are exposed to the light differential in the transition from total darkness or low light into daylight, whereby the effects become pronounced. In one embodiment a substantial capsular exopolysaccharide substance is produced. In one embodiment, astaxanthin from *Pseudospongiococcum* is produced.

In some embodiments the carotenoid substance of interest, which can be colorless or colored and can be a carotenoid-precursor molecule, is produced under total darkness. Using the method of this invention, subterranean algae are identified as substantial carotenoid producers.

In some embodiments the carotenoid is fucoxanthin. In one embodiment the source organism is *Eolimna*. In one embodiment the source organism is *Sellaphora*. In another embodiment the source organism is KAS1537. In one embodiment, a composition provides for fucoxanthin in a face oil or oil-gel.

In one embodiment the carotenoid-precursor molecule is the colorless phytoene and phytofluene. In one embodiment the source organism is *Haematococcus*. In one embodiment the algal culture starts at a density of 2 g/L algae dry weight and reaches 32 g/L after 96 hours.

In one embodiment the pigment is lutein. In one embodiment the source organism is de-encapsulated *Parachlorella*. In another embodiment, the source organism is *Pseudococcomyxa*. In some embodiments, a composition provides for lutein in a face oil or oil-gel.

Some embodiments of the invention provide a cultivation condition under a light-associated stress. Subterranean cyanobacterial isolates can be cultivated under a narrowed light spectrum as may be found in a cave entrance behind substantive hanging gardens. In one embodiment, cyanobacteria are cultivated photoautotrophically under only far-red light.

In another embodiment, a eukaryotic microalga is first cultivated in complete darkness and then provided with exposure to light. In one embodiment, a eukaryotic alga produces astaxanthin. In one embodiment the source organism is *Pseudospongiococcum protococcoides*. In one embodiment it yields at least 0.45% astaxanthin content. In another embodiment the subterranean alga is *Coelastrella* sp. In yet another embodiment the subterranean alga is *Scenedesmus armatus*. In some embodiments the light exposure is to low light. In other embodiments the light exposure is to moderate to high light.

In another embodiment, a cyanobacterial microalga is *Oculatella*, which produces phycoerythrin in low light or red light. The cyanobacterial microalga can also be a heterotrophic *Anabaena*, which produces mycosporine and mycosporine-like amino acids. In one embodiment, a composition provides for phycoerythrin for lip care. In other embodiments, the mycosporine and mycosporine-like amino acids are used in compositions for face serum, facial spray-mist, and cream or lotion.

Certain embodiments of the invention also disclose methods for cell cultivation, nutrient medium that mimic a subterranean environment for cell culture; heterotrophic growth; fermentors, dewatering, extraction, substance decolorization; and substance purification.

While a microalgal cell resident in a subterranean ecology in complete darkness is anticipated to remain viable within the habitat due to some protective mechanisms such as encystment or secretion of exopolysaccharide (EPS), or even some heterotrophic capability, their ability to survive outside of the habitat, to reproduce at a rapid pace that allows industrialization, and to produce a substance of value are all uncertain. To produce sufficient substance of interest at a commercial scale, cells are preferably cultured in large quantities. The culturing may be in large liquid volumes, for example in suspension cultures. Other examples include starting with a small culture of cells which expand into a large biomass in combination with cell growth and propagation as well as substance production. Other examples include large biomass production independent of subsequent substance production. Bioreactors or steel fermentors can be used to accommodate large culture volumes. A fermentor similar those used by beer breweries is suitable, as are extremely large fermentors used in the production of cell line-derived pharmaceuticals or ethanol.

Heterotrophic growth conditions fundamentally differ from photosynthetic growth of microalgae. In one embodiment a microalga grown as a heterotrophic culture produces cell lines, substances, and quantities that unexpectedly differ from what is seen for a phototrophic culture of the same organism, or for a species of the same taxon.

A fermentor can be used to allow cells to undergo the various phases of their growth cycle. As an example, an inoculum of subterranean cells can be introduced into a medium followed by a lag period (lag phase) before the cells begin growth. Under cultivation conditions that need to be pre-determined for each subterranean algal cell line, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells. The production of the substance of interest also needs to be determined and optimized, be it taking place during the various phases of the growth cycle, or thereafter. In some embodiments the substance production takes place under introduced light, which can be low light less than 20 µmol photons/m$^2$/s or higher light greater than 20 µmol photons/m$^2$/s, or it can be within a narrow wavelength of light such as red or green or even under UV irradiation for periods measured in minutes or in days.

A purified substance can also be stabilized and formulated as a composition. In some embodiments, pH is adjusted with a citric acid/sodium citric system. Alpha-tocopherol can also be used to stabilize pigments. Phenoxyethanol can be used as a preservative. A composition can be in a carrier or solvent system.

In general, the taxonomic diversity of subterranean microalgae decreases from the entrance to the end of the cave under increasing darkness stress. In limestone caves for example, the frequency of coccoid forms of cyanobacteria (such as *Chroococcales*) decreases and filamentous (such as Oscillatoriales) increases into the inner cave. For cave systems with constant high humidity, the intensity of light governs cyanobacterial distribution rather than the availability of drippings (for example see Vinogradova et al. 1998). For karst limestone, dolomite, and dolomitic limestone, subterranean ecotopes are identified depending on the softer substrate (white crystalline limestone and stalagmites) or the darker colored and harder dolomite or hard dolomitic limestone. Thus, the geological structure of the substratum also affects the composition of algal communities, in addition to illumination and moisture.

This trend of microflora being governed by light intensity, water availability, and geological structure is paralleled in pseudokarst of volcanic caves. Among eukaryotic algae species, inner subterranean systems of low to no light are dominated by diatoms, followed by the *Chlorophyta*; representatives of the Xanthophyta are commonly absent. The extent of diversity of diatoms depends to a large extent on the presence of additional moisture.

Herein are disclosed subterranean cyanobacteria of the taxon *Cyanoprokaryota*, including non-heterocystous and heterocystous filamentous cyanobacteria. The examples are non-limiting, as it is understood that subterranean systems, with their ranges of dimensions and ecologies may feature any number of cyanobacterial species, both unicellular and filamentous. It is not unusual for example for a subterranean system to have from 1 to 50 or more species representing 1 to 20 or more genera within the system.

In several embodiments, the microalgae flora is obtained for cultivation from a stable cave climate with constant temperatures and relative humidity from both limestone and lava geologies. It is understood that the microalga flora can be numerous and diverse and that the examples provided are non-limiting for algal substances that can be produced from the flora under the methods of the present invention.

As an example of the range of diversity within a subterranean habitat, the diverse microalgal flora of a stable limestone cave system (constant temperatures range from 24° C. to 32° C., constant relative humidity is 64% to 76%) from the entrance to deep in the cave, is comprised of 69 species from *Cyanoprokaryota* (45), *Chlorophyta* (15), *Bacillariophyta* (7), and Xanthophyta (2) belonging to five classes, 10 orders, 25 families, and 45 genera. Cyanobacteria outnumber the other taxa at all locations. Among eukaryotic microalgae orders, *Pennales* (*Bacillariophyta*) and *Trebouxiales* (*Chlorophyta*) lead in species diversity (10% each). The genus *Chroococcus* (six species) ranks first in species diversity. The most common species were *Chroococcus varius* (49%), *Mychonastes homosphaera* (23.5%), *Nostoc linckia* f. *terrestris* (21.5%), and *Chlorella vulgaris* (15.7%) (Vinogradova et al. (2009), incorporated by reference herein).

In one embodiment, a subterranean cyanobacterial substance is produced by the method of this invention. In one embodiment, the cyanobacterium is *Anabaena variablis* (Nostocaceae). In another embodiment the cyanobacterium is *Oculatella* (Oscillatoriales). *Oulatella* is a red filamentous non-heterocystous cyanobacteria well known to form biofilms on calcareous surfaces in illuminated *hypogea* and catacombs of Rome and Malta, where RH is constantly above 90%, temperatures fluctuate seasonally between 17 and 21 C, with extreme low light less than 10 μmol photons/m²/s (Zammit et al. 2012).

Generally speaking, photosynthetic cyanobacteria are well known to acclimate to various light conditions. Cyanobacteria contain colored, water-soluble phycobiliproteins as part of their phycobilisomes (PBS), the major light-harvesting pigment-protein antenna complexes. The phycobiliproteins include phycoerythrin (Amax 560 nm), phycoerythrocyanin ($\lambda_{max}$ 575 nm), phycocyanin ($\lambda_{max}$ 620 nm), and allophycocyanin ($\lambda_{max}$ 650 nm). As reviewed in Gan (2015), some cyanobacteria undergo Complementary Chromatic Acclimation (CCA) under exposure to green light or red light, with alterations of the phycobilisomes so that they absorb light complementary to the incident radiation. In green light, phycoerythrin is featured and cells appear brownish. In red light, phycoerythrin may be replaced to varying extents by phycocyanin to maximize light harvesting, and cells appear blue-green. Phycoerythrin is a major light-harvesting pigment of red cyanobacteria such as *Oculatella*. It is widely used as a fluorescent probe and analytical reagent; could be valued in excess of $10,000 per kg. Phycobiliproteins are also used as colorants in food (chewing gums, dairy products, sherbets, etc.) and cosmetics such as lipstick and eyeliners in Asia.

Cyanobacteria can also perform non-photochemical quenching using the water-soluble orange carotenoid protein (OCP) to protect against high light and harmful reactive oxygen species. Specifically, it can directly scavenge singlet oxygen (1O2). In cyanobacteria, OCP binds a ketocarotenoid (hydroxyechinenone, hECN). Under strong blue-green illumination, OCP gets photoconverted from an orange inactive form (OCPo) to a red active one (OCPr). OCPr interacts with the phycobilisomes, and triggers heat dissipation of the excess light energy. OCPr binds to phycobilisome cores that contain allophycocyanin proteins.

In one embodiment, a subterranean microalgal substance produced by the method of this invention is a hydrophilic carotenoid substance from *Haematococcus*. Despite being water-soluble and affiliated with ketocarotenoids, the hydrophilic carotenoid substance of the present invention is distinct from any reported OCP or OCP-like carotenoprotein extract due to its color stability between dark or illumination storage, formation under complete darkness, and induction after a nutritional change during cultivation. In one embodiment the carotenoprotein substance is produced by a eukaryotic microalga. Large scale production of a hydrophilic carotenoid substance by a eukaryotic microalga for industrial applications is novel and for the first time discovered to be possible by the methods of this invention.

Herein are disclosed subterranean eukaryotic microalgae of the taxa *Cyanoprokaryota, Chlorophyta, Bacillariophyta, Xanthophyta*, and *Charophyta*. This can include, but is not limited to, members of the genera *Anabaena, Parachlorella, Desmodesmus, Scenedesmus, Monoraphidium, Coelastrella, Chlorella, Coccomyxa* (synonym *Pseudococcomyxa*), *Klebsormidium, Haematococcus* (synonym *Sphaerella*), *Hantzschia, Aulacoseira, Nitzschia, Navicula, Humidophila* (synonym *Diadesmis*), *Eolimna*, and *Sellaphora, Chamaepinnularia, Oculatella, Geissleria*, or *Navigolum*. Other subterranean diatom flora is reviewed in Falasco et al. 2014, which is incorporated herein by reference in its entirety.

Several additional non-limiting products and applications are exemplified.

A. Products—Cell Secretions that are Polysaccharides.

One embodiment of the invention provides for microalgal substances that are polysaccharides, specifically exopolysaccharides. Microalgal exopolysaccharides (EPS) are reviewed in Delattre et al. (2016). EPSs are thought to play a role in protection of the cell against desiccation, osmotic stress, harmful compounds in the environment, and/or to enable adherence to sold surfaces such as a biofilm. Microalgal polysaccharides are increasingly recognized for health and therapeutic applications (such as antiviral, antioxidant, anti-inflammatory, and immunomodulatory); and in skin and scalp/hair care applications.

One embodiment of the present invention concerns production of capsular exopolysaccharides from the microalgae genus *Parachlorella*. This genus may produce heteropolysaccharides that may remain bound externally on the cell, in form of a capsule, and that also may be released into surrounding culture broth. U.S. Pat. Nos. 8,927,522, 8,277, 849, and Japanese Pat. 6174219 describe isolating *Parachlorella* EPS solubilized in culture media (i.e., released polysaccharides) from which cells have been previously removed; purification of capsular EPS is not described.

In one embodiment of the present invention, the capsular exopolysaccharides are released from the microalgal cells by use of heat. Previously it was thought that the process of heating microalgae to boiling (100° C. and above) generally destroys algal cells and releases undesirable intracellular, lower weight polysaccharides and contaminants. These may be non-hydrating or lack the smooth feel desired for various applications. In one embodiment, the release of capsular EPS uses heat at 100° C. for at least 10 minutes. In one embodiment, the release of capsular EPS uses heat at 121° C. for at least 10 minutes. In some embodiments, the capsular EPS that is released by heat treatment exceeding 100° C. or even 121° C. surprisingly yields hydrating EPS that also produced a smooth skin feel. Heat treatment can be longer than 10 minutes, such as 20 minutes or 30 minutes and hydrating properties increase with increased duration of heating and capsular release. The cells are not lysed in this process. Usually the shortest processing time that gives the best performance is selected. In the case of heating to release the capsule and to provide good hydrating properties, assessment of whether there is a benefit to proceed longer than 30 minutes can be determined empirically by a skilled artisan.

In some embodiments of this invention, the capsular exopolysaccharides are produced under dark heterotrophic conditions followed by optional light exposure. The aforementioned patents U.S. Pat. No. 8,927,522, 8,277,849B2, JP6174219B2, as well as EP2754710A1 describe a cultivation of *Parachlorella* that is restricted to dark heterotrophy prior to purification of EPS present in the culture medium from which the cells have been removed. U.S. Pat. No. 8,927,522 states that making light available to the cells is unnecessary when using the methods of the invention. EP2754710A1 teaches away from autotrophic cultivation in the light, stating that heterotrophic cultivation in the dark is superior for higher yields of *Parachlorella* EPS obtained per a volume of a culture broth.

One embodiment of this invention shows very high-volume accumulation of capsular exopolysaccharides from *Parachlorella*. For comparison with released, non-capsular exopolysaccharide yields, EP2754710A1 describes that the yield of EPS released into the culture broth is proportional to the cell density of the culture, measured as a dry weight basis, with a maximum reported value of 17% (with cells at 93 g/L). To clarify, this is the amount of dried EPS harvested from the culture broth relative to the dried cell weight. In contrast, using the methods of the present invention, the capsular cell-bound EPS comprises 50% or more of the *Parachlorella* biomass weight in dark heterotrophic cultivation, and 60%, and 70% or more of the *Parachlorella* biomass weight in an optional added light cultivation (herein referred to as light- or photo-activation) for the subterranean algal species disclosed in the invention.

In some embodiments, a 35 g/L cell culture can produce 21 g/L EPS, or a 15 g/L culture can produce 9 g/L EPS at 60% EPS per weight biomass.

A further embodiment provides the insight that capsular exopolysaccharides produced under dark heterotrophic conditions or low light exposure are distinct in composition or performance from those produced under heterotrophic conditions followed by optional low light or higher light exposure, herein referred to as light- or photo-activation of the EPS.

In some embodiments, the microalga species is exemplified by genus *Parachlorella* (Chlorellaceae), specifically KAS1543 *Parachlorella kessleri* var. *volcanica* ATCC Patent Deposit #PTA-125105. Accession KAS1543 shows 99.85% (1335/1337 matches, 0 gaps) similarity with the 18s rRNA region of *Parachlorella kessleri* (FM205846.1).

Figure 3:
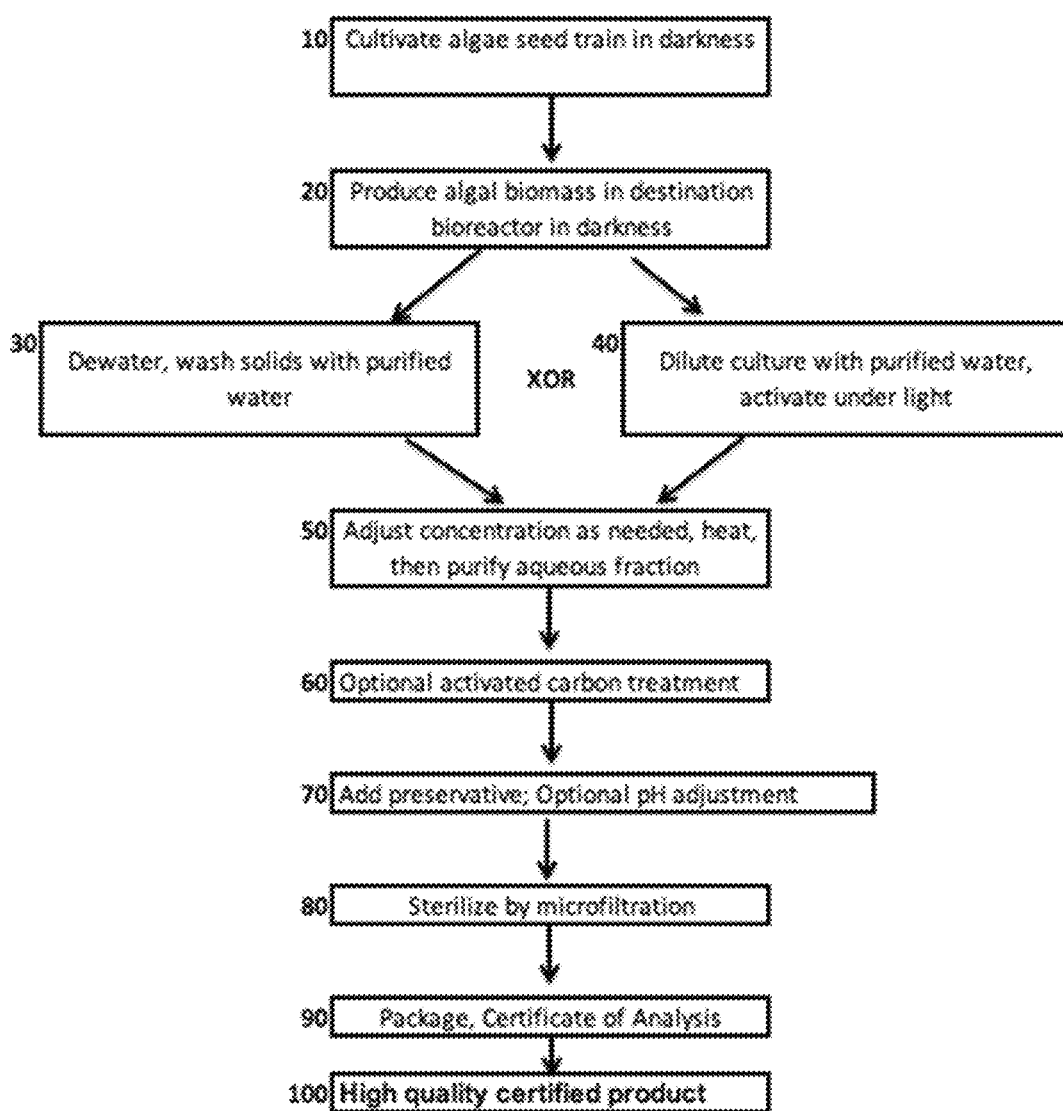
FIG. 3. General manufacturing flow for saccharide isomerate from capsular exopolysaccharide obtained from subterranean microalgae species using the "lava tube method" of dark fermentation.

In one non-limiting example, a method of producing an exopolysaccharide is provided wherein the method comprises culturing cells of the genus *Parachlorella* in complete darkness (FIG. 3 steps 10 and 20); concentrating cells from culture media; heat treating to release capsular exopolysaccharide (FIG. 3 step 30); and separating the exopolysaccharide from particulate contaminants (FIG. 3 step 30); and then adding preservative and purifying the capsular exopolysaccharide to sterility. (FIG. 3 steps 70 and 80) before packaging and certifying the high quality product (FIG. 3 steps 90 and 100). The method includes a change in culture conditions of nutrition, specifically a nitrogen limitation, implemented between in step 20 after biomass is produced in darkness before dewatering in step 30 or before added light of step 40, to induce substantial amounts of capsular exopolysaccharide.

In one embodiment the composition of capsular polysaccharide surrounding the cell includes rhamnose, xylose, and glucuronic acid. In one embodiment the glycosidic linkages of the structure are defined.

In another embodiment, the exopolysaccharide produced by the strain of KAS1543 *Parachlorella kessleri* var. *Volcanica* contains a natural sulfation. Another embodiment shows distinct and useful physiochemical properties of the capsular exopolysaccharides from *Parachlorella*.

Some embodiments of the invention provide the insight that the capsular exopolysaccharides produced by the method of the invention are suited for use in multiple topical and ingestible formulations and applications. These can include cosmetic and pharmaceutical compositions for the treatment or care of one or more of skin, hair, nails or mucous membranes. It is understood that applications for use in humans can cross over to use in animals as well.

In some embodiments the capsular exopolysaccharide is Saccharide Isomerate, a name recognized by the International Nomenclature of Cosmetic Ingredients (INCI) system of names for ingredients of cosmetics. The components of saccharide isomerate include carbohydrates naturally present in the stratum corneum of skin, wherein it can bind to free amino groups such as of lysine in the keratin of the stratum corneum. As such it provides long-lasting moisturization as a humectant and emollient and cannot be washed off easily. In one embodiment, due to the capsular exopolysaccharide being a water-binding agent, it is also effective in dry frizzy hair, dry scalp and in low humidity. Dry weight values for compounds listed under the INCI name of Saccharide Isomerate are not comparable. For example, a mixture of plant-derived monosaccharides glucose and fructose lacks the molecular weight, structure, uronic acids, sulfation, branching, isomers, furanose derivatives, esters, glycosidic linkages, etc. It is understood that individually and taken together these characteristics can provide unique physicochemical properties for an EPS.

The use of EPS can also address another concern surrounding the use of proteins that are widely used in research and as pharmaceutical agents, wherein retaining their stability and activity are primary concerns for storage and subsequent use. In some embodiments the EPS is a protein stabilizing agent.

In another instance of the invention, a protein is linked to the EPS to comprise a composition that is a technofunctional EPS. In some embodiments the EPS substance produced by the method of the invention is naturally low in proteins and suited to interacting with one or more types of proteins to produce a proteoglycan.

A major "contaminant" reported in water extracted EPS are proteins. These are removed in the EPS purification process, as described in U.S. Pat. No. 8,927,522. Remarkably, using the methods of the present invention it is discovered that the very ability for proteins to be covalently linked to the polysaccharide structure as contaminants could turn a negative property into a desirable property for various applications. Microalgal EPS has been used in various compositions described in the trade, with the composition comprising EPS and other components, none of which is a protein. Use of proteins in leave-on cosmetic applications can be problematic due to stability and degradation issues; generally, when proteins are used they are those found in the skin such as collagen. Further, creation of proteoglycans is not previously described.

A new proteoglycan thusly created by the methods of the present invention endows the EPS with functionality beyond its primary properties such as hydration (moisturizing, humectant and skin feel performance); or endows the protein with stability or performance not otherwise present.

In one instance this is a water-soluble pigmented protein. In one embodiment this includes a phycobiliprotein such as from red algae or cyanobacteria, which is sensitive to heat and light, and stable only for short time periods.

In another instance this is an intrinsically disordered protein (IDP). In one embodiment the EPS substance produced by the method of the invention is naturally low in proteins and with high water holding capacity. These traits lead to good interactions with IDP. In one embodiment the IDP is a collagen for application in wound healing. In one embodiment the EPS can serve as a cosmetically acceptable topical carrier for formulation with an effective amount of skin proteins in the form of a hydrogel. Lysate of cultured skin cells, for example cultured human fetal skin cells comprising human fetal skin cell proteins, can be used in a hydrogel for topical compositions to treat skin conditions, as described in U.S. Pat. No. 9,278,122.

Accordingly, another aspect of this invention relates to a cosmetic or dermopharmaceutical composition characterized in that it comprises a cosmetically or dermopharmaceutically effective quantity of the exopolysaccharide produced by a strain of *Parachlorella kessleri* and at least one cosmetically and/or dermopharmaceutically acceptable excipient and/or ingredient. In one embodiment the ingredient composition (w/w) is between 0.001% and 20%; and the use rate in a final formulation for topical application is between 0.01% and 100% (this includes an ingredient being solubilized directly in the capsular exopolysaccharide solution).

This invention provides an industrial scalable means for heterotrophically cultivating in a fermentor a subterranean species that produces exopolysaccharide; for producing and purifying high amounts of capsular EPS from a *Parachlorella* strain that exceed reported yields from culture broth produced by other *Parachlorella* strains; that increases the amount of the capsular exopolysaccharide without requiring a concurrent increase in cell density under an optional photoactivation period; that eliminates the use of organic solvents for purification and eliminates the need to dry the isolated EPS; and physiochemically alters the EPS into a more hydrating compound during a heat-mediated purification step. The purified EPS is suited to compositions for providing a smoothing and lubricating feeling on the skin, and which can be otherwise topically applied in cosmetic uses, such as a face makeup, or in lipstick or an eye shadow bases, or in controlling hair frizz, or restoring moisture to dry skin and scalp. The purified EPS is suited to compositions forming proteoglycans and otherwise stabilizing proteins for a variety of applications.

The present invention also relates to additional microalgal substances and products for formulation in health and personal care products as compositions of the disclosed invention. The invention thus provides highly desirable compositions that deliver high value cosmetic and dermopharmaceutical ingredients such as carotenoids, isoprenoids, phycocyanins, polyunsaturated fatty acids, moisturizing polysaccharides, carotenoproteins, and other components.

Not only does biomimetic-based large scale cultivation provide for algal growth, but some algal species present in subterranean habitats also perform better or produce novel substances or products. For example, capsular exopolysaccharides are shown to comprise over 50% to 70% of biomass weight, under oligotrophic conditions in which major nutrients are completely utilized (fully depleted) in the culture solutions. At least two features, namely yield capability and novel substance, are essential features that must be monitored to decide if a specific subterranean microalga warrants selection for industrialization.

B. Products—Cell Constituents that are Pigments: Fucoxanthin

There is a need for cosmetic products that inhibit darkening effects on skin and to provide an even skin tone and whitening; and to help inhibit skin damage caused by ultraviolet radiation both for cosmetic and health benefits (reduction of ROS, inflammation, cancer risk). Substances that inhibit the enzyme tyrosinase aid in addressing this need. Substances that are antioxidants also aid in addressing this need. Fucoxanthin ($C_{42}H_{58}O_6$), a xanthophyll carotenoid with unique chemical structure (an epoxide bond, an allenic bond, and a conjugated carbonyl group in the polyene chain), is such a substance of value. It is found as an accessory pigment in the chloroplasts of heterokonts, resulting in a brown or olive-green color. Fucoxanthin absorbs light primarily in the blue-green to yellow-green part of the spectrum with maxima at around 510-525 nm and absorbing significantly in the range of 450 to 540 nm.

In some embodiments, fucoxanthin is an extracted substance produced by the method of this invention. In some embodiments fucoxanthin is obtained from subterranean fresh water diatoms. In an embodiment the level of fucoxanthin is about 0.7 to 1.2% DW. This is over 70- to 100-fold higher than that of seaweed (about 0.01% fucoxanthin).

Seaweed (macroalgae) had been the standard source of fucoxanthin used in skin care products but it is an expensive and time-consuming process with large waste generation and limited amounts available in the market.

In some embodiments fucoxanthin is extracted with eicosapentaenoic acid (EPA) and docosahexaenoic acid (DHA) naturally present in the diatom by the method of the invention. In an embodiment this is combined with a hydrophobic carrier to form a skin-beneficial and health-beneficial composition. EPA and DHA are omega-3 fatty acids; EPA is a precursor molecule to DHA, a structural component of the cerebral cortex, skin, and retina.

C. Products—Metal Chelators

In one embodiment the substance of interest produced by the method of the present invention has metal chelation properties. While its immediate utility is as a benefit for skin, this attribute can be similarly applied to metals recovery from effluent or other waste or recycling materials; or for remediation purposes. For example, EPS of a marine strain *Parachlorella* sp. *binos* is being applied to decontaminate through assimilation the radioactive isotopes strontium and cesium from nuclear power plant waste (Shimura et al. 2012).

D. Products—Other Pigments, UV Ray Protectants and Antioxidants

There is a need for more skin care product options that provide protection from sun damage. Recent banning of sunscreens with harmful chemicals oxybenzone and octinoxate reduces the options for UV protection and exacerbates the long-felt need in the skin care and sunscreen industries for safe and effective UV-protective products. These existing sunscreen chemicals disrupt the symbiotic relationship between the coral and algae, leading the coral death. Excessive sun exposure is well known to damage skin, leading to degradation of the skin extracellular matrix and wrinkle formation, skin photoaging, dark spot formation, and development of skin cancers. Restrictions on use of sunscreens could lead to an increase in skin cancer, particularly melanoma.

Therefore, there is a need for new ingredients that could provide or boost the Sun Protection Factor (SPF) for the protection against UVB radiation and UVA Protection Factor (UVA-PF) for the protection against UVA radiation.

Biomineralization in one exemplification of this invention refers to the incorporation of photosensitive titanium dioxide ($TiO_2$) into the exoskeleton of diatoms that normally use silicon dioxide; exoskeletons are considered cell secretions. Marine diatoms can naturally contain titanium in the silica fraction, around 0.08% Ti; and titanium is also naturally present in lava tubes. During the formation of the siliceous shell (frustule), the silica is deposited as an organic-mineral hybrid material associated with nitrogenous compounds such as peptides are also secreted to guide the polycondensation of silicic acid as amorphous silicate. Water collected in a lava tube can have a high concentration of monosilicic acid, exceeding 400 M $H_4SiO_4$ (see Table 3 in Prouty et al. 2017).

One problem identified in Chauton (2015) is that the semi-conductive (photovoltaic) properties of $TiO_2$ nanoparticles in living cells causes toxicity in combination with UV light because the nanoparticles can lead to the formation of unstable reactive oxygen species. The present invention discloses that cultivation under cave conditions in the dark, protected from light, eliminates this issue for long term culture in industrial production and enables large scale production of titanium-enriched biomass and corresponding shell (exoskeleton) powders.

In one embodiment, Ti is incorporated together with Si in the new frustules of dividing diatoms. Furthermore, the large surface area and numerous pores on the frustules of certain lava tube species (preferably those 25 microns or greater in length), provides abundant nanoscale features to integrate the titanium dioxide. In one embodiment the subterranean diatom used to produce titanium-enriched biogenic powder is KAS1537.

This invention exemplifies the optical properties of biomineralized products that can contribute as to boosting the SPF and/or UVA-PF protection provided in sunscreens including in formulas applied under or over sunscreen. Amorphous silica in frustules is transparent to visible light but combined with $TiO_2$ or zinc oxide (ZnO) gains the ability to scatter light including UV radiation, contribute to iridescence, and whiten substances (opacity) as an additive.

In one embodiment a substance that is a mixture of the colorless isoprenoids, phytoene and phytofluene, is described.

In a preferred embodiment, a composition of a mixture of phytoene and phytofluene in a carrier oil is conducive to an improved UV protection by the composition. In a preferred embodiment the substance is a novel whole cell intact biomass for oral consumption, intended to confer benefits known for phytoene and phytofluene (reviewed in Meléndez-Martínez 2018).

Additionally, other carotenoid substances provide resistance to skin damage and skin aging by virtue of their antioxidant activity against free radicals and/or reduction of inflammation caused by a variety of insults to skin health as are known in the art.

In one embodiment, oil-soluble astaxanthin is produced by the method of the present invention. Humans rely on carotenoids as their primary source of antioxidants. The orange-red pigment astaxanthin (3,3'-dihydroxy-b, b'-carotene-4,4'-dione) is considered the most potent carotenoid in existence with numerous therapeutic applications and proven effectiveness in skin care products.

In one embodiment of the present invention, subterranean *Pseudospongiococcum protothecoides* (Chlorococcales, Chlorococcaceae) is disclosed to produce oil-soluble astaxanthin after a period of dark heterotrophic culture followed by light exposure under nutrient deficiency by the method of the present invention. In one embodiment, production of astaxanthin as a substance of value is separate from the production of biomass. In other embodiments, *Coelastrella* sp. and *Scenedesmus armatus* are disclosed to produce astaxanthin after a period of dark heterotrophic culture followed by light stress under nutrient deficiency by the method of the present invention.

Taiwanese Patent No. TWI491349 describes a species of aerial photoautotrophic *Coelastrella* that forms astaxanthin, adonirubin, lutein, canthaxanthin, ß-carotene in the light after one-month exposure to 150 µmol/m$^2$/s in narrow 1 L bottles. To accelerate reddening to 10 to 12 days, a culture is salt-stressed by 1.5% NaCl and 0.1% sodium bicarbonate, light is increased to 400 µmol/m$^2$/s. A different species, *Coelastrella rubescens*, is reported to reach densities during the green phase of 2×10$^7$ cells/mL to produce up to 2% DW total carotenoids of astaxanthin and canthaxanthin (and up to 50% DW lipids) under photosynthetic cultivation (Minyuk et al. 2017). *Coelastrella striolata* is reported to have a 0.30/day photosynthetic growth rate as calculated in the growth logarithmic phase- and forms 5.6% total secondary carotenoids, comprised of 4.7% canthaxanthin, 0.7% beta-carotene, 0.15% astaxanthin accumulate under in narrow tubes under 65 µmol/m$^2$/s at 25 C (Abe et al. 2007). It produced the pigments over 30 days, 10 of which occurred after reaching stationary phase in nitrogen-deficient medium. Aerial *Coelastrella* and *Scenedesmus* are known to accumulate carotenoids (Hanagata and Dubinsky 1999), notably under conditions of high light, nutrient stress, desiccation or high salt, but heterotrophic cultivation of subterranean species is not disclosed.

In another embodiment, hydrophilic carotenoid containing substances are produced by the method of this invention, as described above for carotenoproteins.

In another embodiment the xanthophyll lutein is produced by the method of the present invention, exemplified in one instance by *Coccomyxa* (*Pseudococcomyxa*). Among the antioxidant carotenoids that human eye retinal health depends upon, lutein is one of the most critical. For skin care, there is a need for filtration of blue light, including high energy visible blue light from solar radiation or artificial light from screens of electronic devices. Lutein can meet this need, with absorbance from about 420 to 520 nm.

Lutein is currently commercially obtained from the flower petals of a vascular plant (marigold), which results in a large volume of waste material that requires disposal. There is a need for heterotrophic carotenoid producers in outer space colonization planning, especially extremophiles that can tolerate challenging environments. The species is appealing for extraterrestrial lutein production due to its acid and heavy metals tolerance. Extraterrestrial caves (e.g., on Mars or the Moon) and lava tubes on Mars have been identified from orbit and are being considered to support colonization by Humans. As stated by Moreno 2010, while vascular plants would not be supported in these cave system habitats, heterotrophic or chemoautotrophic microbes would be.

In another embodiment, UV-absorbing mycosporine-like amino acids are produced by the method of this invention.

E. Products as Whole Cells-Colorants and Microabrasives.

In an embodiment a subterranean diatom grown by the method of this invention produces a rich brown hue as a heterotroph; if brought into the light a culture changes in cell pigment composition to become intensified in chlorophylls for a rich olive or moss hue useful as a cosmetic colorant. In one embodiment the coloration is delivered into a product using powdered whole cells of the diatom. In one embodiment the diatom is *Eolimna*.

F. Products-Lipids

In an embodiment, residual biomass consisting of de-encapsulated cells from stressed subterranean *Parachlorella*. One non-limiting exemplification describes KAS1543 *Parachlorella kessleri* var. *volcanica* ATCC Patent Deposit #PTA-125105 to illustrate a remarkable lipid content of 87%, consisting of dermally desirable fatty acids.

The following examples are provided to describe the invention in further detail. These examples serve as illustrations and are not intended to limit the invention.

Example 1-Establishment of Heterotrophic Subterranean Strains and Cultures

This example is directed to identifying heterotrophic cell types that are cultivated under conditions favorable to vegetative growth and making a product of interest using the methods of the invention. Herein described are non-limiting sample collection sites for subterranean microalgae. Samples are collected from 500-year old pseudokarst formations, from volcanic rock crevasses, and from within the entry to transition dark zones of lava tubes at about 3300 to 4000 ft elevation, 19°N and 155° W, near the east and northeast rim of the Kilauea caldera of Hawaii. Other samples are obtained from limestone karst and volcanic pseudokarst formations at about 21° N and 157°W from 300 to 1000 ft elevation within the Kona ahupua'a and Manoa 'ili division on Oahu, in the Hawaiian Islands. In complete darkness inside a cave, white deposits of calcium carbonate, calcium sulfate dihydrate, or amorphous silica are seen on the ceiling and walls adjacent to some collection sites. Additionally, pale orange to yellowish coloration is present, indicative of iron oxides, fulvic acids, and humic acids and such leaching into the cave from overlying strata. Some colored slime is presumably due to bacterial microbiota.

Microbiome samples are collected from within the entry zone through to the transition dark zone of caves, as scrapings from rock walls, as dripwater direct from the roots or from the water and rocky bottom of standing water puddled in cavities; as well as from rock substratum of mesocavern and crevasses. Site temperatures inside a cave are constant, varying narrowly from about 18° C. to 24° C. In the substantial caves, tree roots protruding from above into the cave void act as drip lines that can introduce microbes and nourishment. Leachate is heard dripping in a steady but discontinuous flow, and rivulets are visible along walls and protrusions when illuminated for observation. The ecologies are considered freshwater. FIG. 1 describes collection points in a subterranean habitat.

Once environmental samples are obtained from a subterranean habitat, they are stored in the original collection containers (sterile plastic tubes, plastic baggies, or bottles for drippings, rock scrapings and root tissues collected with sterilized droppers and forceps) at room temperature in darkness or in low light as a mixture of microbes (prokaryotic and eukaryotic). Portions are dilution-plated within a few days after collection on sterile solid 1% f/2 agar medium prepared as freshwater using tap water; particulate samples are rinsed vigorously in sterile water or medium prior to decanting for plating. f/2 medium is half-strength of "f medium" (Guillard and Ryther 1962) with the original ferric Sequestrene substituted by 3.15 g/L $FeCl_3 \cdot 6H_2O$ and 4.36 g/L $Na_2EDTA \cdot 2H_2O$ and omission of seawater and silicate. Plates are incubated at 21-24° C., 12:12 light/dark period with a photon flux density of 10 $\mu mol/m^2/s$ for several weeks. Plates are regularly screened using a dissecting light microscope, and algal colonies picked from a plate are suspended in liquid medium for observation with an Olympus IX-2 SP inverted light microscope at 1000× magnification and imaged using an Olympus U-CMAD3 camera. For scanning electron microscopy (SEM), a few thousand actively growing cells are washed three times with distilled water to remove salt for electron microscopy and were then spotted onto a 47 mm 0.45 µm nylon membrane (Supelco Nylon 66 Membrane #58067) and air dried overnight. Specimens are mounted on aluminum stubs and sputter coated with gold/palladium in a Hummer 6.2 sputter coater. Specimens are viewed with a Hitachi S-4800 Field Emission Scanning Electron Microscope at an accelerating voltage of 5 kV.

Next, single colonies are subcultured onto antibiotic medium or further dilution plated until unialgal or unialgal and axenic cultures are obtained (Guillard, 2005). Cyanobacteria are selectively isolated when the medium was supplemented with 100 mg/ml of DCMU (diuron, N-3, 4-dichlorophenyl-N9-dimetil urea). Initial taxonomic grouping was determined in part by microscopy (light or electron) with reference to a taxonomic literature known in the art, before proceeding to molecular fingerprinting.

Molecular identification was based on 18S rRNA or 16s rRNA sequence. Monocultures were grown in 50 to 125 ml flasks on gyratory shakers to active growth, usually within 5-7 days. Species were identified by DNA fingerprinting of the microbial samples or unialgal isolates. DNA was extracted from 1-5 mg of freeze-dried monoculture biomass using E.Z.N.A Plant DNA Kit (Omega Bio-Tek, D3485-02) following the manufacturer's instructions for the Plant DNA mini kit short protocol. PCR amplification was performed in a BioRad ICycler thermocycler using appropriate primer sets for the 18s rRNA region. One of two universal sets of primers for 18s rRNA were used to amplify DNA from eukaryotic algae: 18s rRNA set 1: AACCTCGTT-GATCCTGCCAGT (SEQ ID NO: 1) and GATCCTTCTGCAGGTTCACCTAC (SEQ ID NO: 2) or 18s rRNA set 2: AAGATTAAGCCATGCATGTC (SEQ ID NO: 3) and GCGGTGTGTACAAAGGGCAG (SEQ ID NO: 4). 18s rRNA set 1 yielded a slightly larger region compared to 18s rRNA set 2. One universal set of 16s rRNA primers were used to amplify DNA from cyanobacteria: TAGCTGGTCTGAGAGGATGA (SEQ ID NO: 5) and TACCTTGTTACGACTTCACC (SEQ ID NO: 6). Other primer sets used are described in specific examples below. DNA sequence reactions were performed on the PCR products by the Advanced Studies in Genomics, Proteomics, and Bioinformatics (ASGPB) at the University of Hawaii at Manoa, Honolulu, Hawaii. Isolates were classified based on identity matches for sequences with >99.5% from comparative BLAST searches with GenBank entries; genus level names are adopted for 99.5% or lower matches or if the GenBank accession is only designated at the genus level.

Example 2-Heterotrophic Media Compositions and Biomass Production

This example describes cultivation of subterranean microalgae under heterotrophic conditions, including under biomimetic conditions. This is termed the "lava tube process" or "lava tube method." An isolated alga was treated in initial culture as both an obligate species and a facultative heterotroph. Cave environment was recreated through set temperatures in consistent darkness; intermittent drip feed similar to subsurface leachate delivering organic acids and other nutrients; oxygenation (as dissolved oxygen) above some minimum; and set humidity. Liquid culture medium was preferred for ease of industrial scale-up; humidity was considered constant for a submerged culture. To determine the subterranean microalga's preferred forms of carbon (e.g., organic acids, hexoses, pentoses as might be found in a cave) and nitrogen (nitrate, ammonium, urea as might be found in a cave), stationary flask cultures were diluted 1:100 into 2 mL f/2 based mineral medium with different carbon and nitrogen sources in unagitated 24-well plates. Cultures were incubated in illuminated (mixotrophic) or dark (heterotrophic) incubators at 28° C. Growth of select axenic strains over 2 days in f/2 medium with appropriate carbon (10 mM) and nitrogen (1.76 mM) source was monitored in triplicate daily using a plate reader (Biotek Synergy) to read at OD750 nm and algal cell counts were taken on a hemocytometer at the outset and conclusion of the screens. Optionally, yeast extract can be utilized in the f/2 medium as an industrially convenient form of nitrogen and vitamin B complex.

Heterotrophic or mixotrophic base medium for growth of subterranean algae generally comprises water, carbon, minerals, and vitamins. Variations in absolute quantities and proportions can be optimized to a group of species, to a species, and eventually if needed to a strain. Absolute concentrations can vary with the inoculum concentrations. One base medium consisted of 10 mM carbon, 1.76 mM nitrogen, 0.05 g/L magnesium sulfate heptahydrate, 0.05 g/L calcium chloride dihydrate, 0.02 g/L potassium phosphate monobasic, 0.01 g/L iron-EDTA, 0.0063 g/L iron chloride hexahydrate, 22 mg/L tetrasodium EDTA, 0.3 mg/L cobalt sulfate, 6 mg/L manganese sulfate, 0.8 mg/L zinc sulfate, 0.2 mg/L copper sulfate, 0.7 mg/L ammonium molybdate, 0.4 mg/L boric acid, and B vitamins (e.g., 0.4 mg/L thiamine hydrochloride, 2 µg/L biotin, and 2 µg/L vitamin B12). *Parachlorella kessleri* and *Haematococcus* spp. used sodium acetate, acetic acid, and urea as carbon and nitrogen sources. *Scenedesmus* species used glucose and ammonium. Diatoms used glucose and nitrate along with sodium meta-silicate as silicone source. A base growth medium for cyanobacteria was Zarrouk's medium or BG11 with appropriate carbon and nitrogen sources.

For certain members of the Chlorophyte such as *Pseudospongiococcum, Coelastrella, Scenedesmus*, or some *Chlorella* a base medium consisted of 10 g/L glucose, 1 g/L yeast extract or ammonium equivalent, 0.7 g/L potassium phosphate dibasic, 0.3 g/L potassium phosphate monobasic, 0.3 g/L magnesium sulfate heptahydrate, 25 mg/L calcium chloride dihydrate, 3 mg/L iron sulfate heptahydrate, 0.36 mg/L manganese chloride tetrahydrate, 0.044 mg/L zinc sulfate heptahydrate, 0.02 mg/L cobalt chloride hexahydrate, 0.0196 mg/L copper sulfate pentahydrate, 0.0126 mg/L sodium molybdate dihydrate, 2 mg/L thiamine hydrochloride, 2 µg/L biotin, and 2 µg/L vitamin B12. This was employed in the "lava tube process." The fermentation proceeded for the first 18 hours with starting inoculum density of 0.27 g/L, temperature maintained at 26° C., pH 6.2, agitation/gas flow cascade >50% DO. Thereafter, drip-fed fermentation was performed from 18 hr to 72 hr. The nutrient feeds were at high concentrations calculated for the total number of feeds needed for the whole drip-fed fermentation period. Nutrient A was made up of all the base medium components except glucose and yeast extract. Nutrient A components were 23 times more concentrated than the base medium. Nutrient B was made up of 282.35 g/L glucose and 36 g/L Yeast extract. Nutrient A was fed every hour at 2.5 ml per feed starting at $18^{th}$ hr to 72 hrs. Nutrient B was fed every half hour from $18^{th}$ hr to $24^{th}$ hr at 12.5 ml per feed then every hour thereafter until the $43^{rd}$ hr at the same feeding volume; from $43^{rd}$ hr to $72^{nd}$ hr, it was fed every 2 hrs at the same feeding volume. After 72 hrs, feeding was stopped, and cells were harvested at a preferred time, depending on target substance to be produced. For example, the entire run can go to 120 hours or 140 hours. The biomass yield was 15-20 g/L DW. In some instances, a photo-finishing step (>30 µmol photon/m$^2$/s, 6500 K light for 24 for 48 hours) of the culture was added before harvest to elicit production of a substance not produced while in the "cave phase" of cultivation.

Next, the seed train from flask in base medium proceeded to larger culture volumes such as an intermediate fermentor or directly to the final destination reactor. Nutrients were supplied in an intermittent mode mimicking nutrition in the cave environment. One detailed example is provided for *Parachlorella*. Microalgal cells grown in 500 mL to 1 L volumes in 1 L and 2 L flasks, respectively, totaling 2.5 L culture, were transferred to 90 L of fermentor heterotrophic growth medium (same as flask heterotrophic medium) in a 100 L fermentation vessel (Eppendorf BioFlo 610) with an initial biomass density of 5 mg/L. The 90 L fermentation culture was incubated at 28° C. with gas exchange provided by 40 L/min sparged air and a pitched blade impeller at 100 to 350 rpm at pH 7.5. Using BioCommand Software, peristaltic pumps, and head plate ports the pH was maintained at pH 7.5 to 7.2 throughout the duration of the fed-batch fermentation with pH-triggered additions of 25% acetic acid supplied at 5% pump speed. A nutrient concentrate to support increasing cell densities (71 g/L urea, 34 g/L potassium phosphate monobasic, 18 g/L potassium sulfate, 25.5 g/L magnesium sulfate heptahydrate, 9 g/L iron-EDTA, 1.4 g/L thiamine hydrochloride, 112 mg/L biotin, 9 mg/L vitamin B12) and an antifoam/micronutrients/calcium concentrate (10% antifoam C solution Sigma A8011, 11 g/L tetrasodium EDTA, 0.15 g/L cobalt sulfate, 3 g/L manganese sulfate, 0.4 g/L zinc sulfate, 0.1 g/L copper sulfate, 0.25 g/L ammonium molybdate, 0.2 g/L boric acid, 40 g/L calcium chloride dihydrate) are frequently supplied (every 12 hrs, then increasing to 1.5 hours as the density increases) at 20% pump speed throughout the fermentation to control foam (hours 0 to 120) and to keep nutrient levels (hours 0 to 72) near starting concentration of fermentor heterotrophic growth media. Dissolved oxygen is maintained above 90% by increasing the amount of sparged air into the vessel up to 50 L/min and agitation up to 350 rpm. By this method the resulting biomass (13 g/L from an initial 0.005 g/L) was produced over 120 hours that included no lag phase and a 120-hour extended logarithmic phase of high specific growth of 1.57/day. The use of these components was advantageous over current practices by the physiology of rapidly growing cells; culture pH shifted from nitrogen metabolism were managed by addition of organic acid, doubling as the carbon source, to balance the culture pH without adding extra salt to the medium. Samples (10 mL) were collected every 24 hours for dry weight analysis to determine specific growth rate.

For subterranean diatoms, a 1.5 L culture was grown in a fermentor at 28° C. using gas flows of 1.0 to 2.0 LPM and agitation at 150-350 rpm with a Rushton impeller. Initial cell density was 0.05 g/L in a base medium containing 1.76 mM $KNO_3$ and 1 mM sodium metasilicate with other nutrients in proportion with the nutrient concentrates used to feed the culture below. A nutrient concentrate supported increasing cell densities and maintained nitrogen around 1.76 mM (101 g/L potassium nitrate, 12 g/L potassium phosphate monobasic, 25.75 g/L magnesium sulfate heptahydrate, 2.1 g/L iron-EDTA, 1.4 g/L thiamine hydrochloride, 112 mg/L biotin, 9 mg/L vitamin B12) along with an antifoam/micronutrients/calcium concentrate (10% antifoam C solution Sigma A8011, 11 g/L tetrasodium EDTA, 0.15 g/L cobalt sulfate, 3 g/L manganese sulfate, 0.4 g/L zinc sulfate, 0.1 g/L copper sulfate, 0.25 g/L ammonium molybdate, 0.2 g/L boric acid, 40 g/L calcium chloride dihydrate). Additionally, a sodium metasilicate stock at 122 g/L (Fisher AC419590025) was frequently added to maintain concentration around 1 mM to provide silica for growth, and pH of the culture was maintained at 8.0 using 0.15 M $H_3PO_4$. A 1 M glucose stock was also added as needed to maintain 5 to 10 g/L glucose in the culture for a carbon source. A culture was run for 120 hours.

Depending on the specific strain, the starting cell density, and the target product, the culturing is conducted for a period of some hours (it can be around 8 hours for example or less than one day) to several days, or even to a few weeks (for example to about 21 days).

Example 3-Bioactivity Assays and Analytical Methods

Several bioactivity assays or other analytical methods are used in characterization of algal substances. Other assays and methods are specified in further examples below.

Moisturizing Assay.

A substance is tested in different batches and concentrations, with and without an optional vehicle, in multiple combinations, to determine moisturizing properties and use rate of a concentrated product. In some cases, the vehicle is glycerin. Skin moisture is measured in a test region from the inner wrist to inner forearm with a SkinGuard 1.0 analyzer (LIUMY, Shenzen, China). Changes in moisture content over time are determined after application of substance on dry skin: 10 µl of sample is spread on the center of the test area three times for a total 30 µl applied. Moisture at the start and in 10-minute intervals to complete a 30-minute period is measured and recorded. Results are expressed as % moisture; a normal skin moisture value of the wrist is 45-50% and of the back of hand is 40-60%. Dry skin is around 25-29% moisture. The increase is an indication of the ability of a substance to restore skin's moisture to normal or near-normal values. Thus, repeated applications on dry skin can fully restore and maintain normal skin moisture. Moisturizing and hydrating is identified with restoring, rejuvenating, and protecting skin. General appearance and feel (shiny, matte, film, rapid absorbance, softening, soothing, smoothing, etc.) is also observed after application.

Tyrosinase Inhibition Assay.

Tyrosinase is responsible for the biosynthesis of the skin pigment melanin. Inhibiting the enzyme inhibits the formation of melanin, and therefore causes whitening of the skin. The demand for cosmetic ingredients with skin whitening properties is growing globally especially in Asia. It is therefore advantageous to find natural ingredients with anti-tyrosinase properties. Tyrosinase inhibition activity is determined using mushroom tyrosinase (Sigma-Aldrich, T3824) and L-tyrosine (Sigma-Aldrich, 93829) as is known in the art (Rangkadilok et al. 2007) for absorbance at 475 nm, measured using a Biotek Synergy HTX microplate reader.

Sulfuric Acid Method for Polysaccharide Quantification.

Polysaccharides are quantified using sulfuric acid to generate furfural groups for reading absorbance at 315 nm. The 1 mg/ml Extract (333 µL) was mixed with 1 mL of concentrated sulfuric acid, absorbance was read at 315 nm. Polysaccharides were determined using an equation generated by readings from a standard curve of known concentrations of glucose. The detection limit of the assay was 7.5 µg/mL (7.5 mg/g or 0.75%). Total amount of carbohydrates can be determined by the phenol-sulfuric acid method of Dubois (Dubois et al. (1956) per Delattre 2016).

Metals Analysis.

Metals testing employs Inductively Coupled Plasma Mass Spectrometry (ICP/MS). Solutions are filtered through 0.22-µm syringe filters into metal-free 15-ml centrifuge tubes. Diatom frustules intended for silica and titanium content analyses are rinsed in nitric acid and then dissolved in concentrated hydrofluoric acid prior to ICP-MS analysis following Chauton et al. (2015).

C-Phycocyanin (C-PC) Concentration and Stability.

The absorbance of each sample is measured at 620 and 652 nm. The C-phycocyanin (CPC), allophycocyanin (APC), and total phycocyanin concentration of the solution are calculated as is known in the art (Chaiklahan et al. 2012). For assessing thermal stability following Chaiklahan et al. (2012), samples are tested using a Bio-Rad ICycler thermocycler in 0.2 ml tubes at 65° C. or other desired temperature for 30 minutes. All samples are incubated in the dark, and absorbances read using a spectrophotometer.

Carotenoid Xanthophyll Concentration.

Pigments are extracted from freeze-dried biomass ground with mortar and pestle in 250 µL of acetone per mg of biomass for 5 minutes at room temperature. Crude extract (equivalent to 100 µg of original biomass) is run on a TLC plate (Sigma Z122777) in a running buffer of hexane:acetone (3:1) in a TLC chamber for 8 minutes. Major bands are cut out and pigments are solubilized in 600 µL of acetone and spun down at 14,000 rpm for 2 minutes; 500 µL are used obtain an absorbance reading at 476 nm using a BioRad Smart Spec. The exception is fucoxanthin, which is read at 470 nm. A standard curve is generated to convert absorbance into an amount of pigment on a dry weight basis. Other measurements (such as for colorless pigment precursors) are described in specific examples. The method of determining pigment concentration values by spectrophotometric readings was previously calibrated to HPLC readings to ensure accuracy.

Phenol Concentration and Stability in Presence of Biogenic Substances

The property of photocatalytic decomposition of phenol under UV light irradiation is used to assess the effect of a substance on phenol stability over time. Absorbance is measured at A269 with a UV-Vis Bio-Rad SmartSpec spectrophotometer at the start and then after 2 hr. Phenol is prepared as a 0.531 mM solution. Titanium (IV) oxide nanopowder (Aldrich Chemistry, ≥99.5%, 21 mm particle size) prepared at 2.5 mg into 40 ml phenol results in 2.2% conversion (decomposition) after 2 hr.

Ion Analysis

The ions associated with capsule exopolysaccharide (EPS) were identified by the Water Resource Research Center at the University of Hawaii at Manoa. Purified capsule EPS at 2.5 g/L in water were dialyzed 1:60 against Type II water to remove any salts using a Spectra/Por 5 Dialysis Membrane (12-14 kD) prior to analysis. Ions quantified were: fluoride, chloride, nitrite, bromide, nitrate, phosphate, sulfate, lithium, sodium, ammonium, potassium, magnesium, and calcium in ppm.

Exopolysaccharide Chemical Characterization

The exopolysaccharide was characterized by glycosyl composition analysis and linkage analysis and size exclusion chromatography (SEC) performed by the Complex Carbohydrate Research Center at the University of Georgia. Briefly, glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis. GC/MS analysis of the TMS methyl glycosides was performed on an AT 6890N GC interfaced to a 5975B MSD, using an Alltech EC-1 fused silica capillary column (30 m×0.25 mm ID). For glycosyl linkage analysis, the samples were permethylated, reduced, repermethylated, depolymerized, reduced, and acetylated; and the resultant partially methylated alditol acetates (PMAAs) were analyzed by gas chromatography-mass spectrometry (GC-MS). Initially, the sample was suspended in 200 µl dimethyl sulfoxide. The sample was then left to stir for 1 day. The sample was permethylated using potassium dimsyl anion and iodomethane. The permethylated uronic acids were then reduced using lithium borodeuteride. The sample was then permethylated again by treatment with sodium hydroxide and methyl iodide in dry DMSO. This additional permethylation was to insure complete methylation of the polymer. Following sample workup, the permethylated material was hydrolyzed using 2 M trifluoroacetic acid (2 h in sealed tube at 121° C.), reduced with $NaBD_4$, and acetylated using acetic anhydride/TFA. The resulting PMAAs were analyzed by GC/MS on an Agilent 7890A GC interfaced to a 5975C MSD (mass selective detector, electron impact ionization mode); separation was performed on a Supelco SP-2380 fused silica capillary column (30 m×0.25 mm ID). For SEC, the sample was filtered through 0.22 µm Ultrafree-MC HV Centrifugal Filter, followed by injecting 50 µl into an Agilent 1200 HPLC. The system uses a Superose 12 column, eluent of 50 mM ammonium acetate, pH 5.5, flow rate of 0.8 mL/min, and evaporative light-scattering detection. The calibration curve was calculated based on the retention time of five Dextran standards (5K, 10K, 40K, 66.9K and 167K) and glucose.

Figure 2:
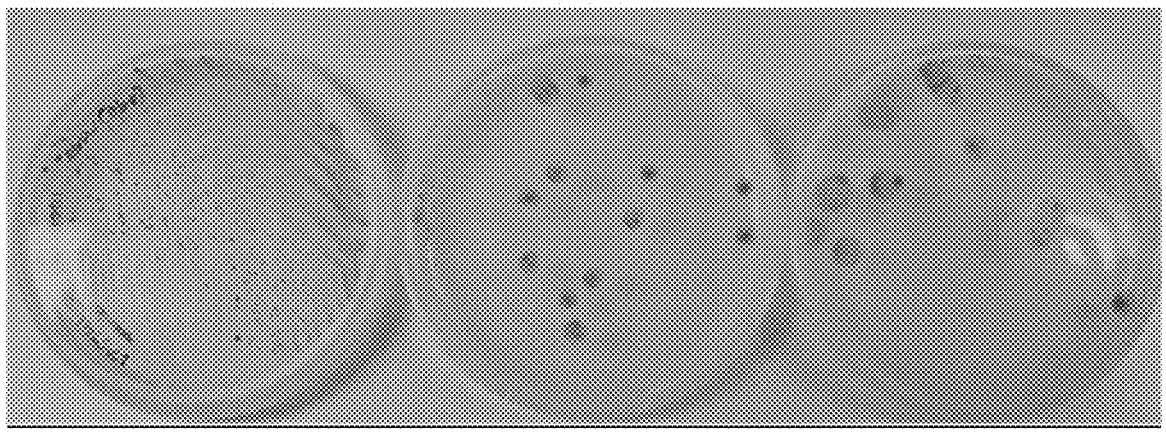
FIG. 2. Three accessions of *Parachlorella kessleri* originating in the Hawaiian Islands, with differing ability to produce exopolysaccharides (EPS). The plate on the left is a non-subterranean strain KAS741 collected on Oahu island, with low amounts of EPS produced and visible. The two other plates show subterranean strains KAS1544 (middle plate) and KAS1543 (right plate) collected on Hawaii Island. Both strains produce large amounts of EPS, visible as a halo surrounding each colony and sometimes coalescing with neighboring colonies. KAS1543 was selected to practice the method of the invention. It is deposited as KAS1543 *Parachlorella kessleri* var. *volcanica* ATCC Patent Deposit #PTA-125105.

Example 4-Isolates of *Parachlorella* and Production of Cell-Bound Exopolysaccharide (Eps) Substances Identification. Environmental samples from lava tubes and environs on the island of Hawaii were handled and screened by PCR amplification per Example 1 and using additional primer sequences unique to *Parachlorella*. The additional primers were used to obtain DNA sequence of ITS1 region, namely CAAGTCATCAGCTTGCGTTG (SEQ ID NO: 7) and GTTCGCTATCGGTCTCCCGT (SEQ ID NO: 8). After plating, three non-identical species were revealed. These were referred to as accessions KAS1543, KAS1544, and KAS1545. When observed on solidified medium under fairly low fluorescent light (30 µmol/m/s), colonies of different species produce various amounts of exudate typical of a bacterial or eukaryotic microalgal exopolysaccharide seen as a halo around a cell colony (FIG. 2).

These accessions best fit GenBank accessions for *Parachlorella* (synonym of *Chlorella kessleri*; Guiry and Guiry 2018) or *Dictyosphaerium*. Based on morphology seen by light microscopy the latter genus was eliminated, and the accessions are designated as *Parachlorella*. Nevertheless, it is recognized in the field of phycology that taxonomic assignments are subject to name changes or reclassifications as more information becomes available. Two accessions subsequently show particular promise for high volume EPS production when grown photoautotrophically on solidified medium with 2 or more months intervening between subcultures (nutrient limitation). Moreover, they are very responsive to increased EPS production when located immediately adjacent to the incubator door lights as opposed to back in the incubator about 2 feet from the light source. These accessions are designated KAS1543 and KAS1544. In light, the fresh cultures appear green, spherical, 4-8 µm for KAS1543 and KAS1544, and 2.5-5 µm for KAS1545.

Accession KAS1543 shows 99.85% (1335/1337 matches, 0 gaps) similarity with the 18s rRNA region of *Parachlorella kessleri* (FM205846.1). Additionally, another partial 18s rRNA (outside of the 1335/1337 previously) and partial ITS1 region of KAS1543 is 99.25% (661/666 matches, 0 gaps) similar to *P. kessleri* (FM205846.1).

KAS1543 is named KAS1543 *Parachlorella kessleri* var. *volcanica* ATCC Patent Deposit #PTA-125105.

Production of cell-bound capsular EPS. Heterotrophic culture of the KAS1543 and the other *Parachlorella* proceeds according to Example 2 to very high densities. Synthesis of copious capsular EPS in KAS1543 *Parachlorella* grown heterotrophically is discovered upon a purposeful change in culture conditions that is nutrient depletion, specifically N depletion. In this example, cells are subjected to urea depletion while the non-urea nutrients are replete. Under the capsular EPS accumulation conditions, the cells cease dividing followed by a significant increase in the proportion of capsular EPS compared to the non-capsular biomass over time. Production of some mucilage is a trait associated with an ability of some microbes to resist desiccation. In this case, there is no desiccation involved. The subterranean *Parachlorella* species are induced to synthesize a product of interest, located in the capsule, in very large quantities by altering its metabolism under conditions of rich nutrition followed by low nutrition.

The amount of capsular exopolysaccharide is quantified using the following steps: This entails purifying the solids away from the culture medium using centrifugation; the supernatant culture medium is discarded. The cell solids with the cell-bound capsule are washed in water sufficient to remove residual salts. Use of deionized or Type II water ensures no introduction of exogenous salts. Dewatered samples are freeze-dried for weighing before and after a heat treatment that removes the capsule for quantification. Capsular exopolysaccharides accumulate over a period of one to several days. After 2 days, capsular EPS is 50% of the biomass weight.

For scaled production, cells with capsule are grown according to Example 2 for *Parachlorella*. As in FIG. 3, cells with capsule are purified away from the broth by centrifugation. Next the capsular EPS is removed from the cells by heat treatment. One heat treatment is boiling. The treatment is for 10 to 30 minutes or longer. Boiling microalgae (heating at or above 100° C.) is well-established to cause cellular disruption and lysis for many species. Remarkably, heating *Parachlorella* KAS1543 at 100° C. and higher, such as under conditions of autoclaving at 121° C., succeeds in breaking the interactions between bound EPS and the microalgal cell wall without cellular lysis of this strain. Cells remain visibly intact and with no cellular debris present when observed with a Nikon microscope under 1000×. In this way, the intracellular compounds such as proteins, polyphenols, pigments, oils, and even low molecular weight (LMW) intracellular carbohydrates stay inside the cells and are not contaminated, providing for a pure, solution of higher molecular weight EPS. Heat treatment can also be below boiling such as 50° C. or 60° C. or 70° C. or 80° C. or 90° C., with a combination of heat and duration providing desired yields. The solution is naturally alkaline, about pH 7.5-9, before and after boiling; the solution acidifies to about pH 6.5-7 during autoclaving, if there is chlorophyll present that degrades. Acidification such as by addition of citric acid or use of a citrate buffer system can be used without performance alteration of the EPS. Adjustment of pH can occur at step 70 in FIG. 3. Heat treatment may use varying cell densities depending on subsequent process steps and desired concentrations. One typical density uses 14 g biomass per L.

The yield of EPS and their properties from harvested cells of *Parachlorella* treated for 10 minutes to 30 minutes is sufficient. However, the heat treatment time can be increased to one hour or several hours at a water temperature at or above boiling (100 to 121° C.), to release various amounts of EPS but usually with diminishing returns. Released EPS has increased moisturizing capacity with increased heating time; a 30-minute boil is sufficient to generate EPS with high moisturizing capacity measured as per Example 3.

A quantitative amplification of EPS occurs when the cells of this strain are cultivated in a sequential fashion of heterotrophy followed by cultivation under nitrogen stress with optional finishing in light (>30 µmol photon/m$^2$/s, 6500 K light for 24 for 144 hours). Capsular EPS is 50% of dry weight after 2 days. This increases to 60% and then to 70% or more of the cell biomass on a dry weight basis in 5 days and then 7 days, respectively. Positive moisturizing results from both paths shown in FIG. 3, regardless if the biomass is exposed to light or continuous darkness prior to heating to remove the capsular EPS in step 50. Note that the solids from step 30 contain capsular EPS formed in complete darkness in step 20 after cell division ceases and the culture become N-stressed, also part of step 20. The culture from step 20 can take an alternative path to become light finished as N-stressed cultures during step 40.

Formation of EPS increases under higher light, with no additional cell division. While high light is recognized to stimulate EPS production, the increase in EPS accumulation occurs independent of cell growth across the subterranean *Parachlorella*; and depends on the strain selected. KAS1543 is highly responsive to photoactivation of EPS levels, even under low light (see FIG. 2 for comparison with two other *Parachlorella* strains, one that is non-subterranean and one that is collected at the same general location as KAS1543).

If chlorophyll is present, some green color leaches out during the boiling step. This can be removed with activated carbon. After cell debris is cleared from the released EPS, liquid can be recycled through activated carbon filters such as HydroNix Water Technologies (CB-45-2005). The amount of chlorophyll present is lower in heterotrophically grown cells compared to light finished cells.

Remarkably, the capsular EPS yield per biomass dry weight equivalents using these methods (in dark only or in dark followed by light) far exceeds that reported for released EPS yield from culture broth from other *Parachlorella*. In one instance, for *Parachlorella* cultures produced industrially to at least 50% EPS yield in total darkness or at least 60% EPS using a photo-finishing step, a 35 g/L heterotrophic culture can produce 17.5 g/L EPS or 21 g/L EPS, respectively. In another instance a 15 g/L heterotrophic culture can produce 7.5 or 9 g/L EPS, respectively. The capsular EPS, once removed from the cells and in combination with water, is a moderately viscous solution.

Residual biomass consisting of de-encapsulated cells from the stressed subterranean *Parachlorella*, including isolate KAS1543, has a remarkable lipid content exceeding 80%, such as of 87% for KAS1543, consisting of dermally desirable fatty acids including 43% oleic, 27% palmitic, and 21% linoleic plus linolenic, as well as the carotenoid lutein. This is determined by acid hydrolysis of ethanolic extract using gas chromatography/mass spectrometry as is known in the art, and thin-layer chromatography and spectrophotometry for carotenoids.

Freeze-dried capsule EPS has the appearance of cotton candy, it is not particulate or a powder but has an amorphous appearance. EPS can also be spray dried and still completely dissolves in aqueous solution. As the capsular EPS liquid concentrate is filter-sterilized with preservative using an industrial scale pressure vessel and Millipore pre-filter and 0.2- to 0.3-micron final filters (hydrophilic PTFE), no drying is required for the ingredient for stable storage for at least 3 months at 45° C. (equivalent to 24 months at ambient temperature).

Example 5-Chemical Composition of *Parachlorella* Capsular Exopolysaccharide (Eps)

This example describes a biogenic substance that is a cell secretion from KAS1543 *Parachlorella kessleri* var. *volcanica* ATCC Patent Deposit #PTA-125105, specifically a capsular heteropolysaccharide polymer produced and purified according to Examples 2, 4 and 5. The chemical composition and structure of the EPS is determined. As a precaution, the EPS is further washed and then dialyzed 1:60 against Type II water to remove any salts using a Spectra/Por 5 Dialysis Membrane (12-14 kD) prior to analysis. The sample was lyophilized and powdered in preparation for analysis.

Figure 5:
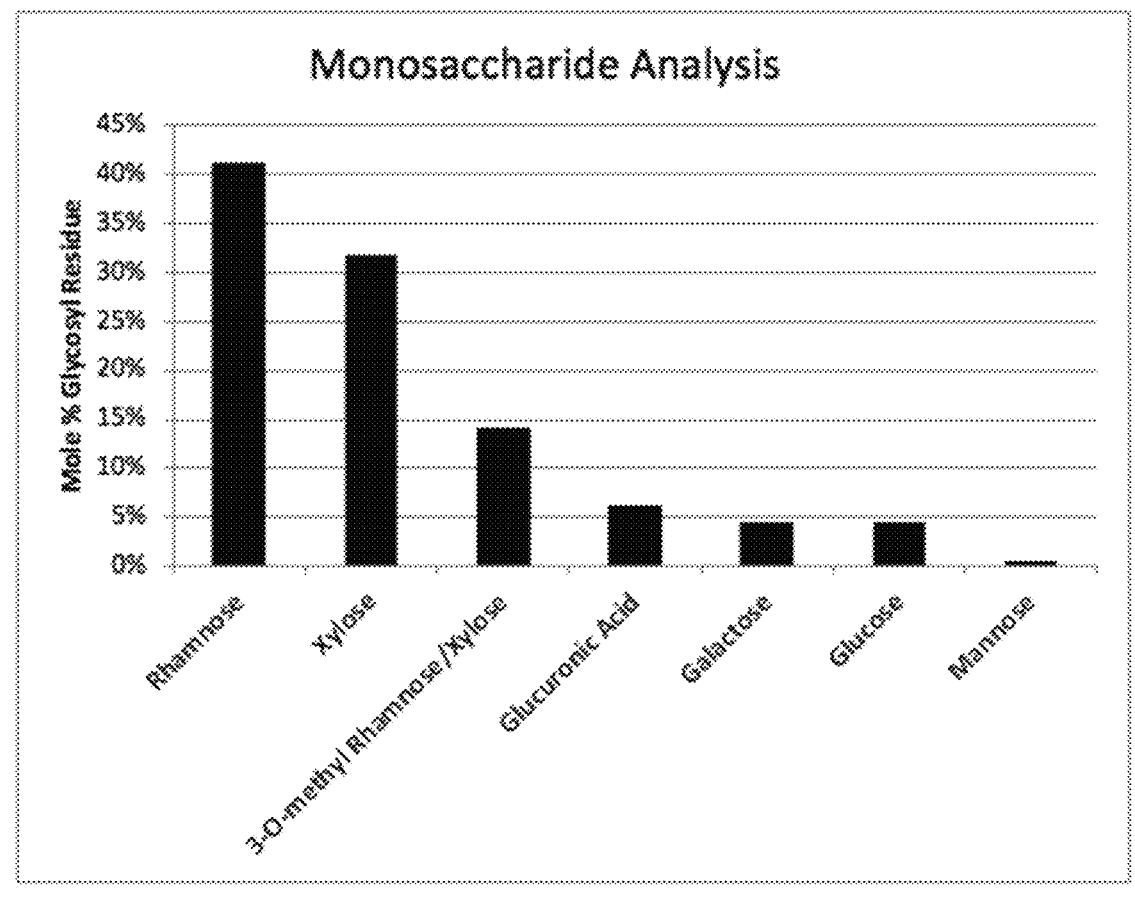
FIG. 5. Example composition of monosaccharides comprising capsular exopolysaccharide obtained from KAS1543 *Parachlorella kessleri* var. *volcanica* ATCC Patent Deposit #PTA-125105.
Figure 6A:
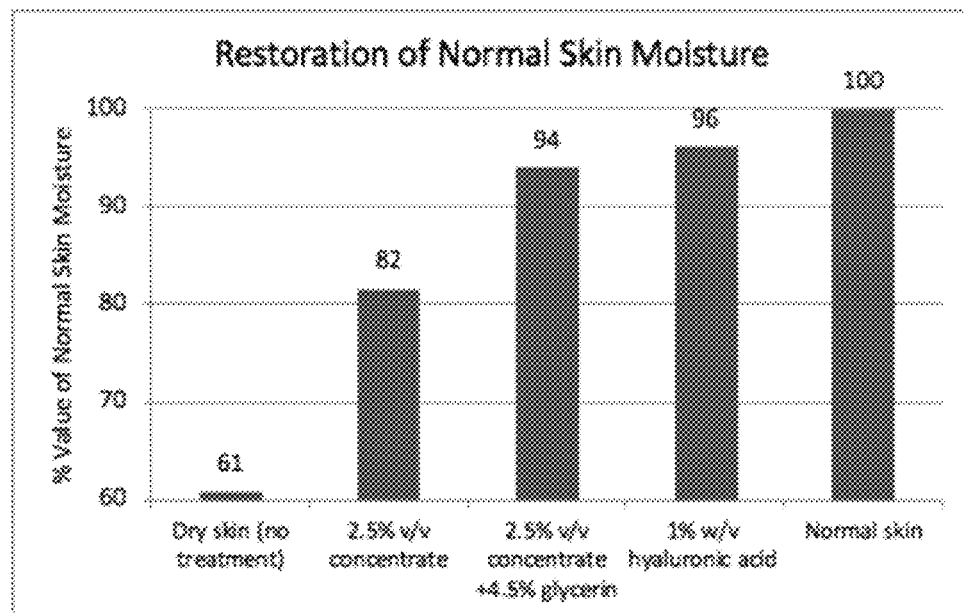
FIGS. 6A and 6B. Determining the moisturizing properties, use rate, and other performance comparisons of a capsular exopolysaccharide concentrate derived from KAS1543 *Parachlorella kessleri* var. *volcanica* ATCC Patent Deposit #PTA-125105. (6A) Capsular exopolysaccharide helps restore dry skin to normal moisture levels. It has a stronger hydrating power than hyaluronic acid, on a dry weight basis. A 2.5% liquid concentrate diluted to 0.175 g/L exopolysaccharide on the skin is over 30-fold more potent on a weight basis for increasing skin moisture, compared to 1% (w/v; 10 g/L) hyaluronic acid. (6B) A 2.5% liquid concentrate diluted to 0.175 g/L exopolysaccharide on the skin works synergistically with glycerin for skin moisturization.
Figure 6B:
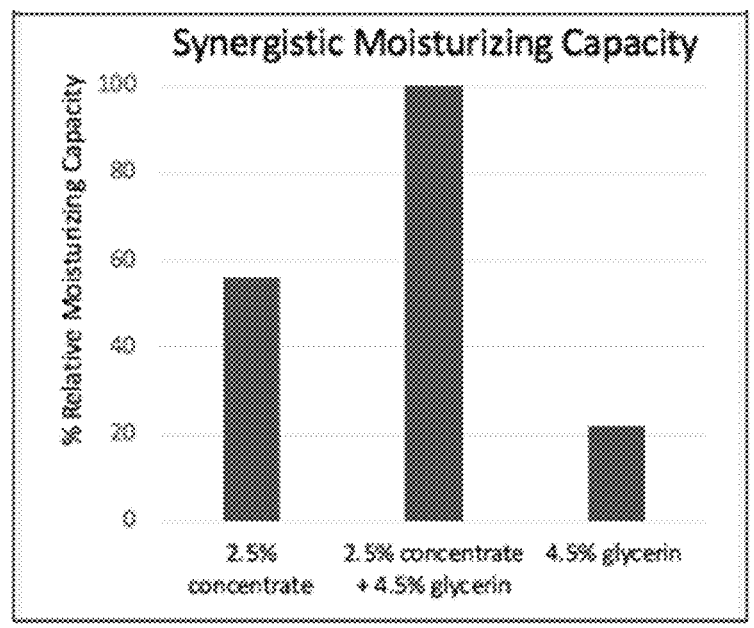

The exopolysaccharide is characterized by glycosyl composition analysis and linkage analysis as described in Example 3. Rhamnose is discovered to be the most abundant neutral sugar, followed by xylose, glucuronic acid, galactose, glucose and mannose (see FIG. 5 for general composition). The polymer presents a 6-9% content of uronic acids, which is desirable for skin care application and may also serve as binding sites for divalent cations. Glycosidic linkage analysis showed rhamnose, xylose and glucuronic acid to be in terminal positions, key to facilitate water holding of the polysaccharide. As with the compositional analysis, rhamnose and xylose were the main components of the linkage analysis. The rhamnan in the sample appeared to be complexed with multiple branch points (terminal; 2 linked; 3 linked; 3,4 linked; 2,3 linked; 2,4 linked; 2,3,4 linked). The xylan in the sample was simpler with 4 linked xylose and a smaller amount of 2,4 linked xylose was the only xylose linkages present. The glucuronic acid was with terminal and 4 linked residues. As with the composition, there were lesser amounts of galactose and other hexose residues.

The major sugar components have other implications that can benefit personal care products. Rhamnose can be an effective anti-aging agent. It has a natural affinity for the papillary dermis and encourages fibroblasts to be more active. Rhamnose polysaccharides are marketed as liquid moisturizer, used in anti-aging creams. Xylo-oligosaccharide (XOS) has emerging prebiotic properties; in the context of the human intestine it is known to enhance growth of *Bifidobacterium*. It is conceived that, if needed, hydrolysis of the EPS through methods known in the art can be performed to form shorter chain oligosaccharides for this purpose. Glucuronic acid can also be an important skin-conditioning agent and humectant, especially in certain linkage positions.

Additional analysis per Example 3 shows that the percentage of sulfur in EPS is 0.12%. This result indicates that the capsular exopolysaccharide from the subterranean source is both sulfated and contains glucuronic acid. Sulfated EPS is known to benefit skin surface topography of dry or older skin and to extend the effect of moisturizers. Hyaluronic acid is an effective moisturizer due in part to being a sulfated polysaccharide that contains glucuronic acid.

Example 6-Microalgal Products and Compositions for *Parachlorella* Capsular Exopolysaccharide (Eps)

Figure 4:
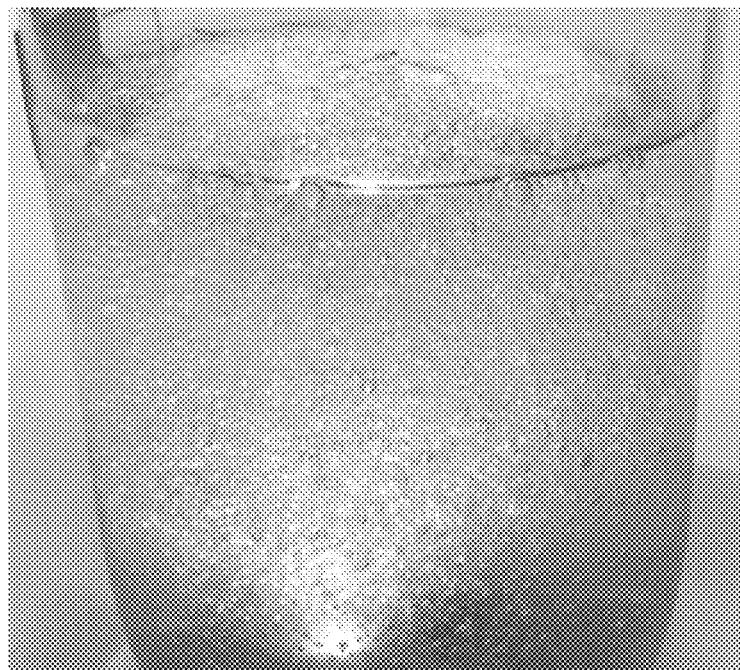
FIG. 4. A 2-L solution of capsular exopolysaccharide concentrate obtained from KAS1543 *Parachlorella kessleri* var. *volcanica* ATCC Patent Deposit #PTA-125105. To illustrate the solution's viscous nature, the image shows entrapped, slowly rising bubbles formed after vigorous shaking.

The EPS substance of Examples 5 and 6 from KAS1543 *Parachlorella kessleri* var. *volcanica* ATCC Patent Deposit #PTA-125105 is tested for viscosity and also for an increase in volume (swelling) upon contacting with water compared to the anhydrous volume of lyophilized exopolysaccharide. Capsular EPS at 0.25% w/v has a viscosity of 7.88 cp measured by a DV3TLV cone/Plate Rheometer with a CPA-40 spindle at 30 rpm, 25° C., with the data analyzed by Brookfield RheocalcT V2.0.37. This EPS sample, when tested for moisturizing properties on human skin using a moisture analyzer per Example 3, shows an excellent increase in skin moisture levels to 50-60% (normal) after application. There is a clearly perceived sluggish, thick flow of the concentrated hydrosolubilized polysaccharides of the *Parachlorella* EPS. When a bottle with the concentrate is shaken to generate bubbles, the bubbles stay trapped for a time in the viscous solution as they rise very slowly to the top compared to water (FIG. 4).

In a separate test for swelling properties, 11 mg of dried EPS is completely dispersed in 1.1 ml of water in a 1.5 ml tube, vortexed and centrifuged; the tube is left overnight for convenience. The polysaccharide swells into a gel and visual inspection shows an increase in volume of about 2.5-times upon contact with water compared to the anhydrous volume of dried EPS. This indicates water retention and water-holding capacity by the EPS. This supports the moisturizing property observed during topical application.

Molecules with metal chelating activity inhibit the formation of reactive oxygen species by binding and inactivating metal ions, which serve as intermediates in the formation of free radicals. Metal chelating activity of the EPS is determined as is known in the art (Dinis et al. 1994), using the ferrous ion ($Fe^{2+}$) chelating activity determined spectrophotometrically by monitoring the absorbance of ferrous iron-ferrozine complex at 562 nm using a Biotek Synergy HTX microplate reader. The EPS is a strong chelator, exhibiting 83% activity at 0.005% w/v. The effective concentration that chelates 50% of the metal ions (EC50) is 0.0026% w/v or 26 mg/L. An application for the metal chelating capacity of EPS is in "anti-pollution" skin care and hair care products, to bind metal ions from environmental pollution before they can penetrate the skin and contribute to the formation of unwanted ROS. In another application, EPS—including in the form of encapsulated cells—can trap heavy metals from mining tailings and other industrial operations.

The formulated ingredient of exopolysaccharide from subterranean *Parachlorella*, including KAS1543 *Parachlorella kessleri* var. *volcanica* ATCC Patent Deposit #PTA-125105 is 100% water soluble, non-greasy, non-staining, light, and non-sticky. Topical application leaves the skin feeling moisturized, hydrated, softened, soothed, smooth, and without tackiness or heaviness. When combined with glycerin, it is absorbed at a shorter time and leaves a sheen on the skin. It can be characterized as a preparation that increases the soft feel of the skin, including for lip care. Based on these observations the ingredient provides moisturizing, hydrating, softening, smoothing, rejuvenating, soothing, protecting, and restoring properties.

Its water-holding capacity provides its properties as a humectant, demonstrated using the skin moisturizing assay of Example 3. Tests performed on dry skin (27.5% moisture) using capsular EPS at 0.0175% DW basis show a restoration of skin's moisture to near normal values. Its affinity for skin extends to use in compositions for scalp hydration/hair care as well. The EPS solution is tested for moisturizing capacity according to Example 3 at various pH (adjusted using citric acid) from pH 4.5 to pH 9.0. At all values of pH, the EPS is stable and suited for moisturization.

Other methods to demonstrate hydration are also used. An aqueous solution of EPS at 0.0175% DW basis is applied in a standardized fashion to the specified regions of the forearms. To demonstrate hydration in rinse-off products for showering, the forearm is humidified using a mist atomizer with three sprays over 30 seconds. The solution is administered by rubbing for 1 minute, then rinsed for one minute and dried by pressure application with absorbent paper towels. Faster recovery from irritation, by tape stripping applied in a controlled fashion, is assessed over hours and days by the participants. It can also be assessed for reduced loss by the transepidermal water loss (TEWL) test as is known in the art (du Plessis et al. 2013).

As an ingredient composition, the exopolysaccharide from *Parachlorella*, such as using KAS1543 *Parachlorella kessleri* var. *volcanica* ATCC Patent Deposit #PTA-125105, is formulated with water and 1-1.5% phenoxyethanol preservative after pH adjustment to that compatible with the preservative (INCI: Aqua, Saccharide Isomerate, and Phenoxyethanol). Use rate is about 2.5 to 5% for general formulas and lower or higher for specific applications. This composition is stable in color, odor, form and pH for at least 2 years based on accelerated testing at 45° C. in the preferred storage containers and by repeated freeze-thaw testing.

For a moisturizing face cream, one composition can be formulated as follows: 6% Xyliance, 3% cetyl alcohol, 5% avocado oil, 10% macadamia nut oil, 5% kukui nut oil, 2.5% *Parachlorella* exopolysaccharide concentrate, 2.5% glycerin, 63.5% water, fragrance and preservative. Oil and water phases are homogenized together as is known in the art to form a composition suitable for topical administration. Similarly, for face serum, formulating with commonly used components shows high compatibility with the subterranean-algae derived capsular exopolysaccharide produced by the method of this invention. A serum composition is formulated as follows: 5% vitamins, 1% hyaluronic acid, 6% anti-aging bioactives, 3% texture/feel compounds, 2% *Parachlorella* exopolysaccharide concentrate, 3% glycerin, preservative, fragrance, water and other diluents up to 100%.

A lipstick product uses the exopolysaccharide ingredient for moisturization combined with solidifiers and glossiness agents such as beeswax, carnauba wax, candelilla wax or white soft paraffin; diluent oils such as castor, kukui or olive oil for even dispersal of a colorant and as emollient such as cyclomethicone; surfactant such as glycerin; antioxidants such as vitamins E and C; and floral essence and parfum as preservative. One composition comprises 45% solidifiers and glossiness agents; 30% diluent and emollient oils; 7.5% colorant; 6% anti-oxidant; 5% surfactant; 4.5% *Parachlorella* saccharide isomerate; and parfum/preservatives. The proportions can vary as needed with selection of specific agents and the product definition. The mixture of ingredients is prepared as known in the art to form a composition suitable for topical administration as a lipstick.

Substances produced from subterranean algae using the method of this invention reveal their applicability in personal care compositions in this example and in subsequent examples, corroborated by at least 6-month stability of formulations measuring color, odor, stability (form and pH), and no change after repeated freeze-thaw testing.

Example 7-Microalgal Exopolysaccharide as a Protein Stabilizing Agent

In this example, two instances are provided for a composition that is a biotic complex that can be an association with a protein. The association results in improved protein stability and/or provides performance as a vehicle in cases where a water-binding functionality is desired.

A. The bright blue color of C-phycocyanin (C-PC) is unstable in light and at a temperature above 45° C., limiting its use in many cosmetics products requiring high temperature formulation such as 70° C. or to receive a 2-year shelf life rating under accelerated testing performed at 45° C. for 90 days. Natural EPS is appropriate for use in cosmetics and food stuffs. Therefore, its ability to perform as a protein crosslinker, by formation of chemical bonds, is desirable to help maintain a high ordered structure of C-PC or other such proteins when exposed to light or elevated temperature.

Extraction and isolation of C-PC are carried out as is known in the art (Wu et al. 2016) using commercial grade biomass from a source in Hawaii. The C-PC is then further purified by ultrafiltration using a 10 kDa membrane to obtain an absorbance ratio of A620/A280 of 1.4 and stored frozen as a lyophilized powder. For testing, powder is solubilized in phosphate-citrate buffer to 0.4 mg/mL. Samples are tested for thermal stability at 65° C. for 30 minutes, at pH 6.0, per Example 3. The addition of EPS at a concentration of 1% (w/v; produced from resolubilized lyophilized powder with no added grinding) results in a reduction of the CR value by 13% compared to the control lacking stabilizing agents after exposure to 65° C. for 30 min at pH 6.0. This indicates added stabilization, which can likely be optimized with additional testing. Antioxidant capacity is measured using the DPPH Radical Scavenging Activity as is known in the art (Alam et al. 2013), with the modification of using DPPH (1,1-diphenyl-2-picrylhydrazyl; Sigma-Aldrich D9132) in methanol (0.06 mM), and readings taken on a Biotek Synergy HTX multi-mode microplate reader. The antioxidant activity of phycocyanin shows an IC50 of 1.8 mg/mL and the EPS-treated sample shows a 20% reduction.

B. The protein Type VII collagen (Col7), which is intrinsically disordered, is important for skin integrity. It is particularly important for patients with chronic skin wounds. For collagen proteins to promote wound healing, a vehicle comprised of 1% EPS and 9% carboxymethylcellulose is used to deliver active recombinant type VII (30 micrograms) to a wound site on skin. This acts to facilitate wound healing as a moisture-retentive topical dressing along with protein stabilization. Similarly, the EPS carries fetal skin cell protein lysate at a concentration of 0.01% to 100% in a topical composition. Such an approach can be used to release a water-soluble epidermal growth factor and derivatives that are of value in dermatology.

Example 8-Microalgal Substance and Composition that is A Cell Constituent: Astaxanthin-Rich Extract This example describes a biogenic substance that is rich in natural astaxanthin, a pigmented cell constituent that is a xanthophyll, obtained from subterranean microalgae. Xanthophyll pigments are considered vital to provide protection against effects of harmful UV irradiation, and thus are prized for topical application to skin, lip and hair and for potential use in extreme conditions such as on extraterrestrial habitats such as on space stations or Mars. They are also components of animal feed (see Example 13). This includes the genera *Pseudospongiococcum, Scenedesmus* (syn. *Desmodesmus*), and *Coelastrella* (syn. *Scenedesmus*). Three representative accessions that originate from a shallow puddle in complete darkness in a wet lava tube in the transition dark zone are isolated and grown heterotrophically on glucose or carboxylic acid per Example 2. KAS1562B is determined to be in the Chlamydomonadales, family Chlorococcaceae. Sequence analysis of KAS1562B indicates 99.9% match of 18s RNA to *Pseudospongiococcum protococcoides* (GenBank accession KU057947.1). KAS1562A and KAS1562C are determined to be members of the family Scenedesmaceae. All turn red on plates over time. KAS1562B has round cell dimensions of 6-10 μm. KAS1562A forms 2- and 4-cell colonies typical of *Scenedesmus*-like species with cell size of 2-2.5 μm×3-5 μm. Sequence analysis of KAS1562A indicates 99.4% match to *Scenedesmus armatus* (GenBank accession KF673362.1). Microscopy of KAS1562C suggests similarity to *Coelastrella* (syn. *Scenedesmus*).

Figure 7:
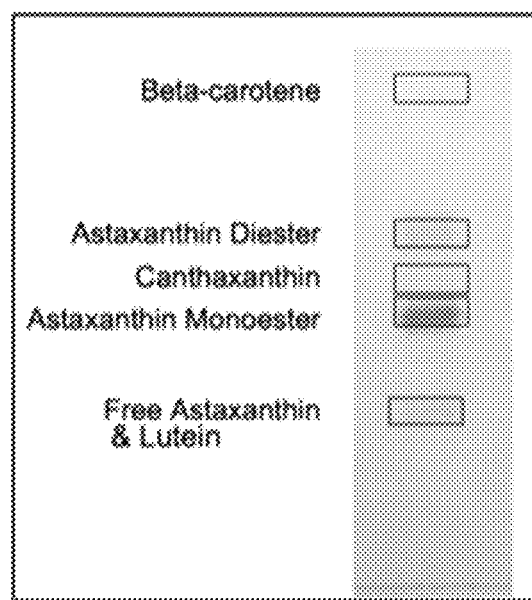
FIG. 7. Carotenoid analysis by thin layer chromatography of KAS1562B, *Pseudospongiococcum protococcoides*, showing predominance of astaxanthin.
Figure 8:
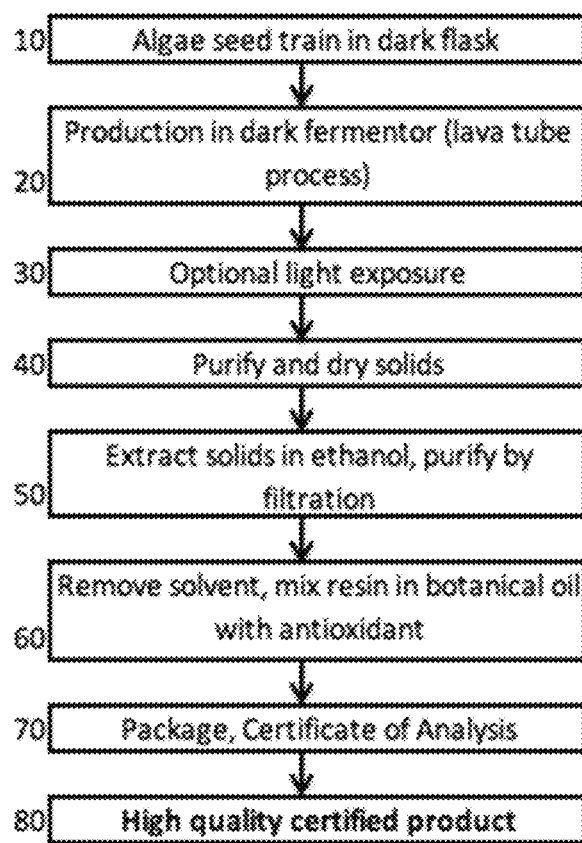
FIG. 8. General manufacturing flow for astaxanthin-rich resin from KAS1562B, a subterranean *Pseudospongiococcum protococcoides*, using the "lava tube process" of dark fermentation. The algae extract can be blended in a dermally acceptable oil and an antioxidant such as Vitamin E for use in skin care applications.

Flasks of axenic KAS1562B *Pseudospongiococeum protococcoides* that are cultured under darkness on glucose for over 8 months with no intervening subculture, and with no agitation, stay pale green and do not form noticeable red pigmentation. Cells remain viable despite the extended nutrient limitation in complete darkness, which may be uniquely characteristic of subterranean microbes. A parallel flask culture kept under light and no agitation for over 8 months with no subculture turns a vibrant ruby red or fruit red color of Pantone 180C. Surprisingly, a heterotrophic flask moved to modest irradiance (30 µmol photon/m/s), such as found when exiting a cave, turns red. Pigment analysis proceeded following the method for carotenoids/xanthophylls in Example 3, using 9.8 mg of KAS1562B extracted in 1.225 mL of acetone and spotting 100 µg (12.5 µL) onto the thin layer chromatography plate. Bands were excised and eluted into acetone for spectrophotometric analysis per Example 3. Based on migration and absorption maxima, the major carotenoid was identified as astaxanthin monoester. Analysis revealed the species to produce predominantly astaxanthin, with minor detectable canthaxanthin and beta-carotene (FIG. 7). Additionally, pigment formation is confirmed to occur in complete darkness under low nutrition conditions of nitrogen depletion when aerated with 110 rpm in a shaker at 23-27° C.; light is optional per FIG. 8 step 30 and can serve to increase specific productivity. Quantification indicated total astaxanthin content of 0.45% to at least 1% optimization of nitrogen depletion during late exponential phase conditions under fed-batch cultivation. For scale-up of KAS1562B and the other algae following FIG. 8, cultures are grown heterotrophically in steps 10 and 20 in *Pseudospongiococcum*, *Coelastrella*, *Scenedesmus* and *Chlorella* medium and conditions described in Example 2. In the fermentor, cultures reached high densities in a short period of time; a KAS1562B culture started at 0.5 g/L can reach 30 g/L in 4 days in darkness. Such a growth rate for *Pseudospongiococcum* is replicated using the cultures of *Scenedesmus* and *Coelastrella*. The commercial advantage is that high-density biomass can be generated at large quantities using dark fermenters (termed the "lava tube process") followed by the equivalence of low light exposure (step 30) under nutrient stress (as a part of step 20) that is sufficient to produce the target pigment, astaxanthin. This can employ indoor or outdoor illuminated agitated deep tanks, lagoons or raceways without the requirement for culture dilution. Total carotenoids with xanthophylls are extracted as a resin following FIG. 8, using ethanol as an acceptable solvent for processes for skin care ingredients. Other solvents or extraction methods can be employed as well, as is known in the art for algal extracts. The solvent is distilled off and the pigment resin in step 60 is formulated into a composition with squalane or botanical oil such as macadamia nut oil and an antioxidant (INCI: Macadamia Ternifolia Seed Oil; with 1% vitamin E) prior to packaging in step 70. The high quality 0.4% ingredient of step 80 is for use in topical skin care products at about 1-3%. Vehicles other than oils can also be used to facilitate dermal delivery of the active ingredient.

Example 9-Microalgal Substance and Composition Containing Fucoxanthin

Figure 9:
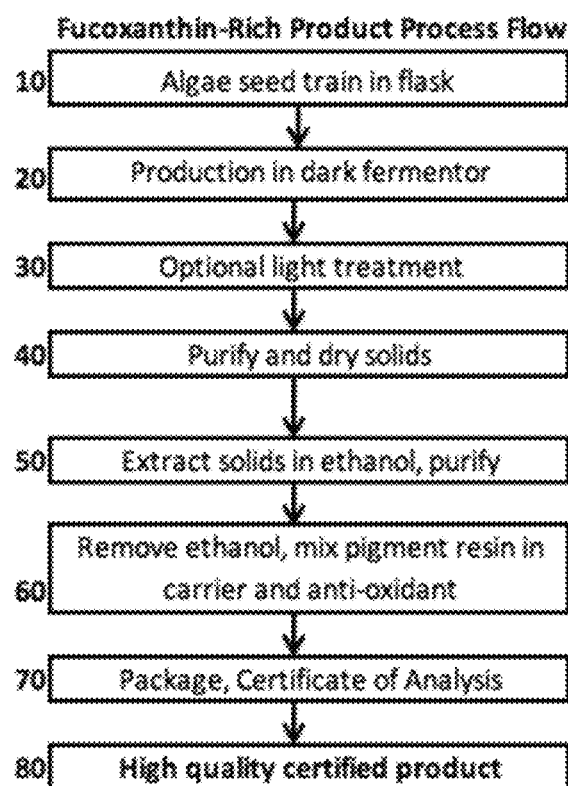
FIG. 9. General manufacturing flow for compositions containing fucoxanthin derived from subterranean microalgae produced using the "lava tube process" of dark fermentation. The algae extract can be blended in a dermally acceptable carrier and an antioxidant for use in skin care applications.

This example describes a bioproduct that is rich in the xanthophyll fucoxanthin, a pigmented cell constituent from subterranean diatoms manufactured as shown in FIG. 9 using the "lava tube process" of dark fermentation. Surprisingly, despite originating from the dark cave environment, subterranean diatoms of *Sellaphora* and others were able to form this photosystem accessory pigment when supplied with glucose and minerals per the diatom medium of Example 2 under darkness and nutrition limitation in late exponential phase. One *Sellaphora* isolate is *Sellaphora* KAS1565 isolated from a shallow puddle on a lava tube cave floor in complete darkness in the transition dark zone. KAS1565 is brown, cylindrical of size 2.5-5 µm×5-7.5 µm and can form chains of two cells with frustules unusually linked by a short non-filamentous bridge into a dumbbell appearance. The 18s sequence analysis per Example 1 reveals 98.4% match to *Sellaphora laevissima* (GenBank Accession EF151981.1) or *Eolimna minima* (GenBank Accession AJ243063.2; *Eolimna* is often synonymous with *Sellaphora*); and 98.0% match to *Sellaphora pupula* (GenBank Accession AJ544647.1). A different diatom by morphology, KAS1566, is isolated from the same shallow puddle and is brown, oval to cylindrical of size 3-4 µm×5-10 µm and forms short chains with no separating filament. Both are suspended cultures under agitation in freshwater. These specimens are grown at larger scale in diatom heterotrophic medium in freshwater from Example 2, as in FIG. 9 steps 10 and 20. Density exceeds 3 g/L in about 120 hours. Silica and glucose limitation in step 20 for the last 48 hours induce increased fucoxanthin per cell weight. This can be further increased by 10% when provided optional moderate irradiance (30 µmol photon/m$^2$/s), per step 30. Cells are dewatered by centrifugation at 4000×g in step 40, then rinsed with distilled deionized water, and recollected by centrifugation. Freeze-dried biomass is extracted in ethanol in step 50 for pigment extraction (50 to 100 g biomass/L ethanol) using a Pro250 homogenizer at 18,000 rpm for 30 minutes at temperatures below 37° C. Yield is about 0.7 to 1.2% DW fucoxanthin. Cell debris is removed by centrifugation and the pigment-ethanol solution is purified by filtration. The solvent is then removed by rotary evaporation in step 60. The resulting pigment resin contains one or both EPA and DHA fatty acids that aid in solubilization. Other fatty acids such as oleic, linoleic or linolenic polyglycerides are also present and known to be beneficial for skin and scalp care. This aids in mixing in carrier botanical oil in step 60 prior to packaging in step 70. The pigment resin is used at 0.3 g per 30 g total in a composition with botanical oil (includes 1% alpha-tocopherol antioxidant) such as macadamia nut oil (INCI: Macadamia Ternifolia Seed Oil) for the concentrated ingredient of 1% resin in step 80. Vehicles other than oils can also be used to facilitate dermal delivery of the active. Use rate of the concentrated ingredient is from 3-5% for effective in vitro anti-tyrosinase action. As a finished consumer product, the volume of extract used depends on the amount of bioactivity and product color desired but can be about 0.03% resin for skin whitening/even tone effects based on the anti-tyrosinase in vitro enzyme assay. Quantification of fucoxanthin and inhibition of tyrosinase (bioactivity testing) is per Example 3. When pigment resin from both species is tested for tyrosinase inhibition, 0.3-1 mg resin/ml oil delivers about 25-80% enzyme inhibition. As a result, biomass and fucoxanthin production is reduced to practice using subterranean diatoms produced by the method of this invention based on desirable growth rate and yield, and extracts are formulated into compositions useful in personal care. For a face oil or oil-gel, see the formulation for lutein extract in Example 11, substituting the fucoxanthin pigment resin for lutein pigment resin based on bioactivity level (such as tyrosinase inhibition) that is desired.

Example 10-Microalgal Substances that are a Cell Secretion: Whole-Shell Diatoms, Powders, and Colorants for Skin Care Products This example describes several products comprised of substances that are secreted by cells of subterranean algae, specifically of diatoms. One product is a biogenic ingredient that acts as a siliceous micro-abrasive, which utilizes the whole cell. A second product is a titanium-enriched biogenic ingredient. They both employ the rigid microalgal exoskeleton or shell secreted by diatoms. A third product is also an intact diatom cell used as a product's natural colorant.

Figure 10:
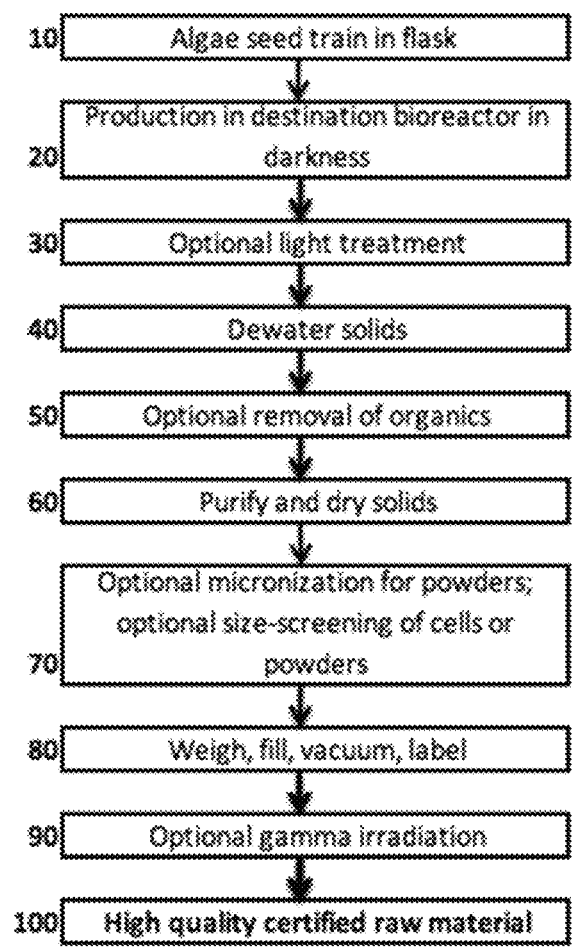
FIG. 10. General manufacturing flow for whole-cell and powder substances from subterranean diatoms.

Micro-abrasive product. Geologically new diatom cells are dewatered from their cultivation medium, described in Examples 2 and 9, heat dried or lyophilized into shells and aggregates, and stored in vacuum packs (for up two years at least) following FIG. 10, step 80. This material is discovered to be superior to geologically old diatomaceous earth (DE) for use in facial scrubs and cleansers. Unlike DE, which easily crumbles under mild pressure into a fine powder of undesirable nanoscale particle fragments of less than 10 µm, new diatom shells retain visible clumps after formulation (by mixing and heating as is known in the art) to provide desirable visible particles in facial scrubs and masks. Moreover, the geologically new cells as whole cells are effective in wash-off skin care products due to their micro-abrasive silica frustules. Clump size of agglomerated dried cells can be controlled through sieve sorting prior to packaging for ingredient purposes per FIG. 10 and step 70. Optionally the organic material is removed from the shells by detergent (mixed in 50 mg/L SDS in 100 mM EDTA solution) per step 50 prior to drying the biomass per FIG. 10 step 60. This is useful to remove leaching of color in the end formulation. While several different subterranean diatoms can be used in these capacities, this example uses KAS1537 isolated from a lava tube wall scraping in complete darkness. It is brown, rectangular/cylindrical of size 10 µm×25 µm. Although in its native habitat it is found adherent to a rock surface, through aeration delivered by agitation by the method of the invention, the microalgae became planktonic (suspended) in freshwater medium. This facilitated large scale production in FIG. 10, steps 10 and 20. A use rate of the substance from step 100, which has been optionally irradiated for sanitation purposes in step 90, in a skin cleanser product is determined to start at 0.4-0.8% for KAS1537 based on appearance of the inner forearm skin before and after treatment, looking for micro-abrasion without excessive reddening using a Nikon D810 camera body with a Nikkon 60-mm macro lens. This use rate results in low density visible particle clumps in the carrier. Generally, up to 2% inclusion for diatoms of 10 to 25 microns in length is suitable depending on preferred aesthetics regarding visual specks (as agglomerated cells) in the formulated product. Use rate and screened clump size for diatoms greater than 30 µm can be determined empirically.

Titanium-enriched biogenic powder product. Titanium is metabolically inserted into the frustule of a diatom to produce a micronized powder with SPF, UVA-PF, and antioxidant properties. Stock solutions of soluble silicon and titanium are prepared and administered following Jeffryes et al. (2008) and Chauton et al. (2015). Final concentrations of 0.36 mM Ti (from $Ti(OH)_4$ in concentrated HCl (37 wt. %)) and 6.2 mM Si (from $NazSiO_3·9H_2O$) are added in a fed-batch manner at 5.0 mL/hr for 24 hr, maintaining pH 8.0, per FIG. 10, step 20; the silica feed is turned off at the midway point without detrimental effects on the biomass. KAS1537 is grown heterotrophically on glucose with added Si and Ti according to Example 2. The feed with titanium began on the $3^{rd}$ day of fermentation culture. Following metals analysis of Example 3, it is found that the diatoms biomineralized the titanium into the frustules, yielding a composition in the frustule of 2.3 g Ti/100 g $SiO_2$. The substances are micronized to a fine powder to produce a titanium-enriched biogenic powder ingredient as a sunscreen booster to be applied over the normal sunscreen lotion. The particles do not cross the stratum corneum. When the powder is tested in an amount equivalent to the titanium dioxide used in the phenol stability assay of Example 3, the amount of phenol decomposition (% conversion) after a 2-hour irradiation period appeared similar, at about 2% conversion. Compositions of powders or other formulations may add reddish iron oxide, known in the art to adjust hues to more closely resemble skin and contribute further to sun protection as an inorganic UV blocking compound.

Whole-cell product as cosmetic colorant agent. Using the manufacturing process of the invention following FIG. 10, it is discovered that natural color leaches out from dried diatom cells in cosmetic bases to become an effective colorant in wash-off skin care products such as gels, oils, creams, masks and emulsions. This proceeds without a grinding requirement. A heterotrophic culture of diatom provides rich brown hues; if brought into the light a culture changes in pigment composition to become intensified in chlorophylls for a rich olive or moss green. Multiple subterranean diatoms performed similarly as a cosmetic colorant, with desirable coloration already seen using only about 0.05% inclusion rate. As colorizing agent, small diatoms are preferred so as to not interfere based on particle size. Accordingly, the subterranean species of Example 9 are exposed to light per FIG. 10, step 30 to provide a fresh moss or dark olive-green coloration in a wash-off facial cleansing gel. Similar to the micro-abrasive substance, the diatom colorant is stored in food grade static-free bags as a dried substance under vacuum and subjected to gamma irradiation as known in the art as a preservative measure.

Example 11-Microalgal Substance and Composition Containing Lutein

This example describes a biogenic substance that is rich in lutein, a pigmented cell constituent that is a xanthophyll. Lutein is essential to eye health, for example, in reducing progression of age-related macular degeneration. It is also thought to increase skin hydration and elasticity and protect against UV and blue irradiation. Subterranean *Pseudococcomyxa* cultured by the method of this invention serves as a commercially relevant source of lutein, as does de-encapsulated *Parachlorella* described in Example 4. KAS1535, sourced from a lava tube, is a promising candidate for heterotrophic lutein production and could also be considered for extraterrestrial cultivation such as for the moon or mars. KAS1535 has an oval cell of size of 4-5 µm×5-10 µm. DNA sequencing identifies its nearest matches as *Pseudococcomyxa simplex* (synonym *Coccomyxa simplex*, 99.3% match to GenBank Accession MH196858.1), *Pseudococcomyxa* sp. (99.6% match to GenBank Accession JQ315652.1) or *Coccomyxa melkonianii* (99.4% match to GenBank Accession KU696488.1) in the Trebouxiophyceae (*Chlorophyta*). The latter is considered an extremophile, thriving in low pH (2-4; acid tolerant) and heavy metals including iron (Malavasi et al. 2016). *Pseudococcomyxa simplex* can be chasmoendolithophytic (habitat in rock crevices) or found in volcanic fumarolic soils in Antarctic habitats. It can be grown similar to certain members of the Chlorophyte such as *Pseudospongiococeum, Coelastrella, Scenedesmus*, per conditions described in Example 2. It is robust with a specific growth rate of 3.08/d during log phase and a biomass productivity of 6.54 g/l/day. With a 1% lutein yield after a two-day irradiation under nitrogen stress, an industrial production run can produce about 40 mg/L/day lutein without optimization. Lutein can be purified away from other components as is known in the art for use in formulation for eye health. For a topical formulation the pigment resin is mixed into safflower (INCI: Carthamus Tinctorius) seed oil for a 0.2% solution used at a 3% application rate in creams, lotions or lip care products. Vehicles other than oils can also be used to facilitate dermal delivery of the active. The lipid fraction containing lutein of *Pseudococcomyxa* or de-encapsulated *Parachlorella* described in Example 4 is suspended in a carrier oil after processing into a pigment resin per Example 9. For example, this is formulated with other oils as follows to produce a flowable face oil or gelled face oil (oil-gel): 1% to 4% algal extract in carrier oil, 65% botanical oils, 25% to 35% emollient and emulsifiers (reduced or eliminated in the flowable face oil to be replaced by oils), fragrance, and 1% stabilizing anti-oxidant.

Example 12-Microalgal Substance and Composition Containing Phytoene and Phytofluene This example describes a substance with the colorless carotenoid precursors phytoene and phytofluene produced from *Haematococcus*. For purposes of illustration, the line KAS1708 *Haematococcus* pluvialis is used, having been identified by microscopy after isolation from standing water in an entry zone mesocavern. Cultivation proceeds in complete darkness using the *Parachlorella* base medium and nutrient feed concentrates described in Example 2. A 10 L inoculum (rather than 2.5 L in Example 2) is added to 80 L medium in a BioFlo610 fermentor where nutrients are kept replete for 96 hours under the culture conditions of Example 2 (using for example 40 L/min gas flow and agitation of 150 to 350 rpm and vessel pressure from 0 to 7.5 PSI). The 90 L culture starts at a density of 2 g/L algae dry weight and reaches 32 g/L after 96 hours. The culture conditions are then changed for nitrogen (specifically urea) to deplete for an additional 48 hours before harvest. Before nitrogen depletion (or other stress trigger) Norflurazon (50-100 µM) is added to the culture to inhibit phytoene desaturase to block or reduce the conversion of phytoene to other pigments. The freeze-dried or spray-dried biomass is extracted with hexane to obtain a substance containing phytoene and phytofluene, confirmed by UV spectrophotometry (phytoene absorbs in UVB $\lambda_{max}$=286 nm and phytofluene in UVA $\lambda_{max}$=348 nm). Solvent is removed by distillation, and the resulting substance (INCI: *Haematococcus* Pluvialis Extract) is solubilized in a composition with grapeseed oil (INCI: *Vitis Vinifera* (Grape) Seed Oil), hydrogenated polydecene oil (non-sticky emollient and moisturizer; INCI: Hydrogenated Polydecene), or VC-IP (oil-soluble Vitamin C; INCI: Ascorbyl Tetraisopalmitate) as a 0.1% phytoene/phytofluene solution. Following the SkinGuard 1.0 analyzer (LIUMY, Shenzen, China) UV index protocol per the manufacturer's directions, samples are tested at noon in an open area in direct tropical sunlight. The solution of phytoene/phytofluene reduces the UV index by 50%, meaning from "dangerous" to "medium" irradiation intensity. This can be further formulated into pre-sun and after-sun consumer products. The product may be in the form of a lotion, cream, spray, gel, lipstick, or other acceptable topical product form. As a pre-sun product ingredient, the colorless carotenoids are intended to help boost the performance of sunscreens by adding UVA-PF benefits, and by their own UV protection in the skin cells; as an after-sun product ingredient they can contribute antioxidant properties through quenching reactive free radicals such as hydroxyl radicals that are generated by skin exposure to UV. Consumed as a whole cell intact (non-milled) stable powder, biomass delivering 1 to 5 mg of phytoene and phytofluene daily also delivers protection for the skin and other health benefits. By the method of this invention, food-grade pigments and unpigmented precursors can be available for ingestion as the processing proceeds under sanitary conditions.

Figure 11:
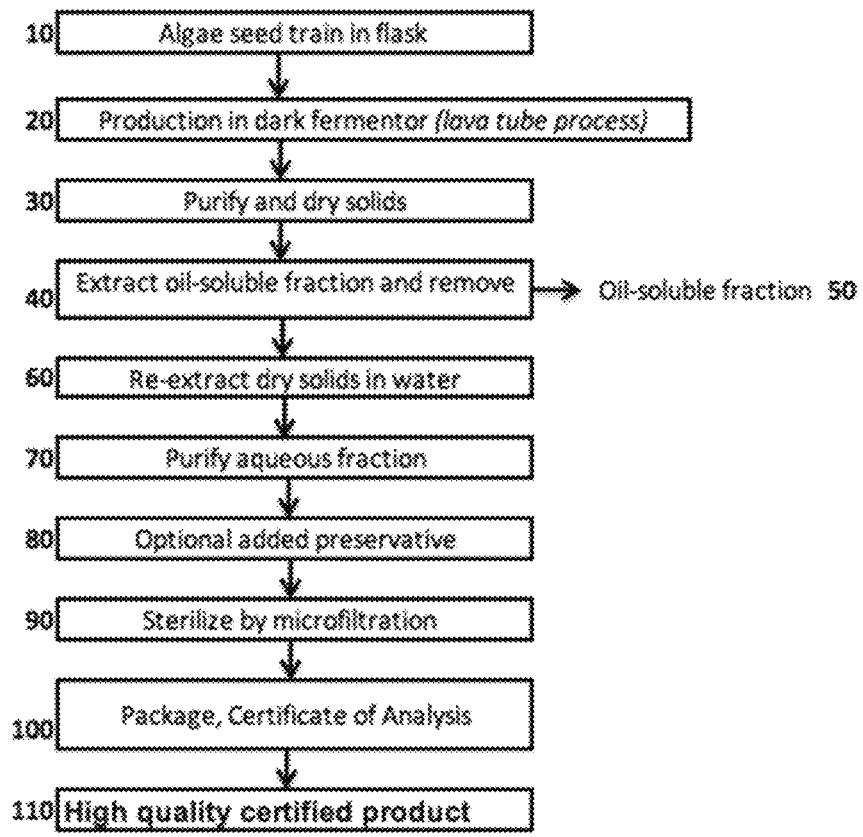
FIG. 11. General manufacturing flow for water-soluble carotenoids from eukaryotic algae.

Example 13-Microalgal Substance and Composition that Contains Water-Soluble Carotenoids This is the first example of industrial-scale manufacturing of water-soluble carotenoid-containing substance, referred to as "carotenoprotein", using a eukaryotic microalga. This example describes a novel hydrophilic carotenoid substance produced from *Haematococcus* pluvialis by the method of this invention. Biomass is produced in complete darkness in a 100-L fermentor following Example 12 (FIG. 11 step 10 and 20, including urea depletion in step 20 as a change in culture conditions to induce this new substance from *Haematococcus*) but without addition of the phytoene desaturase inhibitor. Following the FIG. 11 process, biomass that was previously dried in step 30 and extracted in step 40 to remove the oil-soluble fraction 50 (such as with ethanol or supercritical fluids) is dried again and then re-extracted with water in step 60. 50 grams of spent biomass per liter of water is extracted using a NutriBullet blender for 30 seconds. Solids are removed by centrifugation in step 70 and the colored supernatant is filter sterilized per step 90 after addition of 1% phenoxyethanol as preservative per step 80 when used for skin care. For industrial production, the method initially obtained 2.9 g product/L/hr over 6 days from a culture with a final density of 17.4 g/L algae for example using *Haematococcus* pluvialis KAS1708. Output can be improved and then maximized through strain selection and process improvements. The carotenoid species present, based on HPLC peaks as known in the art, include at least astaxanthin, lutein, zeaxanthin, and canthaxanthin moieties. Precursors such as doradexanthin may also be present. Stability is tested using colored aqueous extract of *Haematococcus* pluvialis grown heterotrophically in complete darkness at industrial scale of 100 L. An aqueous solution is temperature-stable up to at least 70° C. for at least 20 minutes, such as might be encountered during formulating. A dark orange/red solution is stable at room temperature stored in the dark, especially under refrigeration for a shelf life of at least 6 months. These stability features make it suitable for formulations in personal care. The composition of water-soluble carotenoids (INCI: Aqua (and) *Haematococcus* Pluvialis Extract) and preservative (INCI: Phenoxyethanol) is packaged per step 100 and stored refrigerated as a high-quality ingredient 110 for use in skin care. A composition for facial spray-mist stably incorporating water-soluble carotenoids produced by the method of this invention is comprised of *Haematococcus* pluvialis extract (3-7%), preservative (1-2%, such as phenoxyethanol or Leucidal®) along with moisturizing compounds (3-6%; such as aloe, hyaluronic acid, glycerin, polysaccharides, peptides), along with fragrance, texture and spreadability agent(s) as is known in the art, and water or other diluent to bring up to 100%. Such a composition could additionally include biologically active compounds between 0.5% to 10% (such as plant extracts, vitamins and such) depending on the desired performance outcomes. A composition of carotenoprotein mixture solubilized in water is adjusted to pH 7 with boric acid and preserved with an ophthalmic preservative as is known in the art for use in eye care. The water-soluble carotenoids by virtue of their molecular structure of long polyene chains with multiple double bonds have anti-oxidant properties to protect and restore cells from oxidative stress and free radicals. Carotenoproteins from other species, such as OCP, are known for their strong antioxidant capacity, notably for quenching singlet oxygen and photoprotection. When the *Haematococcus* water extract, placed on a layer of plastic wrap, is tested using the UV analyzer function of the SkinGuard device per Example 12, the UV index is reduced by 71%, meaning from "dangerous" to "very weak." A spectral scan from 200-600 nm shows absorbance in the ultraviolet and blue light, with peaks at 230 nm, 260 nm, 290 nm, and from 400-420 nm with a relative lower peak, with absorbance dropping off after above 550 nm. Unlike OCP, the color of the extracted *Haematococcus* water-soluble carotenoids does not change between dark and light conditions, and they form in cells under complete darkness after a change in nutrition, with no requirement for light (or high light) exposure whatsoever.

Its presence in induced whole cell biomass indicates suitability for applications such as nutritional products (for humans or animals including fish) without being extracted. Carotenoids as oil-soluble compounds are already known to provide animal (including fish and crustaceans, poultry, eggs) benefits. Consumers today demand natural, safe and sustainable ingredients for their food including seafood. Lipid-soluble astaxanthin produced by the microalga, *Haematococcus pluvialis*, is a proven and highly desirable choice for natural red pigmentation of flesh, skin, crustacean shells, and egg yolks. Astaxanthin also boosts overall animal health as a potent anti-oxidant and source of pro-vitamin A. These functions stimulate the immune system, protect against oxidative damage and stress, and improve growth, survivability, disease resistance, and reproduction. This is the first time that hydrophilic water-soluble algal carotenoids with astaxanthin, lutein, zeaxanthin, canthaxanthin and such are produced and integrated—with the whole cell biomass produced by the method of this invention-into a diet. For aquaculture, rates are at 20 to 200 g per ton feed measured on a carotenoid basis (such as total astaxanthin) and delivered in the form of dried algal feed material. For example, dried powdered algal biomass is added to pre-mix at a rate 50 ppm astaxanthin. After extrusion the pellets are used as an aquaculture feed for salmonids and shrimp to obtain coloration that meets the standards of the industry as measured visually as is known in the art. The biomass produced by the method of this invention can include both hydrophilic and hydrophobic (lipophilic) carotenoids to contribute to animal product coloration.

Example 14-Microalgal Substances and Compositions from Subterranean Cyanobacteria This example describes substances and compositions from two cyanobacterial microalgae taxa, *Oculatella* sp. and *Anabaena*. One source organism, *Oculatella*, is exemplified using KAS1561 *Oculatella* from a puddle in complete darkness in the transition dark zone of a lava tube. 16s DNA sequence per Example 1 shares 94% sequence identity to *Oculatella urcrainica* (GenBank accession MG652620.1), *Oculatella atacamensis* (GenBank accession KF761587.1), and *Leptolyngyna* sp. (*Oculatella neakameniensis* str. Kovacik; GenBank accession EU528672.2, found in semi-arid volcanic soil). *Oculatella* is recently separated from the genus *Leptolyngbya*, which is polyphyletic, and is recognized by the presence of rhodopsin as the photoreceptive pigment in the reddish inclusion at the tip of mature apical cells. The genus is known for its ability to grow under monochromatic red light. *Oculatella kauaiensis* was previously reported on the island of Kauai, Hawaiian Islands, in a dim sea wall cave near sea level but it likely belongs to a different clade than KAS1561 based on initial sequencing (FIG. 2 of Osorio-Santos et al. 2014).

Axenic stock cultures of KAS1561 are propagated and maintained in agarized 1.5% Zarrouck's medium with sodium nitrate under low light of 10 µmol photons/m$^2$/s. Inoculum was transferred into liquid BG11 in flask on a 100-rpm shaker at 25° C., pH 7.6. This is then scaled into 2 L clear bent-neck horizontal serum flasks prior to transfer into a GE Healthcare WAVE 25 Rocker with 22 L cell bags for intermittent feed of glucose and nutrient stocks, pH maintained at pH 7.6. Cultivation is in the dark with the exception of optional red light. To stimulate phycoerythrin production, cultures are transferred for two days to white light at 15 µmol photons/m$^2$/s. Cultures are harvested through screens, similar to *Arthrospira* and the biomass is lyophilized. Phycoerythrin is extracted following the protocol and calculations of Thoisen et al. 2017 used for the walless *Rhodomonas* microalga. The phycobiliprotein content shows a high amount of phycoerythrin. This is purified as known in the art to serve as a colorant in lip care compositions as described in Example 6.

A second cyanobacterial microalga, *Anabaena*, is exemplified using a nitrogen fixing KAS1533 *Anabaena variabilis* obtained from a lava tube wall scraping in the transition zone, with 98% match to *Anabaena variabilis* ATCC 29413 (GenBank accession HF678501.1) and *Dolichospermum* sp. (GenBank accession MH702207.1). Individual cells of the chains measure 2-4 µm, with prominent heterocysts. It grows in complete darkness on glucose, 28° C., pH maintained less than pH 8.2, eventually reaching two doublings per 24 hrs. It is exposed to a change in culture conditions with added hydrogen peroxide (0.1 mmol/L $H_2O_2$) and full nutrition for an additional two days to produce mycosporines and mycosporine-like amino acids (MAAs) that function to absorb harmful UV irradiation. Extracts are prepared as known in the art for microalgal MAAs.

Extract is used in a composition suited to incorporation of water-soluble molecules. In this way they can serve as a sunscreen compound in topical preparations to protect skin, lips, or coat substrates against damage by irradiation. One composition is described in the facial spray-mist of Example 13, wherein extract of MAAs is used at 5%, in addition to, or in place of, the hydrophilic *Haematococcus pluvialis* extract with a corresponding decrease in water. Another composition is in a face serum as described in Example 6, wherein extract of MAAs is added at 5% with corresponding decrease in water or other diluent. Another composition shows compatibility in moisturizing cream or lotion, formulated as follows: 5% extract of MAAs, 2% to 12% moisturizer/humectants, 3% to 6% texture agents, 5% to 15% oils, 5% to 15% emulsifiers, 55% water (or up to 100% as appropriate), 1% to 2% stabilizing antioxidants, fragrance, preservative and water or other diluent up to 100% as appropriate. Oil and water phases are homogenized together as is known in the art to form a composition suitable for topical administration. The amount in the cosmetic composition of the substances produced according to the method of the present invention is not limited and may range from 0.5% to 10% extract of MAAs by weight, preferably from 1 to 10% by weight, relative to the total weight of the composition.

REFERENCES

1. Abe K., Hattori H., Hirano M. 2007. Accumulation and antioxidant activity of secondary carotenoids in the aerial microalga *Coelastrella striolata* var. *multistriata*. Food Chem. 100, 656-661. 10.1016/j.foodchem.2005.10.026
2. Alam Md. N., Bristi N. L., Rafiquzzaman Md. 2013. Review on in vivo and in vitro methods evaluation of antioxidant activity. Saudi Pharmaceutical Journal 21:143-152. https://www.sciencedirect.com/science/article/pii/S1319016412000357
3. Bashan Y., H. Vierheilig, B. G. Salazar, L. E. de-Bashan. 2006. Primary colonization and breakdown of igneous rocks by endemic, succulent elephant trees (*Pachycormus discolor*) of the deserts in Baja California, Mexico. Naturwissenschaften (2006) 93:344-347 DOI 10.1007/s00114-006-0111-4
4. Chaiklahan R, Chirasuwan N, Bunnag B. 2012. Stability of phycocyanin extracted from *Spirulina* sp.: Influence of temperature, pH, and preservatives. Process Biochemistry 47:659-664.
5. Chauton, M. S., Skolem, L. M. B., Olsen, L. M., Vullum P E, Walmsley J, Vadstein O. 2015. Titanium uptake and incorporation into silica nanostructures by the diatom *Pinnularia* sp. (Bacillariophyceae). J Appl Phycol 27:777.
6. Delattre C., G. Pierre, C. Laroche, P. Michaud. 2016. Production, extraction and characterization of microalgal and cyanobacterial exopolysaccharides, Biotechnol Adv http://dx.doi.org/10.1016/j.biotechadv.2016.08.001
7. du Plessis J., A. Stefaniak, F. Eloff, S. John, T. Agner, T-C Chou, R. Nixon, M. Steiner, A. Franken, I. Kudla, and L. Holness. 2013. International guidelines for the in vivo assessment of skin properties in non-clinical settings: Part 2. transepidermal water loss and skin hydration. *Skin Res Technol*. 19 (3): 265-278. doi: 10.1111/srt.12037
8. Falasco E., L. Ector, M. Isaia, C. E. Wetzel, L. Hoffmann, and F. Bona. 2014. Diatom flora in subterranean ecosystems: a review. Intern J Speleology 43:231-251. http://dx.doi.org/10.5038/1827-806X.43.3.1
9. Gan F., Shen G., Bryant D. A. 2015. Occurrence of far-red light photoacclimation (FaRLiP) in diverse cyanobacteria. Life 5, 4-24.
10. Guillard R R L. 2005. Purification methods for microalgae. In: Andersen R A, Ed. Algal Culturing Techniques. Elsevier Inc; pp. 117-132.
11. Guillard R R L, Ryther J H. 1962. Studies of marine planktonic diatoms. I. *Cyclotella nana* Hustedt and *Detonula confervacea* Cleve. Can J Microbiol 8:229-39.
12. Guiry M. D. and Guiry G. M. 2018. AlgaeBase. Worldwide electronic publication, National University of Ireland, Galway. See world-wide-website: algaebase.org; accessed on 25 Apr. 2018.
13. Hanagata N. and Z. Dubinsky. 1999. Secondary carotenoid accumulation in *Scenedesmus komarekii* (Chlorophyceae, *Chlorophyta*). J. Phycol 35:960-966.
14. Howarth F., S. James, W. Mcdowell, D. J. Preston, C. Imada. 2007. Identification of roots in lava tube caves using molecular techniques: Implications for conservation of cave arthropod faunas. Journal of Insect Conservation. 11. 251-261. 10.1007/s10841-006-9040-y.
15. Jeffryes C, Gutu T, Jiao J, GL Rorrer. 2008. Metabolic insertion of nanostructured $TiO_2$ into the patterned biosilica of the diatom *Pinnularia* sp by a two-stage bioreactor cultivation process. ACS Nano. 2:2103-2112. DOI: 10.1021/nn800470x.
16. Malavasi V, Škaloud P, Rindi F, Tempesta S, Paoletti M, Pasqualetti M. 2016. DNA-Based Taxonomy in Ecologically Versatile Microalgae: A Re-Evaluation of the Species Concept within the Coccoid Green Algal Genus *Coccomyxa* (Trebouxiophyceae, *Chlorophyta*). PLOS ONE 11 (3): e0151137. doi: 10.1371/journal.pone.0151137
17. Meléndez-Martínez, A. J., P. Mapelli-Brahm, C. Stinco. 2018. The colourless carotenoids phytoene and phytofluene: From dietary sources to their usefulness for the functional foods and nutricosmetics industries. J Food Composition and Analysis. 67. 112. 10.1016/j.jfca.2018.01.002.
18. Minyuk G., E. Chelebieva, I. Chibchikova, N. Dantsyuk, I. Drobetskaya, E. Sakhon, K. Chekanov, A. Solovchenko. 2017. Stress-induced secondary carotenogenesis in *Coelastrella rubescens* (Scenedesmaceae, *Chlorophyta*), a producer of value-added keto-carotenoids. Algae 32 (3): 245-259.
19. Moreno M, Powers M, McQueen V M, Kuehl M M, Ong H C, Thomas D J. 2010. Microbial diversity in Ozark region caves. Astrobiology Science Conference 2010, 5142.
20. Nienow J. A. 1996. Ecology of subaerial algae. Nova Hedwigia, Beih. 112:537-552.
21. Osorio-Santos K., N. Pietrasiak, M. Bohunická, L. H. Miscoe, L. Kováčik, M. P. Martin, and J. R. Johansen. 2014. Seven new species of *Oculatella* (Pseudanabaenales, Cyanobacteria): taxonomically recognizing cryptic diversification, European Journal of Phycology, 49:4, 450-470, DOI: 10.1080/09670262.2014.976843
22. Prouty N. G., P. W. Swarzenski, J. K. Fackrell, K. Johannesson, C. D. Palmore. 2017. Groundwater-derived nutrient and trace element transport to a nearshore Kona coral ecosystem: Experimental mixing model results. J. Hydrol.: Reg. Stud. 11:166-177 http://dx.doi.org/10.1016/j.ejrh.2015.12.058
23. Rangkadilok N., Sitthimonchai S., Worasuttayangkurn L., et al. 2007. Evaluation of free radical scavenging and antityrosinase activities of standardized longan fruit extract. Food and Chemical Toxicology, 45:328-336.
24. Schumacher J. 2017. How light affects the life of *Botrytis*. Fungal Genetics and Biology 106:26-41.
25. Shimura H, Itoh K, Sugiyama A, et al. 2012. Absorption of radionuclides from the Fukushima nuclear accident by novel algal strain. PLOS One 2012; 7 (9): e95903. doi: 10.1371/journal/pone0095903.
26. Thoisen C., Hansen B. W., and Nielsen S. L. 2017. A simple and fast method for extraction and quantification of cryptophyte phycoerythrin. MethodsX, 4:209-213. http://doi.org/10.1016/j.mex.2017.06.002
27. Vinogradova O. N., O. V. Kovalenko, S. P. Wasser, E. Nevo, and M. Weinstein-Evron. 1998. Species diversity gradient to darkness stress in blue-green algae/cyanobacteria: A microscale test in a prehistoric cave, Mount Carmel, Israel. Isr. J. Plant Sci. 46:229-238.
28. Vinogradova O. N., E. Nev, S. P. Wasser. 2009. Algae of the Sefunim Cave (Israel): species diversity affected by light, humidity and rock stresses. International Journal on Algae, 2009, 11 (2): 99-116.
29. Wu H-L, G-H Wang, W-Z Xiang, T Li, H He. 2016. Stability and antioxidant activity of food-grade phycocyanin isolated from *Spirulina platensis*. International Journal of Food Properties, 19:10, 2349-2362, DOI: 10.1080/10942912.2015.1038564
30. Zammit G., D. Billi, P. Albertano. 2012. The subaerophytic cyanobacterium *Oculatella subterranea* (Oscillatoriales, Cyanophyceae) gen. et sp. nov.: a cytomorphological and molecular description, European Journal of Phycology, 47:4, 341-354

Patents/Patent Application Publications:
U.S. Pat. No. 8,927,522
U.S. Pat. No. 8,277,849B2
U.S. Pat. No. 9,278,122B2
EP2977462A1
EP2754710A1
JP6174219B2
TWI491349

We claim:

1. A composition comprising:
   a proteoglycan, wherein the proteoglycan comprises a microalgal exopolysaccharide covalently linked to at least one protein, wherein the microalgal exopolysaccharide comprises rhamnose, xylose, 3-O-methyl rhamnose, glucuronic acid, galactose, glucose, and mannose, or
   a microalgal water-soluble carotenoid complex, wherein the microalgal water-soluble carotenoid complex comprises astaxanthin, lutein, zeaxanthin, and canthaxanthin; and
   a carrier or excipient wherein the proteoglycan or the carotenoid complex is extracted from microalgae cultured in a purposeful change to a condition of nitrogen depletion.

2. The composition of claim 1, wherein the microalgal exopolysaccharide is from a *Parachlorella* species cell.

3. The composition of claim 2, wherein the *Parachlorella* species is *Parachlorella kessleri*.

4. The composition of claim 1, wherein the microalgal water-soluble carotenoid complex is from a *Haematococcus* species cell.

5. The composition of claim 4, wherein the *Haematococcus* species is *Haematococcus pluvialis*.

6. The composition of claim 1, wherein the composition is present in a microalgal biomass comprising a plurality of microalgal cells, a secretion of a plurality of microalgal cells, or an extract of a plurality of microalgal cells.

7. The composition of claim 1, wherein the composition further comprises additional pigment, protein, amino acid, carbohydrate, colorant, UV ray protectant or absorbent, antioxidant, metal chelator, blue-light attenuator, whitener, moisturizer, humectant, protein stabilizer, anti-frizz agent, anti-pollution agent, enzyme inhibitor, ophthalmic agent, a precursor or derivative thereof, or any combination of distinct agents thereof.

8. The composition of claim 7, wherein the pigment is an isoprenoid, fucoxanthin, lycopene, carotene, phytofluene, phytoene, a chlorophyll, a precursor or a derivative thereof or any combination of distinct pigments thereof.

9. The composition of claim 1, wherein the composition is an animal feed, a food, an ingredient used in personal care products, or a consumer product selected from the group consisting of a gel, oil, lotion, spray, cream, emulsion, lip care product, hair care product, and ointment.

10. The composition of claim 1, wherein the microalgal water-soluble carotenoid complex or exopolysaccharide is from a cell selected from the group consisting of KAS1543, KAS1544, KAS1545, KAS1562A, KAS1562B, KAS1537, KAS1565, KAS1566, KAS1535, KAS1708, KAS1601, KAS1561, KAS1562C, and KAS1533.

11. The composition of claim 9, wherein the composition comprises a cosmetically acceptable vehicle and the water-soluble carotenoid complex is from a *Haematococcus* species.

12. The composition of claim 11, wherein the *Haematococcus* species is *Haematococcus pluvialis*.

13. The composition of claim 9, wherein the composition comprises a cosmetically acceptable vehicle and the exopolysaccharide from a *Parachlorella* species.

14. The composition of claim 13, wherein the *Parachlorella* species is *Parachlorella kessleri*.

15. The composition of claim 1, wherein the microalgal water-soluble carotenoid complex or exopolysaccharide is from a cell from a taxon selected from *Cyanoprokaryota, Chlorophyta, Bacillariophyta, Xanthophyta*, or *Charophyta*.

16. The composition of claim 1, wherein the microalgal water-soluble carotenoid complex or exopolysaccharide is from a cell from a genus selected from *Anabaena, Parachlorella, Desmodesmus, Scenedesmus, Monoraphidium, Coelastrella, Chlorella, Coccomyxa, Pseudococcomyxa, Klebsormidium, Haematococcus, Hantzschia, Aulacoseira, Nitzschia, Navicula, Humidophila, Diadesmis, Eolimna, Sellaphora, Chamaepinnularia, Chroococcus, Mychonastes, Nostoc, Oculatella, Leptolyngbya, Dolichospermum, Geissleria*, or *Navigolum*.

17. The composition of claim 1, wherein the proteoglycan comprises a microalgal exopolysaccharide covalently linked to at least one protein, resulting in added hydration and stability as compared to the protein in an unlinked state.

18. The composition of claim 1, wherein the microalgal water-soluble carotenoid complex further comprises doradexanthin.

* * * * *